United States Patent
Williams et al.

(10) Patent No.: US 9,574,014 B2
(45) Date of Patent: Feb. 21, 2017

(54) CHIMERIC ANTIGEN RECEPTOR COMPOSITIONS

(71) Applicant: City of Hope, Duarte, CA (US)

(72) Inventors: John C. Williams, Monrovia, CA (US); Christine Brown, Pasadena, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

(21) Appl. No.: 15/156,159

(22) Filed: May 16, 2016

(65) Prior Publication Data

US 2016/0333114 A1    Nov. 17, 2016

Related U.S. Application Data

(60) Provisional application No. 62/162,599, filed on May 15, 2015.

(51) Int. Cl.
| | | |
|---|---|---|
| C07K 16/40 | (2006.01) | |
| C07K 14/705 | (2006.01) | |
| C07K 14/725 | (2006.01) | |

(52) U.S. Cl.
CPC ........... *C07K 16/40* (2013.01); *C07K 14/7051* (2013.01); *C07K 14/70521* (2013.01); *C07K 2317/24* (2013.01); *C07K 2317/622* (2013.01); *C07K 2319/03* (2013.01); *C07K 2319/70* (2013.01)

(58) Field of Classification Search
None
See application file for complete search history.

(56) References Cited

U.S. PATENT DOCUMENTS

| | | | |
|---|---|---|---|
| 5,359,046 A | 10/1994 | Capon et al. | |
| 7,563,441 B2 | 7/2009 | Graus et al. | |
| 2012/0301400 A1 | 11/2012 | Williams et al. | |
| 2012/0301447 A1* | 11/2012 | Jensen ................... | C07K 14/71 424/93.21 |
| 2015/0030535 A1 | 1/2015 | Williams et al. | |

FOREIGN PATENT DOCUMENTS

| | | |
|---|---|---|
| EP | 2 995 682 A1 | 3/2016 |
| WO | WO-2013055404 A1 | 4/2013 |
| WO | WO-2014/180306 A1 | 11/2014 |
| WO | WO-2015105522 A1 | 7/2015 |
| WO | WO-2016054603 A2 | 4/2016 |

OTHER PUBLICATIONS

Johnson et al., Sci Transl Med. Feb. 18, 2015; 7(275): 275ra22, p. 1-14.*
Jensen et al. Curr Opin Immunol. Apr. 2015; 33: 9-15. (Epub Jan. 23, 2015).*
Avery et al., "Development of a High Affinity, Non-covalent Biologic to Add Functionality to Fabs," Scientific Reports, 5-7817 (2015).
Davila et al., "Efficacy and toxicity management of 19-28z CAR T cell therapy in B cell acute lymphoblastic leukemia," Sci Transl Med. 6(224):224ra25 (2014).
Donaldson et al., "Identification and grafting of a unique peptide-binding site in the Fab framework of monoclonal antibodies," Proc Natl Acad Sci U S A. 110(43):17456-17461 (2013).
Guest et al., "The role of extracellular spacer regions in the optimal design of chimeric immune receptors: evaluation of four different scFvs and antigens," J. Immunother. 28(3):203-211 (2005).
Kalos, M. and C. June, "Adoptive T cell transfer for cancer immunotherapy in the era of synthetic biology," Immunity 39(1):49-60 (2013).
Kochenderfer et al., "B-cell depletion and remissions of malignancy along with cytokine-associated toxicity in a clinical trial of anti-CD19 chimeric-antigen-receptor-transduced T cells," Blood, 119(12):2709-2720 (2012).
Rossi et al., "Stably tethered multifunctional structures of defined composition made by the dock and lock method for use in cancer targeting," Proc Natl Acad Sci U S A. 103(18):6841-6846 (2006).
Symczak et al., "Correction of multi-gene deficiency in vivo using a single 'self-cleaving' 2A peptide-based retroviral vector," Nat Biotechnol. 22(5):589-594 (2004).
International Search Report mailed on Aug. 31, 2016, for PCT Application No. PCT/US2016/32780, filed on May 16, 2016, 6 pages.
Written Opinion mailed on Aug. 31, 2016, for PCT Application No. PCT/US2016/32780, filed on May 16, 2016, 7 pages.

* cited by examiner

*Primary Examiner* — Ilia Ouspenski
(74) *Attorney, Agent, or Firm* — Mintz Levin Cohn Ferris Glovsky and Popeo, P.C.

(57) ABSTRACT

Provided herein are compositions which exhibit novel diagnostic capabilities and allow to rapidly add functionality to adoptive immunotherapy. The compositions include isolated nucleic acids encoding proteins including antibody regions capable of binding compounds including a peptidyl moiety (e.g., a meditope). The recombinant proteins provided herein are useful, inter alia, for a broad variety of therapeutic and diagnostic purposes. For example, the recombinant proteins provided herein including embodiments thereof may be used as non-invasive means to characterize chimeric antigen receptor (CAR) T cells before and/or during treatment of diseases (e.g., cancer).

20 Claims, 20 Drawing Sheets

HER2

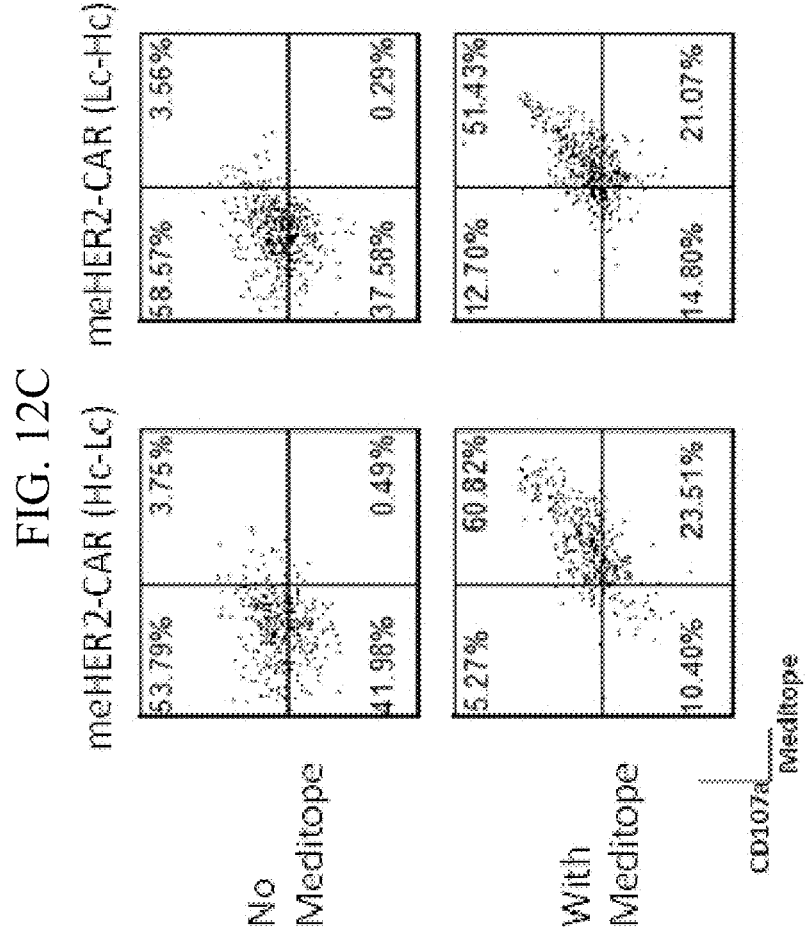

SEQUENCE LISTING

<160> NUMBER OF SEQ ID NOS: 110

<210> SEQ ID NO 1
<211> LENGTH: 21
<212> TYPE: PRT
<213> ORGANISM: Artificial Sequence
<220> FEATURE:
<223> OTHER INFORMATION: Synthetic polypeptide

```
<400> SEQUENCE: 1

Leu Cys Tyr Leu Leu Asp Gly Ile Leu Phe Ile Tyr Gly Val Ile Leu
1               5                   10                  15

Thr Ala Leu Phe Leu
            20

<210> SEQ ID NO 2
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 2

Phe Trp Val Leu Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 3
<211> LENGTH: 22
<212> TYPE: PRT
<213> ORGANISM: Artificial Sequence
<220> FEATURE:
<223> OTHER INFORMATION: Synthetic polypeptide

<400> SEQUENCE: 3

Met Ala Leu Ile Val Leu Gly Gly Val Ala Gly Leu Leu Leu Phe Ile
1               5                   10                  15

Gly Leu Gly Ile Phe Phe
            20

<210> SEQ ID NO 4
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 4

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 5
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 5

Ile Tyr Ile Trp Ala Pro Leu Ala Gly Thr Cys Gly Val Leu Leu Leu
1               5                   10                  15

Ser Leu Val Ile Thr Leu Tyr
            20

<210> SEQ ID NO 6
<211> LENGTH: 24
<212> TYPE: PRT
<213> ORGANISM: Artificial Sequence
<220> FEATURE:
<223> OTHER INFORMATION: Synthetic polypeptide
```

```
<400> SEQUENCE: 6

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 7
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 7

Ile Ile Ser Phe Phe Leu Ala Leu Thr Ser Thr Ala Leu Leu Phe Leu
1               5                   10                  15

Leu Phe Phe Leu Thr Leu Arg Phe Ser Val Val
            20                  25

<210> SEQ ID NO 8
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 8

Val Ala Ala Ile Leu Gly Leu Gly Leu Val Leu Gly Leu Leu Gly Pro
1               5                   10                  15

Leu Ala Ile Leu Leu
            20

<210> SEQ ID NO 9
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 9

Phe Trp Leu Pro Ile Gly Cys Ala Ala Phe Val Val Val Cys Ile Leu
1               5                   10                  15

Gly Cys Ile Leu Ile
            20

<210> SEQ ID NO 10
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 10

Pro Leu Phe Ile Pro Val Ala Val Met Val Thr Ala Phe Ser Gly Leu
1               5                   10                  15

Ala Phe Ile Ile Trp Leu Ala
            20

<210> SEQ ID NO 11
<211> LENGTH: 60
<212> TYPE: PRT
<213> ORGANISM: Artificial Sequence
<220> FEATURE:
```

<223> OTHER INFORMATION: Synthetic polypeptide

<400> SEQUENCE: 11

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr
    50                  55                  60

<210> SEQ ID NO 12
<211> LENGTH: 41
<212> TYPE: PRT
<213> ORGANISM: Artificial Sequence
<220> FEATURE:
<223> OTHER INFORMATION: Synthetic polypeptide

<400> SEQUENCE: 12

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 13
<211> LENGTH: 41
<212> TYPE: PRT
<213> ORGANISM: Artificial Sequence
<220> FEATURE:
<223> OTHER INFORMATION: Synthetic polypeptide

<400> SEQUENCE: 13

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 14
<211> LENGTH: 42
<212> TYPE: PRT
<213> ORGANISM: Artificial Sequence
<220> FEATURE:
<223> OTHER INFORMATION: Synthetic polypeptide

<400> SEQUENCE: 14

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 15
<211> LENGTH: 42
<212> TYPE: PRT
<213> ORGANISM: Artificial Sequence
<220> FEATURE:

<223> OTHER INFORMATION: Synthetic polypeptide

<400> SEQUENCE: 15

Ala Leu Tyr Leu Leu Arg Arg Asp Gln Arg Leu Pro Pro Asp Ala His
1               5                   10                  15

Lys Pro Pro Gly Gly Gly Ser Phe Arg Thr Pro Ile Gln Glu Glu Gln
            20                  25                  30

Ala Asp Ala His Ser Thr Leu Ala Lys Ile
        35                  40

<210> SEQ ID NO 16
<211> LENGTH: 38
<212> TYPE: PRT
<213> ORGANISM: Artificial Sequence
<220> FEATURE:
<223> OTHER INFORMATION: Synthetic polypeptide

<400> SEQUENCE: 16

Cys Trp Leu Thr Lys Lys Lys Tyr Ser Ser Val His Asp Pro Asn
1               5                   10                  15

Gly Glu Tyr Met Phe Met Arg Ala Val Asn Thr Ala Lys Lys Ser Arg
            20                  25                  30

Leu Thr Asp Val Thr Leu
        35

<210> SEQ ID NO 17
<211> LENGTH: 818
<212> TYPE: PRT
<213> ORGANISM: Artificial Sequence
<220> FEATURE:
<223> OTHER INFORMATION: Synthetic polypeptide

<400> SEQUENCE: 17

Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Asn Ile Lys Asp Thr Tyr Ile His Trp Val Arg Gln Ser Pro Gly
    50                  55                  60

Lys Gly Leu Glu Trp Val Ala Arg Ile Tyr Pro Thr Asn Gly Tyr Thr
65                  70                  75                  80

Arg Tyr Ala Asp Ser Val Lys Gly Arg Phe Thr Ile Ser Ala Asp Thr
                85                  90                  95

Ser Lys Asn Thr Ala Tyr Leu Gln Met Asn Ser Leu Arg Ala Glu Asp
            100                 105                 110

Thr Ala Ile Tyr Tyr Cys Ser Arg Trp Gly Gly Asp Gly Phe Tyr Ala
        115                 120                 125

Met Asp Tyr Trp Gly Gln Gly Thr Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser

```
              195                 200                 205
Ser Val Val Thr Val Pro Ser Ser Leu Gly Thr Gln Thr Tyr Ile
    210                 215                 220
Cys Asn Val Asn His Lys Pro Ser Asn Thr Lys Val Asp Lys Lys Val
225                 230                 235                 240
Glu Pro Lys Ser Cys Glu Ser Lys Tyr Gly Pro Pro Cys Pro Pro Cys
                245                 250                 255
Pro Gly Gly Gly Ser Ser Gly Gly Gly Ser Gly Gly Gln Pro Arg Glu
                260                 265                 270
Pro Gln Val Tyr Thr Leu Pro Pro Ser Gln Glu Glu Met Thr Lys Asn
        275                 280                 285
Gln Val Ser Leu Thr Cys Leu Val Lys Gly Phe Tyr Pro Ser Asp Ile
    290                 295                 300
Ala Val Glu Trp Glu Ser Asn Gly Gln Pro Glu Asn Asn Tyr Lys Thr
305                 310                 315                 320
Thr Pro Pro Val Leu Asp Ser Asp Gly Ser Phe Phe Leu Tyr Ser Arg
                325                 330                 335
Leu Thr Val Asp Lys Ser Arg Trp Gln Glu Gly Asn Val Phe Ser Cys
                340                 345                 350
Ser Val Met His Glu Ala Leu His Asn His Tyr Thr Gln Lys Ser Leu
                355                 360                 365
Ser Leu Ser Leu Gly Lys Met Phe Trp Val Leu Val Val Val Gly Gly
        370                 375                 380
Val Leu Ala Cys Tyr Ser Leu Leu Val Thr Val Ala Phe Ile Ile Phe
385                 390                 395                 400
Trp Val Arg Ser Lys Arg Ser Arg Gly Gly His Ser Asp Tyr Met Asn
                405                 410                 415
Met Thr Pro Arg Arg Pro Gly Pro Thr Arg Lys His Tyr Gln Pro Tyr
                420                 425                 430
Ala Pro Pro Arg Asp Phe Ala Ala Tyr Arg Ser Gly Gly Gly Arg Val
                435                 440                 445
Lys Phe Ser Arg Ser Ala Asp Ala Pro Ala Tyr Gln Gln Gly Gln Asn
        450                 455                 460
Gln Leu Tyr Asn Glu Leu Asn Leu Gly Arg Arg Glu Glu Tyr Asp Val
465                 470                 475                 480
Leu Asp Lys Arg Arg Gly Arg Asp Pro Glu Met Gly Gly Lys Pro Arg
                485                 490                 495
Arg Lys Asn Pro Gln Glu Gly Leu Tyr Asn Glu Leu Gln Lys Asp Lys
                500                 505                 510
Met Ala Glu Ala Tyr Ser Glu Ile Gly Met Lys Gly Glu Arg Arg Arg
                515                 520                 525
Gly Lys Gly His Asp Gly Leu Tyr Gln Gly Leu Ser Thr Ala Thr Lys
        530                 535                 540
Asp Thr Tyr Asp Ala Leu His Met Gln Ala Leu Pro Pro Arg Leu Glu
545                 550                 555                 560
Gly Gly Gly Glu Gly Arg Gly Ser Leu Leu Thr Cys Gly Asp Val Glu
                565                 570                 575
Glu Asn Pro Gly Pro Arg Met Leu Leu Leu Val Thr Ser Leu Leu Leu
                580                 585                 590
Cys Glu Leu Pro His Pro Ala Phe Leu Leu Ile Pro Asp Ile Gln Met
                595                 600                 605
Thr Gln Ser Pro Ile Leu Leu Ser Ala Ser Val Gly Asp Arg Val Thr
        610                 615                 620
```

```
Ile Thr Cys Arg Ala Ser Gln Asp Val Asn Thr Ala Val Ala Trp Tyr
625                 630                 635                 640

Gln Gln Arg Thr Asn Gly Ser Pro Arg Leu Leu Ile Tyr Ser Ala Ser
            645                 650                 655

Phe Leu Tyr Ser Gly Val Pro Ser Arg Phe Ser Gly Ser Arg Ser Gly
        660                 665                 670

Thr Asp Phe Thr Leu Thr Ile Ser Ser Leu Gln Pro Glu Asp Glu Ala
    675                 680                 685

Asp Tyr Tyr Cys Gln Gln His Tyr Thr Thr Pro Pro Thr Phe Gly Ala
690                 695                 700

Gly Thr Lys Val Glu Ile Lys Arg Thr Val Ala Ala Pro Ser Val Phe
705                 710                 715                 720

Ile Phe Pro Pro Ser Asp Glu Gln Leu Lys Ser Gly Thr Ala Ser Val
                725                 730                 735

Val Cys Leu Leu Asn Asn Phe Tyr Pro Arg Glu Ala Lys Val Gln Trp
            740                 745                 750

Lys Val Asp Asn Ala Leu Gln Ser Gly Asn Ser Gln Glu Ser Val Thr
        755                 760                 765

Glu Gln Asp Ser Lys Asp Ser Thr Tyr Ser Leu Ser Ser Thr Leu Thr
    770                 775                 780

Leu Ser Lys Ala Asp Tyr Glu Lys His Lys Val Tyr Ala Cys Glu Val
785                 790                 795                 800

Thr His Gln Gly Leu Ser Ser Pro Val Thr Lys Ser Phe Asn Arg Gly
                805                 810                 815

Glu Cys

<210> SEQ ID NO 18
<211> LENGTH: 22
<212> TYPE: PRT
<213> ORGANISM: Artificial Sequence
<220> FEATURE:
<223> OTHER INFORMATION: Synthetic polypeptide

<400> SEQUENCE: 18

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 19
<211> LENGTH: 223
<212> TYPE: PRT
<213> ORGANISM: Artificial Sequence
<220> FEATURE:
<223> OTHER INFORMATION: Synthetic polypeptide

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ser Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80
```

-continued

Leu Gln Met Asn Ser Leu Arg Ala Glu Asp Thr Ala Ile Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys
    210                 215                 220

<210> SEQ ID NO 20
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 20

Glu Ser Lys Tyr Gly Pro Pro Cys Pro Pro Cys Pro
1               5                   10

<210> SEQ ID NO 21
<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 21

Gly Gly Gly Ser Ser Gly Gly Ser Gly Gly Gln Pro Arg Glu Pro
1               5                   10                  15

Gln Val Tyr Thr Leu Pro Pro Ser Gln Glu Glu Met Thr Lys Asn Gln
                20                  25                  30

Val Ser Leu Thr Cys Leu Val Lys Gly Phe Tyr Pro Ser Asp Ile Ala
            35                  40                  45

Val Glu Trp Glu Ser Asn Gly Gln Pro Glu Asn Asn Tyr Lys Thr Thr
        50                  55                  60

Pro Pro Val Leu Asp Ser Asp Gly Ser Phe Phe Leu Tyr Ser Arg Leu
65                  70                  75                  80

Thr Val Asp Lys Ser Arg Trp Gln Glu Gly Asn Val Phe Ser Cys Ser
                85                  90                  95

Val Met His Glu Ala Leu His Asn His Tyr Thr Gln Lys Ser Leu Ser
                100                 105                 110

Leu Ser Leu Gly Lys
            115

<210> SEQ ID NO 22
<211> LENGTH: 28
<212> TYPE: PRT

<213> ORGANISM: Artificial Sequence
<220> FEATURE:
<223> OTHER INFORMATION: Synthetic polypeptide

<400> SEQUENCE: 22

Met Phe Trp Val Leu Val Val Gly Gly Val Leu Ala Cys Tyr Ser
1               5                   10                  15

Leu Leu Val Thr Val Ala Phe Ile Ile Phe Trp Val
            20                  25

<210> SEQ ID NO 23
<211> LENGTH: 41
<212> TYPE: PRT
<213> ORGANISM: Artificial Sequence
<220> FEATURE:
<223> OTHER INFORMATION: Synthetic polypeptide

<400> SEQUENCE: 23

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 24
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 24

Gly Gly Gly
1

<210> SEQ ID NO 25
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 25

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 26
<211> LENGTH: 24
<212> TYPE: PRT

```
<213> ORGANISM: Artificial Sequence
<220> FEATURE:
<223> OTHER INFORMATION: Synthetic polypeptide

<400> SEQUENCE: 26

Leu Glu Gly Gly Gly Glu Gly Arg Gly Ser Leu Leu Thr Cys Gly Asp
1               5                   10                  15

Val Glu Glu Asn Pro Gly Pro Arg
            20

<210> SEQ ID NO 27
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 27

Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Arg Thr Asn Gly Ser Pro Arg Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Glu Ala Asp Tyr Tyr Cys Gln Gln His Tyr Thr Thr Pro Pro
                85                  90                  95

Thr Phe Gly Ala Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 28
<211> LENGTH: 1162
<212> TYPE: PRT
<213> ORGANISM: Artificial Sequence
<220> FEATURE:
<223> OTHER INFORMATION: Synthetic polypeptide

<400> SEQUENCE: 28

Met Leu Leu Leu Val Thr Ser Leu Leu Cys Glu Leu Pro His Pro
1               5                   10                  15

Ala Phe Leu Leu Ile Pro Glu Val Gln Leu Val Glu Ser Gly Gly Gly
            20                  25                  30
```

```
Leu Val Gln Pro Gly Gly Ser Leu Arg Leu Ser Cys Ala Ala Ser Gly
            35                  40                  45

Phe Asn Ile Lys Asp Thr Tyr Ile His Trp Val Arg Gln Ser Pro Gly
 50                  55                  60

Lys Gly Leu Glu Trp Val Ala Arg Ile Tyr Pro Thr Asn Gly Tyr Thr
 65                  70                  75                  80

Arg Tyr Ala Asp Ser Val Lys Gly Arg Phe Thr Ile Ser Ala Asp Thr
                 85                  90                  95

Ser Lys Asn Thr Ala Tyr Leu Gln Met Asn Ser Leu Arg Ala Glu Asp
                100                 105                 110

Thr Ala Ile Tyr Tyr Cys Ser Arg Trp Gly Gly Asp Gly Phe Tyr Ala
            115                 120                 125

Met Asp Tyr Trp Gly Gln Gly Thr Leu Val Thr Val Ser Ser Ala Ser
130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
                180                 185                 190

His Thr Phe Pro Ala Val Leu Gln Ser Ser Gly Leu Tyr Ser Leu Ser
            195                 200                 205

Ser Val Val Thr Val Pro Ser Ser Leu Gly Thr Gln Thr Tyr Ile
        210                 215                 220

Cys Asn Val Asn His Lys Pro Ser Asn Thr Lys Val Asp Lys Lys Val
225                 230                 235                 240

Glu Pro Lys Ser Cys Glu Ser Lys Tyr Gly Pro Pro Cys Pro Pro Cys
                245                 250                 255

Pro Gly Gly Gly Ser Ser Gly Gly Ser Gly Gly Gln Pro Arg Glu
                260                 265                 270

Pro Gln Val Tyr Thr Leu Pro Pro Ser Gln Glu Glu Met Thr Lys Asn
            275                 280                 285

Gln Val Ser Leu Thr Cys Leu Val Lys Gly Phe Tyr Pro Ser Asp Ile
290                 295                 300

Ala Val Glu Trp Glu Ser Asn Gly Gln Pro Glu Asn Asn Tyr Lys Thr
305                 310                 315                 320

Thr Pro Pro Val Leu Asp Ser Asp Gly Ser Phe Phe Leu Tyr Ser Arg
                325                 330                 335

Leu Thr Val Asp Lys Ser Arg Trp Gln Glu Gly Asn Val Phe Ser Cys
                340                 345                 350

Ser Val Met His Glu Ala Leu His Asn His Tyr Thr Gln Lys Ser Leu
            355                 360                 365

Ser Leu Ser Leu Gly Lys Met Phe Trp Val Leu Val Val Val Gly Gly
370                 375                 380

Val Leu Ala Cys Tyr Ser Leu Leu Val Thr Val Ala Phe Ile Ile Phe
385                 390                 395                 400

Trp Val Arg Ser Lys Arg Ser Arg Gly Gly His Ser Asp Tyr Met Asn
                405                 410                 415

Met Thr Pro Arg Arg Pro Gly Pro Thr Arg Lys His Tyr Gln Pro Tyr
            420                 425                 430

Ala Pro Pro Arg Asp Phe Ala Ala Tyr Arg Ser Gly Gly Gly Arg Val
            435                 440                 445
```

-continued

```
Lys Phe Ser Arg Ser Ala Asp Ala Pro Ala Tyr Gln Gly Gln Asn
    450                 455                 460
Gln Leu Tyr Asn Glu Leu Asn Leu Gly Arg Arg Glu Glu Tyr Asp Val
465                 470                 475                 480
Leu Asp Lys Arg Arg Gly Arg Asp Pro Glu Met Gly Gly Lys Pro Arg
                485                 490                 495
Arg Lys Asn Pro Gln Glu Gly Leu Tyr Asn Glu Leu Gln Lys Asp Lys
                500                 505                 510
Met Ala Glu Ala Tyr Ser Glu Ile Gly Met Lys Gly Glu Arg Arg Arg
            515                 520                 525
Gly Lys Gly His Asp Gly Leu Tyr Gln Gly Leu Ser Thr Ala Thr Lys
530                 535                 540
Asp Thr Tyr Asp Ala Leu His Met Gln Ala Leu Pro Pro Arg Leu Glu
545                 550                 555                 560
Gly Gly Gly Glu Gly Arg Gly Ser Leu Leu Thr Cys Gly Asp Val Glu
                565                 570                 575
Glu Asn Pro Gly Pro Arg Met Pro Pro Arg Leu Leu Phe Phe Leu
                580                 585                 590
Leu Phe Leu Thr Pro Met Glu Val Arg Pro Glu Glu Pro Leu Val Val
        595                 600                 605
Lys Val Glu Glu Gly Asp Asn Ala Val Leu Gln Cys Leu Lys Gly Thr
610                 615                 620
Ser Asp Gly Pro Thr Gln Gln Leu Thr Trp Ser Arg Glu Ser Pro Leu
625                 630                 635                 640
Lys Pro Phe Leu Lys Leu Ser Leu Gly Leu Pro Gly Leu Gly Ile His
                645                 650                 655
Met Arg Pro Leu Ala Ile Trp Leu Phe Ile Phe Asn Val Ser Gln Gln
            660                 665                 670
Met Gly Gly Phe Tyr Leu Cys Gln Pro Gly Pro Pro Ser Glu Lys Ala
        675                 680                 685
Trp Gln Pro Gly Trp Thr Val Asn Val Glu Gly Ser Gly Glu Leu Phe
        690                 695                 700
Arg Trp Asn Val Ser Asp Leu Gly Gly Leu Gly Cys Gly Leu Lys Asn
705                 710                 715                 720
Arg Ser Ser Glu Gly Pro Ser Ser Pro Ser Gly Lys Leu Met Ser Pro
                725                 730                 735
Lys Leu Tyr Val Trp Ala Lys Asp Arg Pro Glu Ile Trp Glu Gly Glu
            740                 745                 750
Pro Pro Cys Val Pro Arg Asp Ser Leu Asn Gln Ser Leu Ser Gln
            755                 760                 765
Asp Leu Thr Met Ala Pro Gly Ser Thr Leu Trp Leu Ser Cys Gly Val
770                 775                 780
Pro Pro Asp Ser Val Ser Arg Gly Pro Leu Ser Trp Thr His Val His
785                 790                 795                 800
Pro Lys Gly Pro Lys Ser Leu Leu Ser Leu Glu Leu Lys Asp Asp Arg
                805                 810                 815
Pro Ala Arg Asp Met Trp Val Met Glu Thr Gly Leu Leu Pro Arg
            820                 825                 830
Ala Thr Ala Gln Asp Ala Gly Lys Tyr Tyr Cys His Arg Gly Asn Leu
            835                 840                 845
Thr Met Ser Phe His Leu Glu Ile Thr Ala Arg Pro Val Leu Trp His
850                 855                 860
Trp Leu Leu Arg Thr Gly Gly Trp Lys Val Ser Ala Val Thr Leu Ala
```

```
                865                 870                 875                 880
Tyr Leu Ile Phe Cys Leu Cys Ser Leu Val Gly Ile Leu His Leu Gln
                    885                 890                 895
Arg Ala Leu Val Leu Arg Arg Lys Arg Gly Gly Ser Thr Ser Glu Gly
                    900                 905                 910
Arg Gly Ser Leu Leu Thr Cys Gly Asp Val Glu Glu Asn Pro Gly Pro
                    915                 920                 925
Met Glu Thr Asp Thr Leu Leu Leu Trp Val Leu Leu Leu Trp Val Pro
                    930                 935                 940
Gly Ser Thr Gly Asp Ile Gln Met Thr Gln Ser Pro Ile Leu Leu Ser
945                 950                 955                 960
Ala Ser Val Gly Asp Arg Val Thr Ile Thr Cys Arg Ala Ser Gln Asp
                    965                 970                 975
Val Asn Thr Ala Val Ala Trp Tyr Gln Gln Arg Thr Asn Gly Ser Pro
                    980                 985                 990
Arg Leu Leu Ile Tyr Ser Ala Ser Phe Leu Tyr Ser Gly Val Pro Ser
                    995                 1000                1005
Arg Phe Ser Gly Ser Arg Ser Gly Thr Asp Phe Thr Leu Thr Ile
                    1010                1015                1020
Ser Ser Leu Gln Pro Glu Asp Glu Ala Asp Tyr Tyr Cys Gln Gln
                    1025                1030                1035
His Tyr Thr Thr Pro Pro Thr Phe Gly Ala Gly Thr Lys Val Glu
                    1040                1045                1050
Ile Lys Arg Thr Val Ala Ala Pro Ser Val Phe Ile Phe Pro Pro
                    1055                1060                1065
Ser Asp Glu Gln Leu Lys Ser Gly Thr Ala Ser Val Val Cys Leu
                    1070                1075                1080
Leu Asn Asn Phe Tyr Pro Arg Glu Ala Lys Val Gln Trp Lys Val
                    1085                1090                1095
Asp Asn Ala Leu Gln Ser Gly Asn Ser Gln Glu Ser Val Thr Glu
                    1100                1105                1110
Gln Asp Ser Lys Asp Ser Thr Tyr Ser Leu Ser Ser Thr Leu Thr
                    1115                1120                1125
Leu Ser Lys Ala Asp Tyr Glu Lys His Lys Val Tyr Ala Cys Glu
                    1130                1135                1140
Val Thr His Gln Gly Leu Ser Ser Pro Val Thr Lys Ser Phe Asn
                    1145                1150                1155
Arg Gly Glu Cys
                    1160

<210> SEQ ID NO 29
<211> LENGTH: 323
<212> TYPE: PRT
<213> ORGANISM: Artificial Sequence
<220> FEATURE:
<223> OTHER INFORMATION: Synthetic polypeptide

<400> SEQUENCE: 29

Met Pro Pro Pro Arg Leu Leu Phe Phe Leu Leu Phe Leu Thr Pro Met
1               5                   10                  15
Glu Val Arg Pro Glu Glu Pro Leu Val Val Lys Val Glu Glu Gly Asp
                20                  25                  30
Asn Ala Val Leu Gln Cys Leu Lys Gly Thr Ser Asp Gly Pro Thr Gln
                35                  40                  45
Gln Leu Thr Trp Ser Arg Glu Ser Pro Leu Lys Pro Phe Leu Lys Leu
```

```
                    50                  55                  60
Ser Leu Gly Leu Pro Gly Leu Gly Ile His Met Arg Pro Leu Ala Ile
 65                  70                  75                  80

Trp Leu Phe Ile Phe Asn Val Ser Gln Gln Met Gly Gly Phe Tyr Leu
                     85                  90                  95

Cys Gln Pro Gly Pro Pro Ser Glu Lys Ala Trp Gln Pro Gly Trp Thr
                100                 105                 110

Val Asn Val Glu Gly Ser Gly Glu Leu Phe Arg Trp Asn Val Ser Asp
                115                 120                 125

Leu Gly Gly Leu Gly Cys Gly Leu Lys Asn Arg Ser Ser Glu Gly Pro
130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Val Pro Pro
                165                 170                 175

Arg Asp Ser Leu Asn Gln Ser Leu Ser Gln Asp Leu Thr Met Ala Pro
                180                 185                 190

Gly Ser Thr Leu Trp Leu Ser Cys Gly Val Pro Pro Asp Ser Val Ser
                195                 200                 205

Arg Gly Pro Leu Ser Trp Thr His Val His Pro Lys Gly Pro Lys Ser
                210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
                260                 265                 270

Glu Ile Thr Ala Arg Pro Val Leu Trp His Trp Leu Leu Arg Thr Gly
                275                 280                 285

Gly Trp Lys Val Ser Ala Val Thr Leu Ala Tyr Leu Ile Phe Cys Leu
                290                 295                 300

Cys Ser Leu Val Gly Ile Leu His Leu Gln Arg Ala Leu Val Leu Arg
305                 310                 315                 320

Arg Lys Arg

<210> SEQ ID NO 30
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 30

Gly Gly Ser Thr Ser Glu Gly Arg Gly Ser Leu Leu Thr Cys Gly Asp
 1               5                  10                  15

Val Glu Glu Asn Pro Gly Pro
            20

<210> SEQ ID NO 31
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 31

Asp Ile Gln Met Thr Gln Ser Pro Ile Leu Leu Ser Ala Ser Val Gly
```

```
            1               5                  10                 15
Asp Arg Val Thr Ile Thr Cys Lys Ala Ser Gln Asn Ile Asp Lys Tyr
                20                  25                 30
Leu Asn Trp Tyr Gln Gln Arg Thr Asn Gly Ser Pro Arg Leu Leu Ile
                35                  40                 45
Tyr Asn Thr Asn Asn Leu Gln Thr Gly Val Pro Ser Arg Phe Ser Gly
                50                  55                 60
Ser Gly Ser Gly Thr Asp Phe Thr Phe Thr Ile Ser Ser Leu Gln Pro
65                  70                  75                 80
Glu Asp Ile Ala Asp Tyr Tyr Cys Leu Gln His Ile Ser Arg Pro Arg
                85                  90                 95
Thr Phe Gly Gln Gly Thr Lys Val Glu Ile Lys Arg Thr Val Ala Ala
                100                 105                110
Pro Ser Val Phe Ile Phe Pro Pro Ser Asp Glu Gln Leu Lys Ser Gly
                115                 120                125
Thr Ala Ser Val Val Cys Leu Leu Asn Asn Phe Tyr Pro Arg Glu Ala
                130                 135                140
Lys Val Gln Trp Lys Val Asp Asn Ala Leu Gln Ser Gly Asn Ser Gln
145                 150                 155                160
Glu Ser Val Thr Glu Gln Asp Ser Lys Asp Ser Thr Tyr Ser Leu Ser
                165                 170                175
Ser Thr Leu Thr Leu Ser Lys Ala Asp Tyr Glu Lys His Lys Val Tyr
                180                 185                190
Ala Cys Glu Val Thr His Gln Gly Leu Ser Ser Pro Val Thr Lys Ser
                195                 200                205
Phe Asn Arg Gly Glu Cys
210

<210> SEQ ID NO 32
<211> LENGTH: 220
<212> TYPE: PRT
<213> ORGANISM: Artificial Sequence
<220> FEATURE:
<223> OTHER INFORMATION: Synthetic polypeptide

<400> SEQUENCE: 32

Gln Val Gln Leu Gln Glu Ser Gly Gly Gly Leu Val Arg Pro Ser Gln
1               5                   10                 15
Thr Leu Ser Leu Thr Cys Thr Val Ser Gly Phe Thr Phe Thr Asp Phe
                20                  25                 30
Tyr Met Asn Trp Val Arg Gln Ser Pro Gly Arg Gly Leu Glu Trp Ile
                35                  40                 45
Gly Phe Ile Arg Asp Lys Ala Lys Gly Tyr Thr Thr Glu Tyr Asn Pro
                50                  55                 60
Ser Val Lys Gly Arg Val Thr Met Leu Val Asp Thr Ser Lys Asn Gln
65                  70                  75                 80
Phe Ser Leu Arg Leu Ser Ser Val Thr Ala Ala Asp Thr Ala Ile Tyr
                85                  90                 95
Tyr Cys Ala Arg Glu Gly His Thr Ala Ala Pro Phe Asp Tyr Trp Gly
                100                 105                110
Gln Gly Ser Leu Val Thr Val Ser Ala Ser Thr Lys Gly Pro Ser
                115                 120                125
Val Phe Pro Leu Ala Pro Ser Ser Lys Ser Thr Ser Gly Gly Thr Ala
                130                 135                140
Ala Leu Gly Cys Leu Val Lys Asp Tyr Phe Pro Glu Pro Val Thr Val
```

```
145                 150                 155                 160
Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Val Glu
    210                 215                 220

<210> SEQ ID NO 33
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 33

Asp Ile Gln Met Thr Gln Ser Pro Ile Leu Leu Ser Ala Ser Val Gly
1               5                   10                  15

Asp Arg Val Thr Ile Thr Cys Lys Ala Ser Gln Asn Ile Asp Lys Tyr
                20                  25                  30

Leu Asn Trp Tyr Gln Gln Arg Thr Asn Gly Ser Pro Arg Leu Leu Ile
            35                  40                  45

Tyr Asn Thr Asn Asn Leu Gln Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Glu Ala Asp Tyr Tyr Cys Leu Gln His Ile Ser Arg Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 34
<211> LENGTH: 220
<212> TYPE: PRT
<213> ORGANISM: Artificial Sequence
<220> FEATURE:
<223> OTHER INFORMATION: Synthetic polypeptide

<400> SEQUENCE: 34

Gln Val Gln Leu Gln Glu Ser Gly Gly Gly Leu Val Arg Pro Ser Gln
1               5                   10                  15
```

```
Thr Leu Ser Leu Thr Cys Thr Val Ser Gly Phe Thr Phe Thr Asp Phe
            20                  25                  30

Tyr Met Asn Trp Val Arg Gln Ser Pro Gly Arg Gly Leu Glu Trp Ile
        35                  40                  45

Gly Phe Ile Arg Asp Lys Ala Lys Gly Tyr Thr Thr Glu Tyr Asn Pro
    50                  55                  60

Ser Val Lys Gly Arg Val Thr Met Leu Val Asp Thr Ser Lys Asn Gln
65                  70                  75                  80

Phe Ser Leu Arg Leu Ser Ser Val Thr Ala Ala Asp Thr Ala Ile Tyr
                85                  90                  95

Tyr Cys Ala Arg Glu Gly His Thr Ala Ala Pro Phe Asp Tyr Trp Gly
            100                 105                 110

Gln Gly Ser Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu
    210                 215                 220

<210> SEQ ID NO 35
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 35

Asp Ile Gln Met Thr Gln Ser Pro Ile Leu Leu Ser Ala Ser Val Gly
1               5                   10                  15

Asp Arg Val Thr Ile Thr Cys Arg Ala Ser Arg Asp Ile Lys Ser Tyr
            20                  25                  30

Leu Asn Trp Tyr Gln Gln Arg Thr Asn Gly Ser Pro Arg Leu Leu Ile
        35                  40                  45

Tyr Tyr Ala Thr Ser Leu Ala Glu Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Ile Ala Asp Tyr Tyr Cys Leu Gln His Gly Glu Ser Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 36
<211> LENGTH: 225
<212> TYPE: PRT
<213> ORGANISM: Artificial Sequence
<220> FEATURE:
<223> OTHER INFORMATION: Synthetic polypeptide

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Glu Tyr
            20                  25                  30

Tyr Met His Trp Val Arg Gln Ser Pro Gly Lys Gly Leu Glu Trp Val
        35                  40                  45

Gly Leu Ile Asp Pro Glu Gln Gly Asn Thr Ile Tyr Asp Pro Lys Phe
    50                  55                  60

Gln Asp Arg Ala Thr Ile Ser Ala Asp Asn Ser Lys Asn Thr Ala Tyr
65                  70                  75                  80

Leu Gln Met Asn Ser Leu Arg Ala Glu Asp Thr Ala Ile Tyr Tyr Cys
                85                  90                  95

Ala Arg Asp Thr Ala Ala Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr
225

<210> SEQ ID NO 37
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 37

Asp Ile Gln Met Thr Gln Ser Pro Ile Leu Leu Ser Ala Ser Val Gly
1               5                   10                  15
```

Asp Arg Val Thr Ile Thr Cys Arg Ala Ser Arg Asp Ile Lys Ser Tyr
            20                  25                  30

Leu Asn Trp Tyr Gln Gln Arg Thr Asn Gly Ser Pro Arg Leu Leu Ile
        35                  40                  45

Tyr Tyr Ala Thr Ser Leu Ala Glu Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Glu Ala Asp Tyr Tyr Cys Leu Gln His Gly Glu Ser Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 38
<211> LENGTH: 225
<212> TYPE: PRT
<213> ORGANISM: Artificial Sequence
<220> FEATURE:
<223> OTHER INFORMATION: Synthetic polypeptide

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Glu Tyr
            20                  25                  30

Tyr Met His Trp Val Arg Gln Ser Pro Gly Lys Gly Leu Glu Trp Val
        35                  40                  45

Gly Leu Ile Asp Pro Glu Gln Gly Asn Thr Ile Tyr Asp Pro Lys Phe
50                  55                  60

Gln Asp Arg Ala Thr Ile Ser Ala Asp Asn Ser Lys Asn Thr Ala Tyr
65                  70                  75                  80

Leu Gln Met Asn Ser Leu Arg Ala Glu Asp Thr Ala Ile Tyr Tyr Cys
                85                  90                  95

Ala Arg Asp Thr Ala Ala Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

US 9,574,014 B2

135                                                               136
-continued

```
Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
    210                 215                 220

Thr
225

<210> SEQ ID NO 39
<211> LENGTH: 213
<212> TYPE: PRT
<213> ORGANISM: Artificial Sequence
<220> FEATURE:
<223> OTHER INFORMATION: Synthetic polypeptide

<400> SEQUENCE: 39

Glu Ile Val Leu Thr Gln Ser Pro Ile Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Arg Thr Asn Gly Ser Pro Arg Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ile Ala Asp Tyr Phe Cys His Gln Trp Arg Ser Asn Pro Tyr Thr
                85                  90                  95

Phe Gly Gly Gly Thr Lys Leu Glu Ile Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Glu Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 40
<211> LENGTH: 215
<212> TYPE: PRT
<213> ORGANISM: Artificial Sequence
<220> FEATURE:
<223> OTHER INFORMATION: Synthetic polypeptide

<400> SEQUENCE: 40

Glu Val Gln Leu Gln Gln Ser Gly Gly Glu Leu Val Lys Pro Gly Ser
```

```
  1               5                  10                 15
Ser Val Lys Ile Ser Cys Lys Ala Ser Arg Asn Thr Phe Thr Asp Tyr
                20                  25                 30
Asn Leu Asp Trp Val Lys Gln Ser His Gly Lys Thr Leu Glu Trp Ile
                35                  40                 45
Gly Asn Val Tyr Pro Asn Asn Gly Val Thr Gly Tyr Asn Gln Lys Phe
                50                  55                 60
Arg Gly Lys Ala Thr Leu Thr Val Asp Lys Ser Ser Thr Ala Tyr
 65                 70                  75                 80
Met Glu Leu His Ser Leu Thr Ser Glu Asp Ser Ala Ile Tyr Tyr Cys
                85                  90                 95
Ala Leu Tyr Tyr Tyr Asp Val Ser Tyr Trp Gly Gln Gly Thr Leu Val
               100                 105                110
Thr Val Ser Ser Ala Lys Thr Thr Pro Pro Ser Val Tyr Pro Leu Ala
               115                 120                125
Pro Gly Ser Ala Ala Gln Thr Ser Met Val Thr Leu Gly Cys Leu Val
               130                 135                140
Lys Gly Tyr Phe Pro Glu Pro Val Thr Val Thr Trp Asn Ser Gly Ser
145                 150                 155                160
Leu Ser Ser Gly Val His Thr Phe Pro Ala Val Leu Gln Ser Asp Leu
               165                 170                175
Tyr Thr Leu Ser Ser Ser Val Thr Val Pro Ser Ser Thr Trp Pro Ser
               180                 185                190
Gln Ser Val Thr Cys Asn Val Ala His Pro Ala Ser Ser Thr Lys Val
               195                 200                205
Asp Lys Lys Ile Thr Pro Arg
               210                 215

<210> SEQ ID NO 41
<211> LENGTH: 213
<212> TYPE: PRT
<213> ORGANISM: Artificial Sequence
<220> FEATURE:
<223> OTHER INFORMATION: Synthetic polypeptide

<400> SEQUENCE: 41

Glu Ile Val Leu Thr Gln Ser Pro Ile Met Ser Ala Ser Pro Gly
 1              5                   10                 15
Glu Lys Val Thr Met Thr Cys Ser Ala Ser Ser Ser Val Ser Tyr Met
                20                  25                 30
His Trp Tyr Gln Gln Arg Thr Asn Gly Ser Pro Arg Arg Trp Ile Tyr
                35                  40                 45
Asp Thr Ser Lys Leu Ala Ser Gly Val Pro Ala Arg Phe Ser Gly Ser
                50                  55                 60
Gly Ser Gly Thr Ser Tyr Ser Leu Thr Ile Ser Ser Met Glu Ala Glu
 65                 70                  75                 80
Asp Glu Ala Asp Tyr Phe Cys His Gln Trp Arg Ser Asn Pro Tyr Thr
                85                  90                 95
Phe Gly Gly Gly Thr Lys Leu Glu Ile Lys Arg Ala Asp Ala Ala Pro
               100                 105                110
Thr Val Ser Ile Phe Pro Pro Ser Ser Glu Gln Leu Thr Ser Gly Gly
               115                 120                125
Ala Ser Val Val Cys Phe Leu Asn Asn Phe Tyr Pro Lys Glu Ile Asn
               130                 135                140
Val Lys Trp Lys Ile Asp Gly Ser Glu Arg Gln Asn Gly Val Leu Asn
```

```
                145                 150                 155                 160
Ser Trp Thr Asp Gln Asp Ser Lys Asp Ser Thr Tyr Ser Met Ser Ser
                    165                 170                 175

Thr Leu Thr Leu Thr Lys Asp Glu Tyr Glu Arg His Asn Ser Tyr Thr
                    180                 185                 190

Cys Glu Ala Thr His Lys Thr Ser Thr Ser Pro Ile Val Lys Ser Phe
                    195                 200                 205

Asn Arg Asn Glu Cys
            210

<210> SEQ ID NO 42
<211> LENGTH: 215
<212> TYPE: PRT
<213> ORGANISM: Artificial Sequence
<220> FEATURE:
<223> OTHER INFORMATION: Synthetic polypeptide

<400> SEQUENCE: 42

Glu Val Gln Leu Gln Gln Ser Gly Gly Glu Leu Val Lys Pro Gly Ser
1               5                   10                  15

Ser Val Lys Ile Ser Cys Lys Ala Ser Arg Asn Thr Phe Thr Asp Tyr
                20                  25                  30

Asn Leu Asp Trp Val Lys Gln Ser His Gly Lys Thr Leu Glu Trp Ile
            35                  40                  45

Gly Asn Val Tyr Pro Asn Asn Gly Val Thr Gly Tyr Asn Gln Lys Phe
        50                  55                  60

Arg Gly Lys Ala Thr Leu Thr Val Asp Lys Ser Ser Ser Thr Ala Tyr
65                  70                  75                  80

Met Glu Leu His Ser Leu Thr Ser Glu Asp Ser Ala Ile Tyr Tyr Cys
                85                  90                  95

Ala Leu Tyr Tyr Tyr Asp Val Ser Tyr Trp Gly Gln Gly Thr Leu Val
                100                 105                 110

Thr Val Ser Ser Ala Lys Thr Thr Pro Pro Ser Val Tyr Pro Leu Ala
                115                 120                 125

Pro Gly Ser Ala Ala Gln Thr Ser Met Val Thr Leu Gly Cys Leu Val
            130                 135                 140

Lys Gly Tyr Phe Pro Glu Pro Val Thr Val Thr Trp Asn Ser Gly Ser
145                 150                 155                 160

Leu Ser Ser Gly Val His Thr Phe Pro Ala Val Leu Gln Ser Asp Leu
                165                 170                 175

Tyr Thr Leu Ser Ser Ser Val Thr Val Pro Ser Ser Thr Trp Pro Ser
                180                 185                 190

Gln Ser Val Thr Cys Asn Val Ala His Pro Ala Ser Ser Thr Lys Val
                195                 200                 205

Asp Lys Lys Ile Thr Pro Arg
            210                 215

<210> SEQ ID NO 43
<211> LENGTH: 213
<212> TYPE: PRT
<213> ORGANISM: Artificial Sequence
<220> FEATURE:
<223> OTHER INFORMATION: Synthetic polypeptide

<400> SEQUENCE: 43

Asp Ile Gln Met Thr Gln Ser Pro Ile Leu Leu Ser Ala Ser Val Gly
1               5                   10                  15
```

Asp Arg Val Thr Ile Thr Cys Ser Ala Ser Ser Ser Ile Ser Tyr Met
            20                  25                  30

His Trp Tyr Gln Gln Arg Thr Asn Gly Ser Pro Arg Leu Leu Ile Tyr
        35                  40                  45

Thr Thr Ser Asn Leu Ala Ser Gly Val Pro Ala Arg Phe Ser Gly Ser
    50                  55                  60

Gly Ser Gly Thr Glu Phe Thr Leu Thr Ile Ser Ser Leu Gln Pro Asp
65                  70                  75                  80

Asp Ile Ala Asp Tyr Tyr Cys His Gln Arg Ser Thr Tyr Pro Leu Thr
                85                  90                  95

Phe Gly Gln Gly Thr Lys Val Glu Val Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 44
<211> LENGTH: 216
<212> TYPE: PRT
<213> ORGANISM: Artificial Sequence
<220> FEATURE:
<223> OTHER INFORMATION: Synthetic polypeptide

<400> SEQUENCE: 44

Gln Val Gln Leu Val Gln Ser Gly Gly Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Arg Met His Trp Val Arg Gln Ser Pro Gly Gln Gly Leu Glu Trp Ile
        35                  40                  45

Gly Tyr Ile Asn Pro Ser Thr Gly Tyr Thr Glu Tyr Asn Gln Lys Phe
    50                  55                  60

Lys Asp Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Ile Tyr Tyr Cys
                85                  90                  95

Ala Arg Gly Gly Gly Val Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
             165                 170                 175

Gly Leu Tyr Ser Leu Ser Ser Val Val Thr Val Pro Ser Ser Ser Leu
         180                 185                 190

Gly Thr Gln Thr Tyr Ile Cys Asn Val Asn His Lys Pro Ser Asn Thr
     195                 200                 205

Lys Val Asp Lys Lys Val Glu Pro
 210                 215

<210> SEQ ID NO 45
<211> LENGTH: 213
<212> TYPE: PRT
<213> ORGANISM: Artificial Sequence
<220> FEATURE:
<223> OTHER INFORMATION: Synthetic polypeptide

<400> SEQUENCE: 45

Asp Ile Gln Met Thr Gln Ser Pro Ile Leu Leu Ser Ala Ser Val Gly
1               5                   10                  15

Asp Arg Val Thr Ile Thr Cys Ser Ala Ser Ser Ser Ile Ser Tyr Met
             20                  25                  30

His Trp Tyr Gln Gln Arg Thr Asn Gly Ser Pro Arg Leu Leu Ile Tyr
         35                  40                  45

Thr Thr Ser Asn Leu Ala Ser Gly Val Pro Ala Arg Phe Ser Gly Ser
     50                  55                  60

Gly Ser Gly Thr Glu Phe Thr Leu Thr Ile Ser Ser Leu Gln Pro Asp
65                  70                  75                  80

Asp Glu Ala Asp Tyr Tyr Cys His Gln Arg Ser Thr Tyr Pro Leu Thr
                 85                  90                  95

Phe Gly Gln Gly Thr Lys Val Glu Val Lys Arg Thr Val Ala Ala Pro
             100                 105                 110

Ser Val Phe Ile Phe Pro Pro Ser Asp Glu Gln Leu Lys Ser Gly Thr
         115                 120                 125

Ala Ser Val Val Cys Leu Leu Asn Asn Phe Tyr Pro Arg Glu Ala Lys
     130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                 165                 170                 175

Thr Leu Thr Leu Ser Lys Ala Asp Tyr Glu Lys His Lys Val Tyr Ala
             180                 185                 190

Cys Glu Val Thr His Gln Gly Leu Ser Ser Pro Val Thr Lys Ser Phe
         195                 200                 205

Asn Arg Gly Glu Cys
     210

<210> SEQ ID NO 46
<211> LENGTH: 216
<212> TYPE: PRT
<213> ORGANISM: Artificial Sequence
<220> FEATURE:
<223> OTHER INFORMATION: Synthetic polypeptide

<400> SEQUENCE: 46

Gln Val Gln Leu Val Gln Ser Gly Gly Glu Val Lys Lys Pro Gly Ser
1               5                   10                  15

Ser Val Lys Val Ser Cys Lys Ala Ser Gly Tyr Thr Phe Thr Ser Tyr
             20                  25                  30

```
Arg Met His Trp Val Arg Gln Ser Pro Gly Gln Gly Leu Glu Trp Ile
        35                  40                  45

Gly Tyr Ile Asn Pro Ser Thr Gly Tyr Thr Glu Tyr Asn Gln Lys Phe
 50                  55                  60

Lys Asp Lys Ala Thr Ile Thr Ala Asp Glu Ser Thr Asn Thr Ala Tyr
65                   70                  75                  80

Met Glu Leu Ser Ser Leu Arg Ser Glu Asp Thr Ala Ile Tyr Tyr Cys
                85                  90                  95

Ala Arg Gly Gly Gly Val Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro
    210                 215

<210> SEQ ID NO 47
<211> LENGTH: 213
<212> TYPE: PRT
<213> ORGANISM: Artificial Sequence
<220> FEATURE:
<223> OTHER INFORMATION: Synthetic polypeptide

<400> SEQUENCE: 47

Asp Ile Glu Leu Thr Gln Ser Pro Ile Ile Met Ser Ala Ser Pro Gly
1               5                   10                  15

Glu Lys Val Thr Met Thr Cys Ser Ala Ser Ser Ser Val Ser Tyr Met
                20                  25                  30

His Trp Tyr Gln Gln Arg Thr Asn Gly Ser Pro Arg Arg Trp Ile Tyr
            35                  40                  45

Asp Thr Ser Lys Leu Ala Ser Gly Val Pro Gly Arg Phe Ser Gly Ser
 50                  55                  60

Gly Ser Gly Asn Ser Tyr Ser Leu Thr Ile Ser Ser Val Glu Ala Glu
65                   70                  75                  80

Asp Ile Ala Asp Tyr Tyr Cys Gln Gln Trp Ser Lys His Pro Leu Thr
                85                  90                  95

Phe Gly Ser Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175
```

```
Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 48
<211> LENGTH: 231
<212> TYPE: PRT
<213> ORGANISM: Artificial Sequence
<220> FEATURE:
<223> OTHER INFORMATION: Synthetic polypeptide

<400> SEQUENCE: 48

Glu Val Gln Leu Gln Gln Ser Gly Gly Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Thr Met Asn Trp Val Lys Gln Ser His Gly Lys Ser Leu Glu Trp Ile
        35                  40                  45

Gly Leu Ile Thr Pro Tyr Asn Gly Ala Ser Ser Tyr Asn Gln Lys Phe
    50                  55                  60

Arg Gly Lys Ala Thr Leu Thr Val Asp Lys Ser Ser Ser Thr Ala Tyr
65                  70                  75                  80

Met Asp Leu Leu Ser Leu Thr Ser Glu Asp Ser Ala Ile Tyr Phe Cys
                85                  90                  95

Ala Arg Gly Gly Tyr Asp Gly Arg Gly Phe Asp Tyr Trp Gly Ser Gly
            100                 105                 110

Thr Pro Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys
225                 230

<210> SEQ ID NO 49
<211> LENGTH: 213
<212> TYPE: PRT
<213> ORGANISM: Artificial Sequence
<220> FEATURE:
<223> OTHER INFORMATION: Synthetic polypeptide

<400> SEQUENCE: 49

Asp Ile Glu Leu Thr Gln Ser Pro Ile Ile Met Ser Ala Ser Pro Gly
1               5                   10                  15

Glu Lys Val Thr Met Thr Cys Ser Ala Ser Ser Ser Val Ser Tyr Met
```

```
                 20                  25                  30
His Trp Tyr Gln Gln Arg Thr Asn Gly Ser Pro Arg Arg Trp Ile Tyr
             35                  40                  45

Asp Thr Ser Lys Leu Ala Ser Gly Val Pro Gly Arg Phe Ser Gly Ser
         50                  55                  60

Gly Ser Gly Asn Ser Tyr Ser Leu Thr Ile Ser Ser Val Glu Ala Glu
65                  70                  75                  80

Asp Glu Ala Asp Tyr Tyr Cys Gln Gln Trp Ser Lys His Pro Leu Thr
                 85                  90                  95

Phe Gly Ser Gly Thr Lys Val Glu Ile Lys Arg Thr Val Ala Ala Pro
             100                 105                 110

Ser Val Phe Ile Phe Pro Pro Ser Asp Glu Gln Leu Lys Ser Gly Thr
         115                 120                 125

Ala Ser Val Val Cys Leu Leu Asn Asn Phe Tyr Pro Arg Glu Ala Lys
     130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                 165                 170                 175

Thr Leu Thr Leu Ser Lys Ala Asp Tyr Glu Lys His Lys Val Tyr Ala
             180                 185                 190

Cys Glu Val Thr His Gln Gly Leu Ser Ser Pro Val Thr Lys Ser Phe
         195                 200                 205

Asn Arg Gly Glu Cys
     210

<210> SEQ ID NO 50
<211> LENGTH: 231
<212> TYPE: PRT
<213> ORGANISM: Artificial Sequence
<220> FEATURE:
<223> OTHER INFORMATION: Synthetic polypeptide

<400> SEQUENCE: 50

Glu Val Gln Leu Gln Gln Ser Gly Gly Glu Leu Glu Lys Pro Gly Ala
1               5                   10                  15

Ser Val Lys Ile Ser Cys Lys Ala Ser Gly Tyr Ser Phe Thr Gly Tyr
             20                  25                  30

Thr Met Asn Trp Val Lys Gln Ser His Gly Lys Ser Leu Glu Trp Ile
         35                  40                  45

Gly Leu Ile Thr Pro Tyr Asn Gly Ala Ser Ser Tyr Asn Gln Lys Phe
     50                  55                  60

Arg Gly Lys Ala Thr Leu Thr Val Asp Lys Ser Ser Ser Thr Ala Tyr
65                  70                  75                  80

Met Asp Leu Leu Ser Leu Thr Ser Glu Asp Ser Ala Ile Tyr Phe Cys
                 85                  90                  95

Ala Arg Gly Gly Tyr Asp Gly Arg Gly Phe Asp Tyr Trp Gly Ser Gly
             100                 105                 110

Thr Pro Val Thr Val Ser Ser Ala Ser Thr Lys Gly Pro Ser Val Phe
         115                 120                 125

Pro Leu Ala Pro Ser Ser Lys Ser Thr Ser Gly Gly Thr Ala Ala Leu
     130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
```

165                 170                 175
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Val Glu Pro Lys Ser Cys Asp Lys
        210                 215                 220

Thr His Thr Cys Pro Pro Cys
225                 230

<210> SEQ ID NO 51
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 51

Glu Ile Val Leu Thr Gln Ser Pro Ile Leu Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Arg Thr Asn Gly Ser Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Ile Ala Asp Tyr Tyr Cys Gln Gln Arg Ser Asn Trp Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 52
<211> LENGTH: 222
<212> TYPE: PRT
<213> ORGANISM: Artificial Sequence
<220> FEATURE:
<223> OTHER INFORMATION: Synthetic polypeptide

<400> SEQUENCE: 52

Glu Val Gln Leu Val Glu Ser Gly Gly Gly Leu Val Gln Pro Gly Arg
1               5                   10                  15

```
Ser Leu Arg Leu Ser Cys Ala Ala Ser Gly Phe Thr Phe Asn Asp Tyr
            20                  25                  30

Ala Met His Trp Val Arg Gln Ser Pro Gly Lys Gly Leu Glu Trp Val
        35                  40                  45

Ser Thr Ile Ser Trp Asn Ser Gly Ser Ile Gly Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Ile Tyr Tyr Cys
                85                  90                  95

Ala Lys Asp Ile Gln Tyr Gly Asn Tyr Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Gly Ser Ser Lys Ser Thr Ser Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro
    210                 215                 220

<210> SEQ ID NO 53
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 53

Glu Ile Val Leu Thr Gln Ser Pro Ile Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Arg Thr Asn Gly Ser Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Ile Ala Asp Tyr Tyr Cys Gln Gln Arg Ser Asn Trp Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 54
<211> LENGTH: 222
<212> TYPE: PRT
<213> ORGANISM: Artificial Sequence
<220> FEATURE:
<223> OTHER INFORMATION: Synthetic polypeptide

<400> SEQUENCE: 54

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
            20                  25                  30

Ala Met His Trp Val Arg Gln Ser Pro Gly Lys Gly Leu Glu Trp Val
        35                  40                  45

Ser Thr Ile Ser Trp Asn Ser Gly Ser Ile Gly Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Ile Tyr Tyr Cys
                85                  90                  95

Ala Lys Asp Ile Gln Tyr Gly Asn Tyr Tyr Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Gly Ser Ser Lys Ser Thr Ser Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro
    210                 215                 220

<210> SEQ ID NO 55
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 55

Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Ser Thr Ala
            20                  25                  30

-continued

Val Ala Trp Tyr Gln Gln Arg Thr Asn Gly Ser Pro Arg Leu Leu Ile
                35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Asp Tyr Tyr Cys Gln Gln Phe Tyr Thr Thr Pro Ser
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210

<210> SEQ ID NO 56
<211> LENGTH: 227
<212> TYPE: PRT
<213> ORGANISM: Artificial Sequence
<220> FEATURE:
<223> OTHER INFORMATION: Synthetic polypeptide

<400> SEQUENCE: 56

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Ile His Trp Val Arg Gln Ser Pro Gly Lys Gly Leu Glu Trp Val
        35                  40                  45

Ala Arg Ile Asn Pro Pro Asn Arg Ser Asn Gln Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Ile Tyr Tyr Cys
                85                  90                  95

Ala Arg Gly Ser Gly Phe Arg Trp Val Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr
225

<210> SEQ ID NO 57
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 57

Asp Ile Gln Met Thr Gln Ser Pro Ile Leu Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Arg Thr Asn Gly Ser Pro Arg Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Glu Ala Asp Tyr Tyr Cys Gln Gln Phe Tyr Thr Thr Pro Ser
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 58
<211> LENGTH: 227
<212> TYPE: PRT
<213> ORGANISM: Artificial Sequence
<220> FEATURE:
<223> OTHER INFORMATION: Synthetic polypeptide

<400> SEQUENCE: 58

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr

```
            20                  25                  30
Trp Ile His Trp Val Arg Gln Ser Pro Gly Lys Gly Leu Glu Trp Val
            35                  40                  45
Ala Arg Ile Asn Pro Asn Arg Ser Asn Gln Tyr Ala Asp Ser Val
        50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Ile Tyr Tyr Cys
                85                  90                  95
Ala Arg Gly Ser Gly Phe Arg Trp Val Met Asp Tyr Trp Gly Gln Gly
            100                 105                 110
Thr Leu Val Thr Val Ser Ser Ala Ser Thr Lys Gly Pro Ser Val Phe
            115                 120                 125
Pro Leu Ala Pro Ser Ser Lys Ser Thr Ser Gly Gly Thr Ala Ala Leu
        130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
            195                 200                 205
Ser Asn Thr Lys Val Asp Lys Lys Val Glu Pro Lys Ser Cys Asp Lys
        210                 215                 220
Thr His Thr
225

<210> SEQ ID NO 59
<211> LENGTH: 220
<212> TYPE: PRT
<213> ORGANISM: Artificial Sequence
<220> FEATURE:
<223> OTHER INFORMATION: Synthetic polypeptide

<400> SEQUENCE: 59

Asp Ile Val Met Thr Gln Ser Pro Ile Leu Leu Ala Val Ser Leu Gly
1               5                   10                  15
Glu Arg Ala Thr Ile Asn Cys Lys Ser Ser Gln Ser Val Leu Asn Ser
            20                  25                  30
Gly Asn Gln Lys Asn Tyr Leu Thr Trp Tyr Gln Gln Arg Thr Asn Gly
        35                  40                  45
Ser Pro Arg Leu Leu Ile Tyr Trp Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Ile Ala Asp Tyr Tyr Cys Gln Ser
                85                  90                  95
Asp Tyr Ser Tyr Pro Tyr Thr Phe Gly Gln Gly Thr Lys Leu Glu Ile
            100                 105                 110
Lys Arg Thr Val Ala Ala Pro Ser Val Phe Ile Phe Pro Pro Ser Asp
        115                 120                 125
Glu Gln Leu Lys Ser Gly Thr Ala Ser Val Val Cys Leu Leu Asn Asn
    130                 135                 140
Phe Tyr Pro Arg Glu Ala Lys Val Gln Trp Lys Val Asp Asn Ala Leu
```

```
                145                 150                 155                 160
Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
                195                 200                 205

Ser Pro Val Thr Lys Ser Phe Asn Arg Gly Glu Cys
                210                 215                 220

<210> SEQ ID NO 60
<211> LENGTH: 227
<212> TYPE: PRT
<213> ORGANISM: Artificial Sequence
<220> FEATURE:
<223> OTHER INFORMATION: Synthetic polypeptide

<400> SEQUENCE: 60

Gln Val Gln Leu Val Gln Ser Gly Gly Val Lys Lys Pro Gly Ala
1               5                   10                  15

Ser Val Lys Val Ser Cys Lys Ala Ser Gly Tyr Thr Phe Arg Ser Ser
                20                  25                  30

Tyr Ile Ser Trp Val Arg Gln Ser Pro Gly Gln Gly Leu Glu Trp Met
            35                  40                  45

Gly Trp Ile Tyr Ala Gly Thr Gly Ser Pro Ser Tyr Asn Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Ile Tyr Tyr Cys
                85                  90                  95

Ala Arg His Arg Asp Tyr Tyr Ser Asn Ser Leu Thr Tyr Trp Gly Gln
                100                 105                 110

Gly Thr Leu Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
                130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
                210                 215                 220

Lys Thr His
225

<210> SEQ ID NO 61
<211> LENGTH: 220
<212> TYPE: PRT
<213> ORGANISM: Artificial Sequence
<220> FEATURE:
<223> OTHER INFORMATION: Synthetic polypeptide

<400> SEQUENCE: 61
```

-continued

Asp Ile Val Met Thr Gln Ser Pro Ile Leu Leu Ala Val Ser Leu Gly
1               5                   10                  15

Glu Arg Ala Thr Ile Asn Cys Lys Ser Ser Gln Ser Val Leu Asn Ser
            20                  25                  30

Gly Asn Gln Lys Asn Tyr Leu Thr Trp Tyr Gln Gln Arg Thr Asn Gly
        35                  40                  45

Ser Pro Arg Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Glu Ala Asp Tyr Tyr Cys Gln Ser
                85                  90                  95

Asp Tyr Ser Tyr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 62
<211> LENGTH: 227
<212> TYPE: PRT
<213> ORGANISM: Artificial Sequence
<220> FEATURE:
<223> OTHER INFORMATION: Synthetic polypeptide

<400> SEQUENCE: 62

Gln Val Gln Leu Val Gln Ser Gly Gly Gly Val Lys Lys Pro Gly Ala
1               5                   10                  15

Ser Val Lys Val Ser Cys Lys Ala Ser Gly Tyr Thr Phe Arg Ser Ser
            20                  25                  30

Tyr Ile Ser Trp Val Arg Gln Ser Pro Gly Gln Gly Leu Glu Trp Met
        35                  40                  45

Gly Trp Ile Tyr Ala Gly Thr Gly Ser Pro Ser Tyr Asn Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Ile Tyr Tyr Cys
                85                  90                  95

Ala Arg His Arg Asp Tyr Tyr Ser Asn Ser Leu Thr Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
        210                 215                 220

Lys Thr His
225

<210> SEQ ID NO 63
<211> LENGTH: 213
<212> TYPE: PRT
<213> ORGANISM: Artificial Sequence
<220> FEATURE:
<223> OTHER INFORMATION: Synthetic polypeptide

<400> SEQUENCE: 63

Gln Ile Val Leu Ser Gln Ser Pro Ile Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Arg Thr Asn Gly Ser Pro Arg Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ile Ala Asp Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 64
<211> LENGTH: 224
<212> TYPE: PRT
<213> ORGANISM: Artificial Sequence
<220> FEATURE:
<223> OTHER INFORMATION: Synthetic polypeptide

<400> SEQUENCE: 64
```

-continued

```
Gln Val Gln Leu Gln Gln Pro Gly Gly Leu Val Lys Pro Gly Ala
1               5                   10                  15

Ser Val Lys Met Ser Cys Lys Ala Ser Gly Tyr Thr Phe Thr Ser Tyr
                20                  25                  30

Asn Met His Trp Val Lys Gln Thr Pro Gly Arg Gly Leu Glu Trp Ile
            35                  40                  45

Gly Ala Ile Tyr Pro Gly Asn Gly Asp Thr Ser Tyr Asn Gln Lys Phe
        50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Ile Tyr Tyr Cys
                85                  90                  95

Ala Arg Ser Thr Tyr Tyr Gly Gly Asp Trp Tyr Phe Asn Val Trp Gly
                100                 105                 110

Ala Gly Thr Thr Val Thr Val Ser Ala Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220
```

<210> SEQ ID NO 65
<211> LENGTH: 213
<212> TYPE: PRT
<213> ORGANISM: Artificial Sequence
<220> FEATURE:
<223> OTHER INFORMATION: Synthetic polypeptide

<400> SEQUENCE: 65

```
Gln Ile Val Leu Ser Gln Ser Pro Ile Ile Leu Ser Ala Ser Pro Gly
1               5                   10                  15

Glu Lys Val Thr Met Thr Cys Arg Ala Ser Ser Ser Val Ser Tyr Ile
                20                  25                  30

His Trp Phe Gln Gln Arg Thr Asn Gly Ser Pro Arg Pro Trp Ile Tyr
            35                  40                  45

Ala Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Val Glu Ala Glu
65                  70                  75                  80

Asp Glu Ala Asp Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140
```

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 66
<211> LENGTH: 224
<212> TYPE: PRT
<213> ORGANISM: Artificial Sequence
<220> FEATURE:
<223> OTHER INFORMATION: Synthetic polypeptide

<400> SEQUENCE: 66

Gln Val Gln Leu Gln Gln Pro Gly Gly Gly Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Ile Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

<210> SEQ ID NO 67
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 67

Tyr Ile Gln Met Thr Gln Ser Pro Ile Leu Leu Ser Val Ser Val Gly

```
             1               5                  10                 15
           Glu Thr Val Thr Ile Thr Cys Arg Ala Ser Glu Asn Ile Tyr Ser Phe
                           20                  25                 30
           Leu Ala Trp Tyr Gln Gln Arg Thr Asn Gly Ser Pro Arg Leu Leu Val
                           35                  40                 45
           Tyr Ala Ala Thr Asn Leu Ala Asp Gly Val Pro Ser Arg Phe Ser Gly
                           50                  55                 60
           Ser Gly Ser Gly Thr Gln Phe Ser Leu Lys Ile Asn Ser Leu Gln Ser
           65                              70                  75              80
           Glu Asp Ile Ala Asp Tyr Tyr Cys Gln His Phe Trp Gly Thr Pro Phe
                           85                  90                 95
           Thr Phe Gly Ser Gly Thr Lys Leu Glu Ile Lys Arg Ser Asp Ala Ala
                           100                 105                110
           Pro Thr Val Ser Ile Phe Pro Pro Ser Ala Ala Gln Leu Ser Ser Gly
                           115                 120                125
           Gly Gly Ser Val Val Cys Phe Leu Asn Asn Phe Tyr Pro Lys Asp Ile
           130                             135                 140
           Asn Val Lys Trp Lys Ile Asp Gly Ala Glu Arg Gly Asn Gly Val Leu
           145                             150                 155             160
           Asn Ser Trp Thr Ser Gln Asp Ser Ala Asp Ser Thr Tyr Ser Met Ser
                           165                 170                175
           Ser Thr Leu Thr Ser Gly Gly Asp Glu Tyr Glu Arg His Asn Ser Tyr
                           180                 185                190
           Thr Cys Glu Ala Thr His Lys Thr Ser Thr Pro Ile Val Lys Ser
                           195                 200                205
           Phe Asn Arg Gly Glu Cys
           210

<210> SEQ ID NO 68
<211> LENGTH: 216
<212> TYPE: PRT
<213> ORGANISM: Artificial Sequence
<220> FEATURE:
<223> OTHER INFORMATION: Synthetic polypeptide

<400> SEQUENCE: 68

Glu Val Gln Leu Val Glu Ser Gly Gly Gly Leu Val Gln Pro Lys Gly
           1                5                  10                 15
           Ser Leu Lys Ile Ser Cys Ala Ala Ser Gly Phe Thr Phe Asn Ile Tyr
                           20                  25                 30
           Ala Met Asn Trp Val Arg Gln Ser Pro Gly Lys Gly Leu Glu Trp Val
                           35                  40                 45
           Ala Arg Ile Arg Ser Gln Ser Asn Asn Tyr Thr Thr Tyr Tyr Ala Asp
                           50                  55                 60
           Ser Val Lys Asp Arg Phe Thr Ile Ser Arg Asp Asp Ser Gln Ser Met
           65                              70                  75              80
           Leu Tyr Leu Gln Met Asn Asn Leu Lys Thr Glu Asp Thr Ala Ile Tyr
                           85                  90                 95
           Tyr Cys Val Arg Gln Met Gly Asp Tyr Trp Gly Gln Gly Thr Thr Leu
                           100                 105                110
           Thr Val Ser Ser Ala Val Lys Thr Pro Pro Ser Val Tyr Pro Leu Ala
                           115                 120                125
           Pro Gly Gly Gly Ala Ile Ser Asn Ser Met Val Thr Leu Gly Cys Leu
                           130                 135                140
           Val Asn Gly Tyr Phe Pro Glu Pro Val Thr Val Thr Trp Asn Ala Gly
```

```
                145                 150                 155                 160
Ser Leu Gly Ser Gly Val His Thr Phe Pro Ala Val Leu Gln Ser Asp
                165                 170                 175

Leu Tyr Thr Leu Ser Ser Val Thr Val Pro Val Ser Thr Trp Pro
                180                 185                 190

Ser Glu Ala Val Thr Cys Asn Val Ala His Pro Ala Ser Ala Thr Ser
                195                 200                 205

Val Asp Lys Ala Ile Ser Pro Val
                210                 215

<210> SEQ ID NO 69
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 69

Tyr Ile Gln Met Thr Gln Ser Pro Ile Leu Leu Ser Val Ser Val Gly
1               5                   10                  15

Glu Thr Val Thr Ile Thr Cys Arg Ala Ser Glu Asn Ile Tyr Ser Phe
                20                  25                  30

Leu Ala Trp Tyr Gln Gln Arg Thr Asn Gly Ser Pro Arg Leu Leu Val
            35                  40                  45

Tyr Ala Ala Thr Asn Leu Ala Asp Gly Val Pro Ser Arg Phe Ser Gly
        50                  55                  60

Ser Gly Ser Gly Thr Gln Phe Ser Leu Lys Ile Asn Ser Leu Gln Ser
65                  70                  75                  80

Glu Asp Ile Ala Asp Tyr Tyr Cys Gln His Phe Trp Gly Thr Pro Phe
                85                  90                  95

Thr Phe Gly Ser Gly Thr Lys Leu Glu Ile Lys Arg Ser Asp Ala Ala
                100                 105                 110

Pro Thr Val Ser Ile Phe Pro Pro Ser Ala Ala Gln Leu Ser Ser Gly
            115                 120                 125

Gly Gly Ser Val Val Cys Phe Leu Asn Asn Phe Tyr Pro Lys Asp Ile
        130                 135                 140

Asn Val Lys Trp Lys Ile Asp Gly Ala Glu Arg Gly Asn Gly Val Leu
145                 150                 155                 160

Asn Ser Trp Thr Ser Gln Asp Ser Ala Asp Ser Thr Tyr Ser Met Ser
                165                 170                 175

Ser Thr Leu Thr Ser Gly Gly Asp Glu Tyr Glu Arg His Asn Ser Tyr
                180                 185                 190

Thr Cys Glu Ala Thr His Lys Thr Ser Thr Ser Pro Ile Val Lys Ser
            195                 200                 205

Phe Asn Arg Gly Glu Cys
        210

<210> SEQ ID NO 70
<211> LENGTH: 216
<212> TYPE: PRT
<213> ORGANISM: Artificial Sequence
<220> FEATURE:
<223> OTHER INFORMATION: Synthetic polypeptide

<400> SEQUENCE: 70

Glu Val Gln Leu Val Glu Ser Gly Gly Gly Leu Val Gln Pro Lys Gly
1               5                   10                  15
```

```
Ser Leu Lys Ile Ser Cys Ala Ala Ser Gly Phe Thr Phe Asn Ile Tyr
             20                  25                  30

Ala Met Asn Trp Val Arg Gln Ser Pro Gly Lys Gly Leu Glu Trp Val
         35                  40                  45

Ala Arg Ile Arg Ser Gln Ser Asn Asn Tyr Thr Thr Tyr Tyr Ala Asp
    50                  55                  60

Ser Val Lys Asp Arg Phe Thr Ile Ser Arg Asp Asp Ser Gln Ser Met
 65                  70                  75                  80

Leu Tyr Leu Gln Met Asn Asn Leu Lys Thr Glu Asp Thr Ala Ile Tyr
                 85                  90                  95

Tyr Cys Val Arg Gln Met Gly Asp Tyr Trp Gly Gln Gly Thr Thr Leu
            100                 105                 110

Thr Val Ser Ser Ala Val Lys Thr Pro Pro Ser Val Tyr Pro Leu Ala
        115                 120                 125

Pro Gly Gly Gly Ala Ile Ser Asn Ser Met Val Thr Leu Gly Cys Leu
    130                 135                 140

Val Asn Gly Tyr Phe Pro Glu Pro Val Thr Val Thr Trp Asn Ala Gly
145                 150                 155                 160

Ser Leu Gly Ser Gly Val His Thr Phe Pro Ala Val Leu Gln Ser Asp
                165                 170                 175

Leu Tyr Thr Leu Ser Ser Ser Val Thr Val Pro Val Ser Thr Trp Pro
            180                 185                 190

Ser Glu Ala Val Thr Cys Asn Val Ala His Pro Ala Ser Ala Thr Ser
                195                 200                 205

Val Asp Lys Ala Ile Ser Pro Val
            210                 215

<210> SEQ ID NO 71
<211> LENGTH: 219
<212> TYPE: PRT
<213> ORGANISM: Artificial Sequence
<220> FEATURE:
<223> OTHER INFORMATION: Synthetic polypeptide

<400> SEQUENCE: 71

Asp Val Val Met Thr Gln Thr Pro Leu Leu Leu Ser Val Thr Ile Gly
  1               5                  10                  15

Gln Pro Ala Ser Ile Ser Cys Lys Ser Ser Gln Ser Leu Leu Asp Ser
             20                  25                  30

Asp Gly Lys Thr Tyr Leu Asn Trp Leu Leu Gln Arg Thr Asn Gly Ser
         35                  40                  45

Pro Arg Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Ile Ala Asp Tyr Tyr Cys Trp Gln Gly
                 85                  90                  95

Thr His Phe Pro Leu Thr Phe Gly Ala Gly Thr Lys Leu Glu Leu Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160
```

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 72
<211> LENGTH: 228
<212> TYPE: PRT
<213> ORGANISM: Artificial Sequence
<220> FEATURE:
<223> OTHER INFORMATION: Synthetic polypeptide

<400> SEQUENCE: 72

Glu Val Gln Leu Gln Gln Ser Gly Gly Gly Leu Val Lys Thr Gly Ala
1               5                   10                  15

Ser Val Lys Ile Ser Cys Lys Ala Ser Gly Tyr Ser Phe Thr Ser Tyr
            20                  25                  30

Tyr Met His Trp Val Lys Gln Ser His Gly Lys Ser Leu Glu Trp Ile
        35                  40                  45

Gly Glu Ile Asn Pro Tyr Asn Gly Gly Ala Ser Tyr Asn Gln Lys Ile
    50                  55                  60

Lys Gly Arg Ala Thr Phe Thr Val Asp Thr Ser Ser Arg Thr Ala Tyr
65                  70                  75                  80

Met Gln Phe Asn Ser Leu Thr Ser Glu Asp Ser Ala Ile Tyr Tyr Cys
                85                  90                  95

Ala Arg Ser Ile Tyr Gly His Ser Val Leu Asp Tyr Trp Gly Gln Gly
            100                 105                 110

Thr Ser Val Ser Val Ser Ser Ala Lys Thr Thr Pro Pro Ser Val Tyr
        115                 120                 125

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Pro Ser Ser
            180                 185                 190

Thr Trp Pro Ser Gln Thr Val Thr Cys Asn Val Ala His Pro Ala Ser
        195                 200                 205

Ser Thr Lys Val Asp Lys Lys Ile Val Pro Arg Asp Cys Gly Cys Lys
    210                 215                 220

Pro Cys Ile Cys
225

<210> SEQ ID NO 73
<211> LENGTH: 219
<212> TYPE: PRT
<213> ORGANISM: Artificial Sequence
<220> FEATURE:
<223> OTHER INFORMATION: Synthetic polypeptide

<400> SEQUENCE: 73

Asp Val Val Met Thr Gln Thr Pro Leu Leu Leu Ser Val Thr Ile Gly
1               5                   10                  15

```
Gln Pro Ala Ser Ile Ser Cys Lys Ser Ser Gln Ser Leu Leu Asp Ser
             20                  25                  30

Asp Gly Lys Thr Tyr Leu Asn Trp Leu Leu Gln Arg Thr Asn Gly Ser
         35                  40                  45

Pro Arg Arg Leu Ile Tyr Leu Val Ser Lys Leu Asp Ser Gly Val Pro
     50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Ala Asp Tyr Tyr Cys Trp Gln Gly
                 85                  90                  95

Thr His Phe Pro Leu Thr Phe Gly Ala Gly Thr Lys Leu Glu Leu Lys
                100                 105                 110

Arg Ala Asp Ala Ala Pro Thr Val Ser Ile Phe Pro Pro Ser Ser Glu
            115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 74
<211> LENGTH: 228
<212> TYPE: PRT
<213> ORGANISM: Artificial Sequence
<220> FEATURE:
<223> OTHER INFORMATION: Synthetic polypeptide

<400> SEQUENCE: 74

Glu Val Gln Leu Gln Gln Ser Gly Gly Gly Leu Val Lys Thr Gly Ala
1               5                   10                  15

Ser Val Lys Ile Ser Cys Lys Ala Ser Gly Tyr Ser Phe Thr Ser Tyr
             20                  25                  30

Tyr Met His Trp Val Lys Gln Ser His Gly Lys Ser Leu Glu Trp Ile
         35                  40                  45

Gly Glu Ile Asn Pro Tyr Asn Gly Gly Ala Ser Tyr Asn Gln Lys Ile
     50                  55                  60

Lys Gly Arg Ala Thr Phe Thr Val Asp Thr Ser Arg Thr Ala Tyr
 65                  70                  75                  80

Met Gln Phe Asn Ser Leu Thr Ser Glu Asp Ser Ala Ile Tyr Tyr Cys
                 85                  90                  95

Ala Arg Ser Ile Tyr Gly His Ser Val Leu Asp Tyr Trp Gly Gln Gly
                100                 105                 110

Thr Ser Val Ser Val Ser Ser Ala Lys Thr Thr Pro Pro Ser Val Tyr
            115                 120                 125

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160
```

```
Asn Ser Gly Ser Leu Ser Ser Gly Val His Thr Phe Pro Ala Val Leu
            165                 170                 175

Gln Ser Asp Leu Tyr Thr Leu Ser Ser Val Thr Val Pro Ser Ser
        180                 185                 190

Thr Trp Pro Ser Gln Thr Val Thr Cys Asn Val Ala His Pro Ala Ser
        195                 200                 205

Ser Thr Lys Val Asp Lys Lys Ile Val Pro Arg Asp Cys Gly Cys Lys
    210                 215                 220

Pro Cys Ile Cys
225

<210> SEQ ID NO 75
<211> LENGTH: 215
<212> TYPE: PRT
<213> ORGANISM: Artificial Sequence
<220> FEATURE:
<223> OTHER INFORMATION: Synthetic polypeptide

<400> SEQUENCE: 75

Ile Val Leu Thr Gln Ser Pro Ile Leu Leu Ser Val Ser Pro Gly Glu
1               5                   10                  15

Arg Ala Thr Leu Ser Cys Arg Ala Ser Gln Val Ile Ser His Asn Leu
            20                  25                  30

Ala Trp Tyr Gln Gln Arg Thr Asn Gly Ser Pro Arg Leu Leu Ile Tyr
        35                  40                  45

Gly Ala Ser Thr Arg Ala Ser Gly Ile Pro Ala Arg Phe Ser Gly Ser
    50                  55                  60

Gly Ser Gly Thr Asp Tyr Thr Leu Thr Ile Thr Ser Leu Gln Pro Glu
65                  70                  75                  80

Asp Ile Ala Asp Tyr Tyr Cys Gln His Tyr Ser Asn Trp Pro Pro Arg
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 76
<211> LENGTH: 228
<212> TYPE: PRT
<213> ORGANISM: Artificial Sequence
<220> FEATURE:
<223> OTHER INFORMATION: Synthetic polypeptide

<400> SEQUENCE: 76

Glu Val Gln Leu Gln Gln Ser Gly Gly Gly Leu Val Lys Thr Gly Ala
```

```
            1               5                  10                  15
        Ser Val Lys Ile Ser Cys Lys Ala Ser Gly Tyr Ser Phe Thr Ser Tyr
                        20                  25                  30
        Tyr Met His Trp Val Lys Gln Ser His Gly Lys Ser Leu Glu Trp Ile
                        35                  40                  45
        Gly Glu Ile Asn Pro Tyr Asn Gly Ala Ser Tyr Asn Gln Lys Ile
                 50                  55                  60
        Lys Gly Arg Ala Thr Phe Thr Val Asp Thr Ser Arg Thr Ala Tyr
         65                  70                  75                  80
        Met Gln Phe Asn Ser Leu Thr Ser Glu Asp Ser Ala Ile Tyr Tyr Cys
                        85                  90                  95
        Ala Arg Ser Ile Tyr Gly His Ser Val Leu Asp Tyr Trp Gly Gln Gly
                       100                 105                 110
        Thr Ser Val Ser Val Ser Ser Ala Lys Thr Thr Pro Pro Ser Val Tyr
                       115                 120                 125
        Pro Leu Ala Pro Gly Ser Ala Ala Gln Thr Asn Ser Met Val Thr Leu
                       130                 135                 140
        Gly Cys Leu Val Lys Gly Tyr Phe Pro Glu Pro Val Thr Val Thr Trp
        145                 150                 155                 160
        Asn Ser Gly Ser Leu Ser Ser Gly Val His Thr Phe Pro Ala Val Leu
                       165                 170                 175
        Gln Ser Asp Leu Tyr Thr Leu Ser Ser Val Thr Val Pro Ser Ser
                       180                 185                 190
        Thr Trp Pro Ser Gln Thr Val Thr Cys Asn Val Ala His Pro Ala Ser
                       195                 200                 205
        Ser Thr Lys Val Asp Lys Lys Ile Val Pro Arg Asp Cys Gly Cys Lys
        210                 215                 220
        Pro Cys Ile Cys
        225

<210> SEQ ID NO 77
        <211> LENGTH: 215
        <212> TYPE: PRT
        <213> ORGANISM: Artificial Sequence
        <220> FEATURE:
        <223> OTHER INFORMATION: Synthetic polypeptide

<400> SEQUENCE: 77

Ile Val Leu Thr Gln Ser Pro Ile Leu Leu Ser Val Ser Pro Gly Glu
        1               5                  10                  15
        Arg Ala Thr Leu Ser Cys Arg Ala Ser Gln Val Ile Ser His Asn Leu
                        20                  25                  30
        Ala Trp Tyr Gln Gln Arg Thr Asn Gly Ser Pro Arg Leu Leu Ile Tyr
                        35                  40                  45
        Gly Ala Ser Thr Arg Ala Ser Gly Ile Pro Ala Arg Phe Ser Gly Ser
                        50                  55                  60
        Gly Ser Gly Thr Asp Tyr Thr Leu Thr Ile Thr Ser Leu Gln Pro Glu
         65                  70                  75                  80
        Asp Glu Ala Asp Tyr Tyr Cys Gln His Tyr Ser Asn Trp Pro Pro Arg
                        85                  90                  95
        Leu Thr Phe Gly Gly Gly Thr Lys Val Glu Ile Lys Arg Thr Val Ala
                       100                 105                 110
        Ala Pro Ser Val Phe Ile Phe Pro Pro Ser Asp Glu Gln Leu Lys Ser
                       115                 120                 125
        Gly Thr Ala Ser Val Val Cys Leu Leu Asn Asn Phe Tyr Pro Arg Glu
```

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 78
<211> LENGTH: 228
<212> TYPE: PRT
<213> ORGANISM: Artificial Sequence
<220> FEATURE:
<223> OTHER INFORMATION: Synthetic polypeptide

<400> SEQUENCE: 78

Glu Val Gln Leu Gln Gln Ser Gly Gly Gly Leu Val Lys Thr Gly Ala
1               5                   10                  15

Ser Val Lys Ile Ser Cys Lys Ala Ser Gly Tyr Ser Phe Thr Ser Tyr
            20                  25                  30

Tyr Met His Trp Val Lys Gln Ser His Gly Lys Ser Leu Glu Trp Ile
        35                  40                  45

Gly Glu Ile Asn Pro Tyr Asn Gly Gly Ala Ser Tyr Asn Gln Lys Ile
    50                  55                  60

Lys Gly Arg Ala Thr Phe Thr Val Asp Thr Ser Ser Arg Thr Ala Tyr
65                  70                  75                  80

Met Gln Phe Asn Ser Leu Thr Ser Glu Asp Ser Ala Ile Tyr Tyr Cys
                85                  90                  95

Ala Arg Ser Ile Tyr Gly His Ser Val Leu Asp Tyr Trp Gly Gln Gly
            100                 105                 110

Thr Ser Val Ser Val Ser Ser Ala Lys Thr Thr Pro Pro Ser Val Tyr
        115                 120                 125

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Pro Ser Ser
            180                 185                 190

Thr Trp Pro Ser Gln Thr Val Thr Cys Asn Val Ala His Pro Ala Ser
        195                 200                 205

Ser Thr Lys Val Asp Lys Lys Ile Val Pro Arg Asp Cys Gly Cys Lys
    210                 215                 220

Pro Cys Ile Cys
225

<210> SEQ ID NO 79
<211> LENGTH: 214
<212> TYPE: PRT
<213> ORGANISM: Artificial Sequence
<220> FEATURE:
<223> OTHER INFORMATION: Synthetic polypeptide

```
<400> SEQUENCE: 79

Asp Ile Val Met Thr Gln Ser His Ile Leu Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Arg Thr Asn Gly Ser Pro Arg Leu Leu Ile
        35                  40                  45

Ser Trp Ala Ser Thr Arg His Thr Gly Val Pro Asp Arg Phe Thr Gly
50                  55                  60

Ser Gly Ser Gly Thr Asp Tyr Thr Leu Thr Ile Ser Ser Val Gln Ala
65                  70                  75                  80

Glu Asp Ile Ala Asp Tyr Tyr Cys Gln Gln His Tyr Thr Thr Pro Leu
            85                  90                  95

Thr Phe Gly Ala Gly Thr Lys Leu Glu Leu Lys Arg Ala Asp Ala Ala
        100                 105                 110

Pro Thr Val Ser Ile Phe Pro Pro Ser Glu Gln Leu Thr Ser Gly
            115                 120                 125

Gly Ala Ser Val Val Cys Phe Leu Asn Asn Phe Tyr Pro Lys Asp Ile
130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Gly Glu Cys
        210

<210> SEQ ID NO 80
<211> LENGTH: 219
<212> TYPE: PRT
<213> ORGANISM: Artificial Sequence
<220> FEATURE:
<223> OTHER INFORMATION: Synthetic polypeptide

<400> SEQUENCE: 80

Gln Val Gln Leu Gln Gln Ser Gly Gly Gly Leu Met Lys Pro Gly Ala
1               5                   10                  15

Ser Val Gln Ile Ser Cys Lys Ala Thr Gly Tyr Thr Phe Ser Asp Tyr
            20                  25                  30

Trp Ile Glu Trp Val Lys Gln Ser Pro Gly His Gly Leu Glu Trp Ile
        35                  40                  45

Gly Asp Ile Leu Cys Gly Thr Gly Arg Thr Arg Tyr Asn Glu Lys Leu
50                  55                  60

Lys Ala Met Ala Thr Phe Thr Ala Asp Thr Ser Ser Asn Thr Ala Phe
65                  70                  75                  80

Met Gln Leu Ser Ser Leu Thr Ser Glu Asp Ser Ala Ile Tyr Tyr Cys
            85                  90                  95

Ala Arg Ser Ala Ser Tyr Gly Asp Tyr Ala Asp Tyr Trp Gly His Gly
            100                 105                 110

Thr Thr Leu Thr Val Ser Ser Ala Lys Thr Thr Pro Pro Ser Val Tyr
            115                 120                 125
```

```
Pro Leu Ala Pro Gly Cys Gly Asp Thr Thr Gly Ser Ser Val Thr Leu
    130                 135                 140

Gly Cys Leu Val Lys Gly Tyr Phe Pro Glu Ser Val Thr Val Thr Trp
145                 150                 155                 160

Asn Ser Gly Ser Leu Ser Ser Ser Val His Thr Phe Pro Ala Leu Leu
                165                 170                 175

Gln Ser Gly Leu Tyr Thr Met Ser Ser Ser Val Thr Val Pro Ser Ser
                180                 185                 190

Thr Trp Pro Ser Gln Thr Val Thr Cys Ser Val Ala His Pro Ala Ser
            195                 200                 205

Ser Thr Thr Val Asp Lys Lys Leu Glu Pro Ser
    210                 215
```

<210> SEQ ID NO 81
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 81

```
Asp Ile Val Met Thr Gln Ser His Ile Leu Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Arg Thr Asn Gly Ser Pro Arg Leu Leu Ile
        35                  40                  45

Ser Trp Ala Ser Thr Arg His Thr Gly Val Pro Asp Arg Phe Thr Gly
    50                  55                  60

Ser Gly Ser Gly Thr Asp Tyr Thr Leu Thr Ile Ser Ser Val Gln Ala
65                  70                  75                  80

Glu Asp Glu Ala Asp Tyr Tyr Cys Gln Gln His Tyr Thr Thr Pro Leu
                85                  90                  95

Thr Phe Gly Ala Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Gly Glu Cys
    210
```

<210> SEQ ID NO 82
<211> LENGTH: 219
<212> TYPE: PRT
<213> ORGANISM: Artificial Sequence
<220> FEATURE:
<223> OTHER INFORMATION: Synthetic polypeptide

<400> SEQUENCE: 82

Gln Val Gln Leu Gln Gln Ser Gly Gly Gly Leu Met Lys Pro Gly Ala
1               5                   10                  15

Ser Val Gln Ile Ser Cys Lys Ala Thr Gly Tyr Thr Phe Ser Asp Tyr
            20                  25                  30

Trp Ile Glu Trp Val Lys Gln Ser Pro Gly His Gly Leu Glu Trp Ile
        35                  40                  45

Gly Asp Ile Leu Cys Gly Thr Gly Arg Thr Arg Tyr Asn Glu Lys Leu
    50                  55                  60

Lys Ala Met Ala Thr Phe Thr Ala Asp Thr Ser Ser Asn Thr Ala Phe
65                  70                  75                  80

Met Gln Leu Ser Ser Leu Thr Ser Glu Asp Ser Ala Ile Tyr Tyr Cys
                85                  90                  95

Ala Arg Ser Ala Ser Tyr Gly Asp Tyr Ala Asp Tyr Trp Gly His Gly
                100                 105                 110

Thr Thr Leu Thr Val Ser Ser Ala Lys Thr Thr Pro Pro Ser Val Tyr
            115                 120                 125

Pro Leu Ala Pro Gly Cys Gly Asp Thr Thr Gly Ser Ser Val Thr Leu
        130                 135                 140

Gly Cys Leu Val Lys Gly Tyr Phe Pro Glu Ser Val Thr Val Thr Trp
145                 150                 155                 160

Asn Ser Gly Ser Leu Ser Ser Val His Thr Phe Pro Ala Leu Leu
                165                 170                 175

Gln Ser Gly Leu Tyr Thr Met Ser Ser Ser Val Thr Val Pro Ser Ser
                180                 185                 190

Thr Trp Pro Ser Gln Thr Val Thr Cys Ser Val Ala His Pro Ala Ser
            195                 200                 205

Ser Thr Thr Val Asp Lys Lys Leu Glu Pro Ser
            210                 215

<210> SEQ ID NO 83
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 83

Pro Val Lys Gln Leu Leu Asn Phe Asp Leu Leu Lys Leu Ala Gly Asp
1               5                   10                  15

Val Glu Ser Asn Pro Gly Pro
            20

<210> SEQ ID NO 84
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 84

Gln Cys Thr Asn Tyr Ala Leu Leu Lys Leu Ala Gly Asp Val Glu Ser
1               5                   10                  15

Asn Pro Gly Pro
            20

<210> SEQ ID NO 85
<211> LENGTH: 19
<212> TYPE: PRT

<213> ORGANISM: Artificial Sequence
<220> FEATURE:
<223> OTHER INFORMATION: Synthetic polypeptide

<400> SEQUENCE: 85

```
Ala Thr Asn Phe Ser Leu Leu Lys Gln Ala Gly Asp Val Glu Glu Asn
1               5                   10                  15
Pro Gly Pro
```

<210> SEQ ID NO 86
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 86

```
Glu Gly Arg Gly Ser Leu Leu Thr Cys Gly Asp Val Glu Ser Asn Pro
1               5                   10                  15
Gly Pro
```

<210> SEQ ID NO 87
<211> LENGTH: 22
<212> TYPE: PRT
<213> ORGANISM: Artificial Sequence
<220> FEATURE:
<223> OTHER INFORMATION: Synthetic polypeptide

<400> SEQUENCE: 87

```
Met Leu Leu Leu Val Thr Ser Leu Leu Leu Cys Glu Leu Pro His Pro
1               5                   10                  15
Ala Phe Leu Leu Ile Pro
            20
```

<210> SEQ ID NO 88
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 88

```
Asp Ile Gln Met Thr Gln Ser Pro Ile Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Arg Thr Asn Gly Ser Pro Arg Leu Leu Ile
            35                  40                  45

Tyr Ser Ala Ser Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Glu Ala Asp Tyr Tyr Cys Gln Gln His Tyr Thr Thr Pro Pro
                85                  90                  95

Thr Phe Gly Ala Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 89
<211> LENGTH: 22
<212> TYPE: PRT
<213> ORGANISM: Artificial Sequence
<220> FEATURE:
<223> OTHER INFORMATION: Synthetic polypeptide

<400> SEQUENCE: 89

Leu Glu Gly Gly Gly Glu Gly Arg Gly Ser Leu Leu Thr Cys Gly Asp
1               5                   10                  15

Val Glu Glu Asn Pro Gly
            20

<210> SEQ ID NO 90
<211> LENGTH: 245
<212> TYPE: PRT
<213> ORGANISM: Artificial Sequence
<220> FEATURE:
<223> OTHER INFORMATION: Synthetic polypeptide

<400> SEQUENCE: 90

Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Asn Ile Lys Asp Thr Tyr Ile His Trp Val Arg Gln Ser Pro Gly
    50                  55                  60

Lys Gly Leu Glu Trp Val Ala Arg Ile Tyr Pro Thr Asn Gly Tyr Thr
65                  70                  75                  80

Arg Tyr Ala Asp Ser Val Lys Gly Arg Phe Thr Ile Ser Ala Asp Thr
                85                  90                  95

Ser Lys Asn Thr Ala Tyr Leu Gln Met Asn Ser Leu Arg Ala Glu Asp
            100                 105                 110

Thr Ala Ile Tyr Tyr Cys Ser Arg Trp Gly Gly Asp Gly Phe Tyr Ala
        115                 120                 125

Met Asp Tyr Trp Gly Gln Gly Thr Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205
```

```
Ser Val Val Thr Val Pro Ser Ser Leu Gly Thr Gln Thr Tyr Ile
        210                 215                 220
Cys Asn Val Asn His Lys Pro Ser Asn Thr Lys Val Asp Lys Lys Val
225                 230                 235                 240
Glu Pro Lys Ser Cys
                245

<210> SEQ ID NO 91
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 91

Glu Ser Lys Tyr Gly Pro Pro Cys Pro Pro Cys Pro
1               5                  10

<210> SEQ ID NO 92
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 92

Gly Gly Gly Ser Ser Gly Gly Gly Ser Gly
1               5                  10

<210> SEQ ID NO 93
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 93

Gly Gln Pro Arg Glu Pro Gln Val Tyr Thr Leu Pro Pro Ser Gln Glu
1               5                  10                  15
Glu Met Thr Lys Asn Gln Val Ser Leu Thr Cys Leu Val Lys Gly Phe
            20                  25                  30
Tyr Pro Ser Asp Ile Ala Val Glu Trp Glu Ser Asn Gly Gln Pro Glu
        35                  40                  45
Asn Asn Tyr Lys Thr Thr Pro Pro Val Leu Asp Ser Asp Gly Ser Phe
    50                  55                  60
Phe Leu Tyr Ser Arg Leu Thr Val Asp Lys Ser Arg Trp Gln Glu Gly
65                  70                  75                  80
Asn Val Phe Ser Cys Ser Val Met His Glu Ala Leu His Asn His Tyr
                85                  90                  95
Thr Gln Lys Ser Leu Ser Leu Ser Leu Gly Lys
            100                 105

<210> SEQ ID NO 94
<211> LENGTH: 28
<212> TYPE: PRT
<213> ORGANISM: Artificial Sequence
<220> FEATURE:
<223> OTHER INFORMATION: Synthetic polypeptide

<400> SEQUENCE: 94

Met Phe Trp Val Leu Val Val Val Gly Gly Val Leu Ala Cys Tyr Ser
1               5                  10                  15
```

```
Leu Leu Val Thr Val Ala Phe Ile Ile Phe Trp Val
            20                  25
```

<210> SEQ ID NO 95
<211> LENGTH: 41
<212> TYPE: PRT
<213> ORGANISM: Artificial Sequence
<220> FEATURE:
<223> OTHER INFORMATION: Synthetic polypeptide

<400> SEQUENCE: 95

```
Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
            35                  40
```

<210> SEQ ID NO 96
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 96

```
Gly Gly Gly
1
```

<210> SEQ ID NO 97
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 97

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 98
<211> LENGTH: 816
<212> TYPE: PRT
<213> ORGANISM: Artificial Sequence
<220> FEATURE:
<223> OTHER INFORMATION: Synthetic polypeptide

<400> SEQUENCE: 98

```
Met Leu Leu Leu Val Thr Ser Leu Leu Leu Cys Glu Leu Pro His Pro
1               5                   10                  15
```

```
Ala Phe Leu Leu Ile Pro Asp Ile Gln Met Thr Gln Ser Pro Ile Leu
                20                  25                  30

Leu Ser Ala Ser Val Gly Asp Arg Val Thr Ile Thr Cys Arg Ala Ser
            35                  40                  45

Gln Asp Val Asn Thr Ala Val Ala Trp Tyr Gln Gln Arg Thr Asn Gly
 50                  55                  60

Ser Pro Arg Leu Leu Ile Tyr Ser Ala Ser Phe Leu Tyr Ser Gly Val
 65                  70                  75                  80

Pro Ser Arg Phe Ser Gly Ser Arg Ser Gly Thr Asp Phe Thr Leu Thr
                85                  90                  95

Ile Ser Ser Leu Gln Pro Glu Asp Glu Ala Asp Tyr Tyr Cys Gln Gln
                100                 105                 110

His Tyr Thr Thr Pro Pro Thr Phe Gly Ala Gly Thr Lys Val Glu Ile
            115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys Leu Glu Gly Gly
225                 230                 235                 240

Gly Glu Gly Arg Gly Ser Leu Leu Thr Cys Gly Asp Val Glu Glu Asn
                245                 250                 255

Pro Gly Met Leu Leu Leu Val Thr Ser Leu Leu Cys Glu Leu Pro
            260                 265                 270

His Pro Ala Phe Leu Leu Ile Pro Glu Val Gln Leu Val Glu Ser Gly
        275                 280                 285

Gly Gly Leu Val Gln Pro Gly Gly Ser Leu Arg Leu Ser Cys Ala Ala
        290                 295                 300

Ser Gly Phe Asn Ile Lys Asp Thr Tyr Ile His Trp Val Arg Gln Ser
305                 310                 315                 320

Pro Gly Lys Gly Leu Glu Trp Val Ala Arg Ile Tyr Pro Thr Asn Gly
                325                 330                 335

Tyr Thr Arg Tyr Ala Asp Ser Val Lys Gly Arg Phe Thr Ile Ser Ala
            340                 345                 350

Asp Thr Ser Lys Asn Thr Ala Tyr Leu Gln Met Asn Ser Leu Arg Ala
        355                 360                 365

Glu Asp Thr Ala Ile Tyr Tyr Cys Ser Arg Trp Gly Gly Asp Gly Phe
370                 375                 380

Tyr Ala Met Asp Tyr Trp Gly Gln Gly Thr Leu Val Thr Val Ser Ser
385                 390                 395                 400

Ala Ser Thr Lys Gly Pro Ser Val Phe Pro Leu Ala Pro Ser Ser Lys
                405                 410                 415

Ser Thr Ser Gly Gly Thr Ala Ala Leu Gly Cys Leu Val Lys Asp Tyr
            420                 425                 430
```

Phe Pro Glu Pro Val Thr Val Ser Trp Asn Ser Gly Ala Leu Thr Ser
            435                 440                 445

Gly Val His Thr Phe Pro Ala Val Leu Gln Ser Ser Gly Leu Tyr Ser
450                 455                 460

Leu Ser Ser Val Val Thr Val Pro Ser Ser Ser Leu Gly Thr Gln Thr
465                 470                 475                 480

Tyr Ile Cys Asn Val Asn His Lys Pro Ser Asn Thr Lys Val Asp Lys
                485                 490                 495

Lys Val Glu Pro Lys Ser Cys Glu Ser Lys Tyr Gly Pro Pro Cys Pro
            500                 505                 510

Pro Cys Pro Gly Gly Ser Gly Gly Gly Ser Gly Gly Gln Pro
        515                 520                 525

Arg Glu Pro Gln Val Tyr Thr Leu Pro Pro Ser Gln Glu Glu Met Thr
        530                 535                 540

Lys Asn Gln Val Ser Leu Thr Cys Leu Val Lys Gly Phe Tyr Pro Ser
545                 550                 555                 560

Asp Ile Ala Val Glu Trp Glu Ser Asn Gly Gln Pro Glu Asn Asn Tyr
                565                 570                 575

Lys Thr Thr Pro Pro Val Leu Asp Ser Asp Gly Ser Phe Phe Leu Tyr
            580                 585                 590

Ser Arg Leu Thr Val Asp Lys Ser Arg Trp Gln Glu Gly Asn Val Phe
        595                 600                 605

Ser Cys Ser Val Met His Glu Ala Leu His Asn His Tyr Thr Gln Lys
        610                 615                 620

Ser Leu Ser Leu Ser Leu Gly Lys Met Phe Trp Val Leu Val Val Val
625                 630                 635                 640

Gly Gly Val Leu Ala Cys Tyr Ser Leu Leu Val Thr Val Ala Phe Ile
                645                 650                 655

Ile Phe Trp Val Arg Ser Lys Arg Ser Arg Gly Gly His Ser Asp Tyr
            660                 665                 670

Met Asn Met Thr Pro Arg Arg Pro Gly Pro Thr Arg Lys His Tyr Gln
        675                 680                 685

Pro Tyr Ala Pro Pro Arg Asp Phe Ala Ala Tyr Arg Ser Gly Gly Gly
690                 695                 700

Arg Val Lys Phe Ser Arg Ser Ala Asp Ala Pro Ala Tyr Gln Gln Gly
705                 710                 715                 720

Gln Asn Gln Leu Tyr Asn Glu Leu Asn Leu Gly Arg Arg Glu Glu Tyr
                725                 730                 735

Asp Val Leu Asp Lys Arg Arg Gly Arg Asp Pro Glu Met Gly Gly Lys
            740                 745                 750

Pro Arg Arg Lys Asn Pro Gln Glu Gly Leu Tyr Asn Glu Leu Gln Lys
        755                 760                 765

Asp Lys Met Ala Glu Ala Tyr Ser Glu Ile Gly Met Lys Gly Glu Arg
        770                 775                 780

Arg Arg Gly Lys Gly His Asp Gly Leu Tyr Gln Gly Leu Ser Thr Ala
785                 790                 795                 800

Thr Lys Asp Thr Tyr Asp Ala Leu His Met Gln Ala Leu Pro Pro Arg
                805                 810                 815

<210> SEQ ID NO 99
<211> LENGTH: 22
<212> TYPE: PRT
<213> ORGANISM: Artificial Sequence
<220> FEATURE:
<223> OTHER INFORMATION: Synthetic polypeptide

<400> SEQUENCE: 99

Met Leu Leu Leu Val Thr Ser Leu Leu Cys Glu Leu Pro His Pro
1               5                   10                  15

Ala Phe Leu Leu Ile Pro
            20

<210> SEQ ID NO 100
<211> LENGTH: 223
<212> TYPE: PRT
<213> ORGANISM: Artificial Sequence
<220> FEATURE:
<223> OTHER INFORMATION: Synthetic polypeptide

<400> SEQUENCE: 100

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ser Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Ile Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys
    210                 215                 220

<210> SEQ ID NO 101
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 101

Glu Ser Lys Tyr Gly Pro Pro Cys Pro Pro Cys Pro
1               5                   10

<210> SEQ ID NO 102
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 102

Gly Gly Gly Ser Ser Gly Gly Gly Ser Gly
1               5                   10

<210> SEQ ID NO 103
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 103

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 104
<211> LENGTH: 28
<212> TYPE: PRT
<213> ORGANISM: Artificial Sequence
<220> FEATURE:
<223> OTHER INFORMATION: Synthetic polypeptide

<400> SEQUENCE: 104

Met Phe Trp Val Leu Val Val Val Gly Gly Val Leu Ala Cys Tyr Ser
1               5                   10                  15

Leu Leu Val Thr Val Ala Phe Ile Ile Phe Trp Val
            20                  25

<210> SEQ ID NO 105
<211> LENGTH: 41
<212> TYPE: PRT
<213> ORGANISM: Artificial Sequence
<220> FEATURE:
<223> OTHER INFORMATION: Synthetic polypeptide

<400> SEQUENCE: 105

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 106
<211> LENGTH: 3
<212> TYPE: PRT
<213> ORGANISM: Artificial Sequence

```
<220> FEATURE:
<223> OTHER INFORMATION: Synthetic polypeptide

<400> SEQUENCE: 106

Gly Gly Gly
1

<210> SEQ ID NO 107
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 107

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 108
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 108

Leu Glu Gly Gly Gly Glu Gly Arg Gly Ser Leu Leu Thr Cys Gly Asp
1               5                   10                  15

Val Glu Glu Asn Pro Gly Pro Arg
            20

<210> SEQ ID NO 109
<211> LENGTH: 236
<212> TYPE: PRT
<213> ORGANISM: Artificial Sequence
<220> FEATURE:
<223> OTHER INFORMATION: Synthetic polypeptide

<400> SEQUENCE: 109

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Ser Pro Ile Leu
            20                  25                  30

Leu Ser Ala Ser Val Gly Asp Arg Val Thr Ile Thr Cys Arg Ala Ser
        35                  40                  45

Gln Asp Val Asn Thr Ala Val Ala Trp Tyr Gln Gln Arg Thr Asn Gly
    50                  55                  60

Ser Pro Arg Leu Leu Ile Tyr Ser Ala Ser Phe Leu Tyr Ser Gly Val
65                  70                  75                  80
```

```
Pro Ser Arg Phe Ser Gly Ser Arg Ser Gly Thr Asp Phe Thr Leu Thr
                85                  90                  95

Ile Ser Ser Leu Gln Pro Glu Asp Glu Ala Asp Tyr Tyr Cys Gln Gln
                100                 105                 110

His Tyr Thr Thr Pro Pro Thr Phe Gly Ala Gly Thr Lys Val Glu Ile
                115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
                180                 185                 190

Ser Thr Tyr Ser Leu Ser Ser Thr Leu Thr Leu Ser Lys Ala Asp Tyr
                195                 200                 205

Glu Lys His Lys Val Tyr Ala Cys Glu Val Thr His Gln Gly Leu Ser
                210                 215                 220

Ser Pro Val Thr Lys Ser Phe Asn Arg Gly Glu Cys
225                 230                 235

<210> SEQ ID NO 110
<211> LENGTH: 818
<212> TYPE: PRT
<213> ORGANISM: Artificial Sequence
<220> FEATURE:
<223> OTHER INFORMATION: Synthetic polypeptide

<400> SEQUENCE: 110

Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
                20                  25                  30

Leu Val Gln Pro Gly Gly Ser Leu Arg Leu Ser Cys Ala Ala Ser Gly
                35                  40                  45

Phe Asn Ile Lys Asp Thr Tyr Ile His Trp Val Arg Gln Ser Pro Gly
    50                  55                  60

Lys Gly Leu Glu Trp Val Ala Arg Ile Tyr Pro Thr Asn Gly Tyr Thr
65                  70                  75                  80

Arg Tyr Ala Asp Ser Val Lys Gly Arg Phe Thr Ile Ser Ala Asp Thr
                85                  90                  95

Ser Lys Asn Thr Ala Tyr Leu Gln Met Asn Ser Leu Arg Ala Glu Asp
                100                 105                 110

Thr Ala Ile Tyr Tyr Cys Ser Arg Trp Gly Gly Asp Gly Phe Tyr Ala
                115                 120                 125

Met Asp Tyr Trp Gly Gln Gly Thr Leu Val Thr Val Ser Ser Ala Ser
                130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
                180                 185                 190

His Thr Phe Pro Ala Val Leu Gln Ser Ser Gly Leu Tyr Ser Leu Ser
                195                 200                 205
```

```
Ser Val Val Thr Val Pro Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys Glu Ser Lys Tyr Gly Pro Pro Cys Pro Pro Cys
                245                 250                 255

Pro Gly Gly Gly Ser Ser Gly Gly Ser Gly Gly Gln Pro Arg Glu
        260                 265                 270

Pro Gln Val Tyr Thr Leu Pro Pro Ser Gln Glu Glu Met Thr Lys Asn
    275                 280                 285

Gln Val Ser Leu Thr Cys Leu Val Lys Gly Phe Tyr Pro Ser Asp Ile
290                 295                 300

Ala Val Glu Trp Glu Ser Asn Gly Gln Pro Glu Asn Asn Tyr Lys Thr
305                 310                 315                 320

Thr Pro Pro Val Leu Asp Ser Asp Gly Ser Phe Phe Leu Tyr Ser Arg
                325                 330                 335

Leu Thr Val Asp Lys Ser Arg Trp Gln Glu Gly Asn Val Phe Ser Cys
        340                 345                 350

Ser Val Met His Glu Ala Leu His Asn His Tyr Thr Gln Lys Ser Leu
    355                 360                 365

Ser Leu Ser Leu Gly Lys Met Phe Trp Val Leu Val Val Val Gly Gly
370                 375                 380

Val Leu Ala Cys Tyr Ser Leu Leu Val Thr Val Ala Phe Ile Ile Phe
385                 390                 395                 400

Trp Val Arg Ser Lys Arg Ser Arg Gly Gly His Ser Asp Tyr Met Asn
                405                 410                 415

Met Thr Pro Arg Arg Pro Gly Pro Thr Arg Lys His Tyr Gln Pro Tyr
        420                 425                 430

Ala Pro Pro Arg Asp Phe Ala Ala Tyr Arg Ser Gly Gly Gly Arg Val
    435                 440                 445

Lys Phe Ser Arg Ser Ala Asp Ala Pro Ala Tyr Gln Gln Gly Gln Asn
450                 455                 460

Gln Leu Tyr Asn Glu Leu Asn Leu Gly Arg Arg Glu Glu Tyr Asp Val
465                 470                 475                 480

Leu Asp Lys Arg Arg Gly Arg Asp Pro Glu Met Gly Gly Lys Pro Arg
                485                 490                 495

Arg Lys Asn Pro Gln Glu Gly Leu Tyr Asn Glu Leu Gln Lys Asp Lys
        500                 505                 510

Met Ala Glu Ala Tyr Ser Glu Ile Gly Met Lys Gly Glu Arg Arg Arg
    515                 520                 525

Gly Lys Gly His Asp Gly Leu Tyr Gln Gly Leu Ser Thr Ala Thr Lys
530                 535                 540

Asp Thr Tyr Asp Ala Leu His Met Gln Ala Leu Pro Pro Arg Leu Glu
545                 550                 555                 560

Gly Gly Gly Glu Gly Arg Gly Ser Leu Leu Thr Cys Gly Asp Val Glu
                565                 570                 575

Glu Asn Pro Gly Pro Arg Met Leu Leu Leu Val Thr Ser Leu Leu Leu
        580                 585                 590

Cys Glu Leu Pro His Pro Ala Phe Leu Leu Ile Pro Asp Ile Gln Met
    595                 600                 605

Thr Gln Ser Pro Ile Leu Leu Ser Ala Ser Val Gly Asp Arg Val Thr
610                 615                 620
```

```
Ile Thr Cys Arg Ala Ser Gln Asp Val Asn Thr Ala Val Ala Trp Tyr
625                 630                 635                 640

Gln Gln Arg Thr Asn Gly Ser Pro Arg Leu Leu Ile Tyr Ser Ala Ser
                645                 650                 655

Phe Leu Tyr Ser Gly Val Pro Ser Arg Phe Ser Gly Ser Arg Ser Gly
            660                 665                 670

Thr Asp Phe Thr Leu Thr Ile Ser Ser Leu Gln Pro Glu Asp Glu Ala
            675                 680                 685

Asp Tyr Tyr Cys Gln Gln His Tyr Thr Thr Pro Pro Thr Phe Gly Ala
        690                 695                 700

Gly Thr Lys Val Glu Ile Lys Arg Thr Val Ala Ala Pro Ser Val Phe
705                 710                 715                 720

Ile Phe Pro Pro Ser Asp Glu Gln Leu Lys Ser Gly Thr Ala Ser Val
                725                 730                 735

Val Cys Leu Leu Asn Asn Phe Tyr Pro Arg Glu Ala Lys Val Gln Trp
            740                 745                 750

Lys Val Asp Asn Ala Leu Gln Ser Gly Asn Ser Gln Glu Ser Val Thr
            755                 760                 765

Glu Gln Asp Ser Lys Asp Ser Thr Tyr Ser Leu Ser Ser Thr Leu Thr
    770                 775                 780

Leu Ser Lys Ala Asp Tyr Glu Lys His Lys Val Tyr Ala Cys Glu Val
785             790                 795                 800

Thr His Gln Gly Leu Ser Ser Pro Val Thr Lys Ser Phe Asn Arg Gly
                805                 810                 815

Glu Cys
```

CHIMERIC ANTIGEN RECEPTOR COMPOSITIONS

CROSS-REFERENCES TO RELATED APPLICATIONS

This application claims priority to U.S. Provisional Application No. 62/162,599, filed May 15, 2015, the disclosure of which is incorporated herein in its entirety and for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 48440-558001US_ST25.TXT, created on May 12, 2016, 169,534 bytes, machine format IBM-PC, MS-Windows operating system, is hereby incorporated by reference in its entirety for all purposes.

BACKGROUND OF THE INVENTION

Cancer is the second leading cause of death in the United States, killing more people than the next five causes combined including chronic respiratory disease, Alzheimer's disease and diabetes. While extraordinary strides have been made in the detection, prevention and treatment of cancer, there remains an urgent need, especially in advanced cases, to produce therapies that not only halt tumor progression but effectively eliminate all tumor cells. One approach is adoptive T cell immunotherapy (5-7). This method requires the harvesting of the patient's T cells, engineering of these cells with a chimeric antigen receptor (CAR) that recognizes a tumor antigen, and subsequent re-introduction of the modified cells to the patient. The re-programmed T cells then directly target antigen-expressing tumor cells, bypassing the requirement for MHC peptide, and elicit a powerful but localized immune response. This method of treatment (8) has produced some positive results in early clinical trials for a handful, but not for all patients. There is a need in the art to better understand CAR T cell therapy's success and failure. For example, there is a need in the art for the ability to characterize the density of the CARs on the transformed cells, to track administered CAR T cells at any point during therapy and correlate this distribution to therapeutic outcomes, to rapidly functionalize CAR T cells, monitoring the number, location and viability of the transplanted CAR T cells in situ and to selectively eliminate CAR T cells if necessary. Meaningful correlations would aid clinicians in determining the best treatment options and give researchers important clues to modify and improve this therapeutic approach. Provided herein are compositions and methods addressing these and other needs in the art.

BRIEF SUMMARY OF THE INVENTION

In one aspect, an isolated nucleic acid is provided. The nucleic acid encodes a protein including (i) an antibody region including a central cavity formed by a heavy chain variable (VH) region, a light chain variable (VL) region, a heavy chain constant region (CH) and a light chain constant region (CL), wherein the central cavity forms a peptide binding site including framework region amino acid residues; and (ii) a transmembrane domain.

In one aspect, an isolated nucleic acid is provided. The nucleic acid encodes a protein including (i) an antibody region including a central cavity formed by a heavy chain variable (VH) region and a light chain variable (VL) region, wherein the central cavity forms a peptide binding site including framework region amino acid residues; and (ii) a transmembrane domain.

In another aspect, an isolated nucleic acid is provided. The isolated nucleic acid encodes a protein including a first portion including an antibody heavy chain variable domain and a second portion including an antibody light chain variable domain and an antibody light chain constant domain, wherein the first portion further includes a transmembrane domain.

In another aspect, an expression vector including a nucleic acid provided herein including embodiments thereof is provided.

In another aspect, a T lymphocyte including the expression vector provided herein including embodiments thereof is provided.

In another aspect, a mammalian cell including the expression vector provided herein including embodiments thereof is provided.

In another aspect, a recombinant protein is provided. The recombinant protein includes (i) an antibody region including a central cavity formed by a heavy chain variable (VH) region and a light chain variable (VL) region, wherein the central cavity forms a peptide binding site including framework region amino acid residues; and (ii) a transmembrane domain.

In another aspect, a recombinant protein is provided. The recombinant protein includes a first portion including an antibody heavy chain variable domain and a second portion including an antibody light chain variable domain and an antibody light chain constant domain, wherein the first portion further includes a transmembrane domain, and wherein the antibody heavy chain variable domain, the antibody light chain variable domain and the antibody light chain constant domain together form an antibody region.

In another aspect, a mammalian cell including the recombinant protein provided herein including embodiments thereof is provided, wherein the transmembrane domain is within the cell membrane of the mammalian cell.

In another aspect, a T lymphocyte including the recombinant protein provided herein including embodiments thereof is provided, wherein the transmembrane domain is within the cell membrane of the T lymphocyte.

In another aspect, a method of treating cancer is provided. The method includes administering to a subject in need thereof an effective amount of a mammalian cell provided herein including embodiments thereof, wherein the antibody region is an anti-cancer antibody region.

In another aspect, a method of treating cancer is provided. The method includes administering to a subject in need thereof an effective amount of the T-lymphocyte provided herein including embodiments thereof, wherein the antibody region is an anti-cancer antibody region.

In another aspect, a method of reprogramming a T lymphocyte is provided. The method includes contacting a T lymphocyte with the expression vector provided herein including embodiments thereof.

In another aspect, a method of detecting a cancer is provided. The method includes (i) administering to a cancer patient an effective amount of a T lymphocyte including the recombinant protein provided herein including embodiments thereof and a compound including a peptidyl moiety capable of binding to the peptide binding site, wherein the compound further includes a detectable label, and wherein the antibody region is an anti-cancer antibody region. The method includes (ii) allowing the compound to bind to the peptide binding site thereby forming a recombinant protein-compound complex. And (iii) the recombinant protein-compound complex is detected within the cancer patient thereby detecting the cancer.

BRIEF DESCRIPTION OF THE DRAWINGS

FIG. 1A: Schematic representation of chimeric antigen receptors. To specifically target tumors, full mAbs or Fab fragments that recognize tumor associated antigens are directly fused to the transmembrane domain and zeta chain. In addition, the meditope binding site can be grafted onto the mAB/Fabs, providing an additional means of adding functionality to CART cells. FIG. 1B. Since two chains have to be expressed (e.g., the light and heavy chains of the mAb plus the transmembrane and intracellular signaling segments), there are two different possibility to express the different chains. Specifically, the light chain followed by the heavy chain or the heavy chain followed by the light chain.

FIG. 2A. Diagram of the lentiviral CAR cassette for expressing the HER2-specific CAR, including the 2A ribosomal skip sequence and truncated CD19 (CD19t) which serves as an inert immunogenic marker of cell transduction. FIG. 2B. Tcm lentivirally transduced to express HER2R:28ζ display stable cell surface expression of both the CAR and CD19 proteins.

FIG. 3A. Flow cytometry analysis evaluating HER2 surface expression in a panel of breast tumor lines, and the HER2-negative U87 glioblastoma cell line. FIG. 3B. 4-hour chromium release assay evaluating killing by HER2-28z CAR T cells demonstrates that both high and low-expressing HER2+ tumor lines are killed.

FIG. 4A Crystal structure. 5-Diphenyl-meditope and protein L are bound to trastuzumab memAb. Extracellular domain of HER2 defining the antigen binding site, was superimposed using pdb 1n8z. Note: protein L and the meditope are distinct and distant from the antigen binding site. FIG. 4B FACS. SKBR3 cells were treated with labeled trastuzumab (parental; memAb) and either sequentially or pre-mixed with labeled meditope-protein L (MPL6). Only the trastuzumab memAb shifts the meditope-Protein L, indicating that antigen binding does not preclude meditope binding. FIG. 4C Fluorescence microscopy. GFP fused to meditope-Protein L (MPL6-GFP) colocalizes with trastuzumab memAb using SKBR3 cells (top row) but not with parental trastuzumab (bottom row). This indicates a bulky biologics does not impair antigen binding. FIG. 4D Super resolution microscopy. Individual HER2 receptors can be visualized and quantified using paGFP fused to meditope-Protein L (MPL6-GFP) and trastuzumab memAb. Left panel shows entire cell. Right panel shows individual receptors.

FIG. 8A: Target Cell Expression of CEA. FIG. 8B: 4-hour Chromium Release Assay. muT84.66 derived CEA-scFv-CAR T cells recognize and kill CEA+ target cells in a 4-hour chromium release assay. By comparison the humanized M5A derived CEA-scFv-CAR T cells do not kill CEA+ Target cells.

FIG. 11A, Schematic of meditope (me)-enabled trastuzumab Fab-CAR cassette (me-HER2), with the T2A ribosomal skip sequence separating the antibody light chain (meLc) and the heavy chain fused to the IgG4-CH3-Fc linker, CD28 trasmembrane domain (Tm) and the CD28 and CD3ζ cytoplasmic signaling domains (Hc28ζ). Expression is driven by the EF1α promoter and was tested in two orientations: Lc-Hc28ζ and Hc28ζ-Lc. FIG. 11B, Primary human T cells were lentivirally transduced and expression of the meHER2-CARs was evaluated by flow cytometry. Protein L staining, which binds the Fab light chain, confirms cell surface expression of both CAR orientations, with higher expression levels (MFI) observed for the Hc28ζ-Lc (MFI 5357) vs Lc-Hc28ζ (MFI 2592) orientation. Meditope-AF647 staining confirms the functional formation of the CAR meditope pocket, with greater binding to the Hc28ζ-Lc (MFI 6042) vs Lc-Hc28ζ (MFI 2121) orientation. FIG. 11C, meHER2-CAR T cells pre-bound to meditope peptide retain the ability to bind protein L and soluble HER2-antigen, suggesting that meditope binding does not alter antigen binding properties and structural components of the Fab.

FIG. 12A-12D. Meditope-enabled HER2-CAR (meHER2) T cells degranulate at comparable levels to scFvHER2-CAR T cells in response to HER2+ targets and meditope peptide does not negatively impact T cell degranulation. FIG. 12A, HER2+ breast cancer lines MCF-7 and SK-BR-3 were assessed for cell surface expression of HER2 by flow cytometry (Biolegend; Cat#324413). MCF-7 expresses relatively low levels of HER2 as compared to SK-BR-3 which over-expresses HER2. FIG. 12B-12D CD107a degranulation assay. HD187.2 T cells were engineered to express either meHER2(Hc-Lc):28ζ CAR, meHER2(Lc-Hc):28ζ CAR, scFvHER2:28ζ CAR or no CAR (mock). Versions of the meHER2:28ζ-CAR differ only in the orientation of the heavy chain (Hc) and light chain (Lc), see FIG. 11. FIG. 12B Representative FACs showing CD107a degranulation for mock T cells (negative control) and scFvHER2-CAR T cells (positive control) following co-culture at a 1:1 effector to MCF-7 ratio (based on CAR expression) for 5 hours. CD107a degranulation (BD Pharmingen™; Cat#555800), gated on CAR+ CD8+ cells, was detected by flow cytometry (Miltenyi Biotec; MACSQuant) and analyzed using FCS Express (De Novo Software). FIG. 12C meHER2(Hc-Lc):28ζ and meHER2(Lc-Hc):28ζ T cells were incubated with and without meditope-AF647 (ME;200 nM) and degranulation to MCF-7 targets was evaluated as described in FIG. 12B. FIG. 12D, Bar graph depicting comparable degranulation of all meHER2 and scFvHER2-CAR T cell lines to either MCF-7 or SK-BR-3. meHER2-CAR T cells incubated with and without meditope peptide show comparable activation as assessed by CD107a degranulation. Plotted are average and standard deviation of three wells per condition. Cells were gated on the CD8$^+$CAR$^+$ population.

FIG. 13B, Bar graph represents the percent tumor killed per condition when normalized to mock.

DETAILED DESCRIPTION OF THE INVENTION

Definitions

Figure 1A:
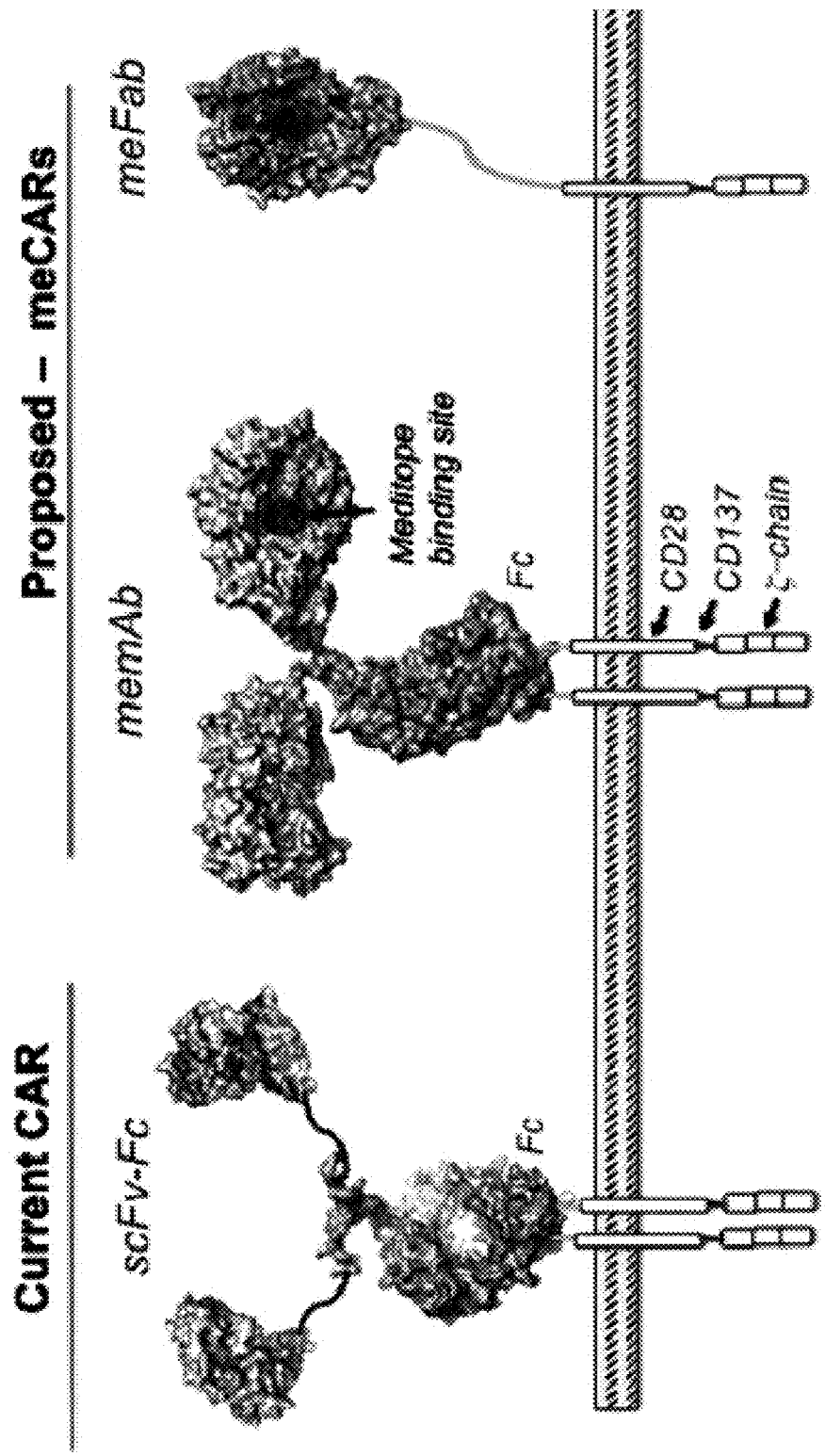
FIG. 1A-1B.
Figure 1B:
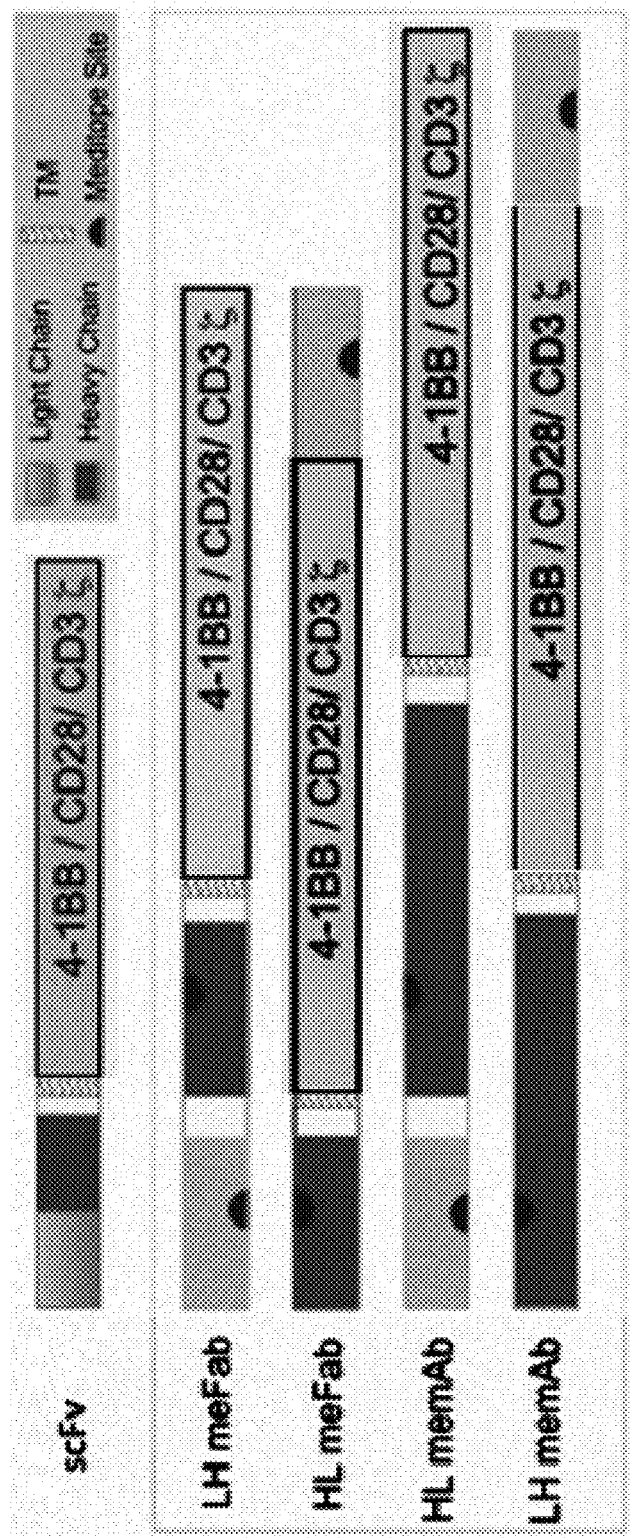

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated.

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable non-cyclic straight or branched chain, or combinations thereof, including at least one carbon atom and at least one heteroatom (e.g. O, N, P, Si or S) and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —$CH_2$—$CH_2$—

O—CH₃, —CH₂—CH₂—NH—CH₃, —CH₂—CH₂—N(CH₃)—CH₃, —CH₂—S—CH₂—CH₃, —CH₂—CH₂, —S(O)—CH₃, —CH₂—CH₂—S(O)₂—CH₃, —CH═CH—O—CH₃, —Si(CH₃)₃, —CH₂—CH═N—OCH₃, —CH═CH—N(CH₃)—CH₃, —O—CH₃, —O—CH₂—CH₃, and —CN. Up to two or three heteroatoms may be consecutive, such as, for example, —CH₂—NH—OCH₃ and —CH₂—O—Si(CH₃)₃. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, —CH₂—CH₂—S—CH₂—CH₂— and —CH₂—S—CH₂—CH₂—NH—CH₂—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)₂R'— represents both —C(O)₂R'— and —R'C(O)₂—. As described above, heteroalkyl groups, as used herein, include those groups that are attached to the remainder of the molecule through a heteroatom, such as —C(O)R', —C(O)NR', —NR'R", —OR', —SR', and/or —SO₂R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, 1H-1,2,4-triazolyl-5(4H)-one, 4H-1,2,4-triazolyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. A heterocycloalkyl moiety may include one ring heteroatom (e.g., O, N, S, Si, or P). A heterocycloalkyl moiety may include two optionally different ring heteroatoms (e.g., O, N, S, Si, or P). A heterocycloalkyl moiety may include three optionally different ring heteroatoms (e.g., O, N, S, Si, or P). A heterocycloalkyl moiety may include four optionally different ring heteroatoms (e.g., O, N, S, Si, or P). A heterocycloalkyl moiety may include five optionally different ring heteroatoms (e.g., O, N, S, Si, or P). A heterocycloalkyl moiety may include up to 8 optionally different ring heteroatoms (e.g., O, N, S, Si, or P).

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C₁-C₄)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of aryl and heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene. A heteroaryl moiety may include one ring heteroatom (e.g., O, N, or S). A heteroaryl moiety may include two optionally different ring heteroatoms (e.g., O, N, or S). A heteroaryl moiety may include three optionally different ring heteroatoms (e.g., O, N, or S). A heteroaryl moiety may include four optionally different ring heteroatoms (e.g., O, N, or S). A heteroaryl moiety may include five optionally different ring heteroatoms (e.g., O, N, or S). An aryl moiety may have a single ring. An aryl moiety may have two optionally different rings. An aryl moiety may have three optionally different rings. An aryl moiety may have four optionally different rings. A heteroaryl moiety may have one ring. A heteroaryl moiety may have two optionally different rings. A heteroaryl moiety may have three optionally different rings. A heteroaryl moiety may have four optionally different rings. A heteroaryl moiety may have five optionally different rings.

A fused ring heterocycloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

The term "oxo," as used herein, means an oxygen that is double bonded to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl,", "cycloalkyl", "heterocycloalkyl", "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R")=NR'", —S(O)R', —S(O)$_2$R', —S(O)$_2$N(R)('R"—NR$SO_2$R'), —CN, and —$NO_2$ in a number ranging from zero to (2m'+1), where m' is the total number of carbon atoms in such radical. R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", NR"C(O)$_2$R', NRC(NR'R")=NR'", S(O)R', —S(O)$_2$R', —S(O)$_2$N(R')(R", —NR$SO_2$R), —CN, —$NO_2$, —R', —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Where a moiety is substituted with an R substituent, the group may be referred to as "R-substituted." Where a moiety is R-substituted, the moiety is substituted with at least one R substituent and each R substituent is optionally different. For example, where a moiety herein is $R^{1A}$-substituted or unsubstituted alkyl, a plurality of $R^{1A}$ substituents may be attached to the alkyl moiety wherein each $R^{1A}$ substituent is optionally different. Where an R-substituted moiety is substituted with a plurality R substituents, each of the R-substituents may be differentiated herein using a prime symbol (') such as R', R", etc. For example, where a moiety is $R^{3A}$-substituted or unsubstituted alkyl, and the moiety is substituted with a plurality of $R^{3A}$ substituents, the plurality of $R^{3A}$ substituents may be differentiated as $R^{3A}$, $R^{3A'}$, $R^{3A''}$, etc. In some embodiments, the plurality of R substituents is 3. In some embodiments, the plurality of R substituents is 2.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR)$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$-B-, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R''')$_d$—, where variables s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:
(A) oxo, halogen, —CF$_3$, —CN, —OH, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O) NH$_2$, —NHSO$_2$H, —NHC═(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
(B) alkyl, heteroalkyl, cycloalkyl, heterocycloalkyl, aryl, heteroaryl, substituted with at least one substituent selected from:
  (i) oxo, halogen, —CF$_3$, —CN, —OH, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O) NH$_2$, —NHSO$_2$H, —NHC═(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
  (ii) alkyl, heteroalkyl, cycloalkyl, heterocycloalkyl, aryl, heteroaryl, substituted with at least one substituent selected from:
   (a) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O) NH$_2$, —NHSO$_2$H, —NHC═(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
   (b) alkyl, heteroalkyl, cycloalkyl, heterocycloalkyl, aryl, heteroaryl, substituted with at least one substituent selected from: oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O) NHNH$_2$, —NHC═(O) NH$_2$, —NHSO$_2$H, —NHC═(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted C$_1$-C$_{20}$ alkylene, each substituted or unsubstituted heteroalkylene is a substituted or unsubstituted 2 to 20 membered heteroalkylene, each substituted or unsubstituted cycloalkylene is a substituted or unsubstituted C$_3$-C$_8$ cycloalkylene, each substituted or unsubstituted heterocycloalkylene is a substituted or unsubstituted 3 to 8 membered heterocycloalkylene, each substituted or unsubstituted arylene is a substituted or unsubstituted C$_6$-C$_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

As used herein, the term "conjugate" refers to the association between atoms or molecules. The association can be direct or indirect. For example, a conjugate between a nucleic acid and a protein can be direct, e.g., by covalent bond, or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, conjugates are formed using conjugate chemistry including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the microparticle is non-covalently attached to solid support through a non-covalent chemical reaction between a component of the microparticle and a component of solid support. In other embodiments, the microparticle includes one or more reactive moieties, e.g., a covalent reactive moiety, as described herein (e.g., an amine reactive moiety). In other embodiments, the microparticle includes a linker with one or more reactive moieties, e.g., a covalent reactive moiety, as described herein (e.g., an amine reactive moiety).

Useful reactive moieties or functional groups used for conjugate chemistries (including "click chemistries" as known in the art) herein include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides, reacted with acyl halides, or bonded to metals such as gold;

(h) amine or sulfhydryl groups, which can be, for example, acylated, alkylated or oxidized;

(i) alkenes, which can undergo, for example, cycloadditions, acylation, Michael addition, etc.;

(j) epoxides, which can react with, for example, amines and hydroxyl compounds;

(k) phosphoramidites and other standard functional groups useful in nucleic acid synthesis;

(l) metal silicon oxide bonding;

(m) metal bonding to reactive phosphorus groups (e.g. phosphines) to form, for example, phosphate diester bonds; and (n) sulfones, for example, vinyl sulfone.

Chemical synthesis of compositions by joining small modular units using conjugate ("click") chemistry is well known in the art and described, for example, in H. C. Kolb, M. G. Finn and K. B. Sharpless ((2001). "Click Chemistry: Diverse Chemical Function from a Few Good Reactions". Angewandte Chemie International Edition 40 (11): 2004-2021); R. A. Evans ((2007). "The Rise of Azide-Alkyne 1,3-Dipolar 'Click' Cycloaddition and its Application to Polymer Science and Surface Modification". Australian Journal of Chemistry 60 (6): 384-395; W. C. Guida et al. Med. Res. Rev. p 3 1996; Spiteri, Christian and Moses, John E. ((2010). "Copper-Catalyzed Azide-Alkyne Cycloaddition: Regioselective Synthesis of 1,4,5-Trisubstituted 1,2,3-Triazoles". Angewandte Chemie International Edition 49 (1): 31-33); Hoyle, Charles E. and Bowman, Christopher N. ((2010). "Thiol-Ene Click Chemistry". Angewandte Chemie International Edition 49 (9): 1540-1573); Blackman, Melissa L. and Royzen, Maksim and Fox, Joseph M. ((2008). "Tetrazine Ligation: Fast Bioconjugation Based on Inverse-Electron-Demand Diels-Alder Reactivity". Journal of the American Chemical Society 130 (41): 13518-13519); Devaraj, Neal K. and Weissleder, Ralph and Hilderbrand, Scott A. ((2008). "Tetrazine Based Cycloadditions: Application to Pretargeted Live Cell Labeling". Bioconjugate Chemistry 19 (12): 2297-2299); Stockmann, Henning; Neves, Andre; Stairs, Shaun; Brindle, Kevin; Leeper, Finian ((2011). "Exploring isonitrile-based click chemistry for ligation with biomolecules". Organic & Biomolecular Chemistry), all of which are hereby incorporated by reference in their entirety and for all purposes.

The reactive functional groups can be chosen such that they do not participate in, or interfere with, the chemical stability of the proteins or nucleic acids described herein. By way of example, the nucleic acids can include a vinyl sulfone or other reactive moiety (e.g., maleimide). Optionally, the nucleic acids can include a reactive moiety having the formula —S—S—R. R can be, for example, a protecting group. Optionally, R is hexanol. As used herein, the term hexanol includes compounds with the formula $C_6H_{13}OH$ and includes, 1-hexanol, 2-hexanol, 3-hexanol, 2-methyl-1-pentanol, 3-methyl-1-pentanol, 4-methyl-1-pentanol, 2-methyl-2-pentanol, 3-methyl-2-pentanol, 4-methyl-2-pentanol, 2-methyl-3-pentanol, 3-methyl-3-pentanol, 2,2-dimethyl-1-butanol, 2,3-dimethyl-1-butanol, 3,3-dimethyl-1-butanol, 2,3-dimethyl-2-butanol, 3,3-dimethyl-2-butanol, and 2-ethyl-1-butanol. Optionally, R is 1-hexanol.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, NY 1989). Any methods, devices and materials similar or equivalent to those described herein can be used in the practice of this invention. The following definitions are provided to facilitate understanding of certain terms used frequently herein and are not meant to limit the scope of the present disclosure.

"Biological sample" or "sample" refer to materials obtained from or derived from a subject or patient. A biological sample includes sections of tissues such as biopsy and autopsy samples, and frozen sections taken for histological purposes. Such samples include bodily fluids such as blood and blood fractions or products (e.g., serum, plasma, platelets, red blood cells, and the like), sputum, tissue, cultured cells (e.g., primary cultures, explants, and transformed cells) stool, urine, synovial fluid, joint tissue, synovial tissue, synoviocytes, fibroblast-like synoviocytes, macrophage-like synoviocytes, immune cells, hematopoietic cells, fibroblasts, macrophages, T cells, etc. A biological sample is typically obtained from a eukaryotic organism, such as a mammal such as a primate e.g., chimpanzee or human; cow; dog; cat; a rodent, e.g., guinea pig, rat, mouse; rabbit; or a bird; reptile; or fish.

A "cell" as used herein, refers to a cell carrying out metabolic or other functions sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., spodoptera) and human cells. Cells may be useful when they are naturally nonadherent or have been treated not to adhere to surfaces, for example by trypsinization.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

The term "peptidyl" and "peptidyl moiety" refers to a monovalent peptide.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any appropriate method known in the art for conjugating an antibody to the label may be employed, e.g., using methods described in Hermanson, Bioconjugate Techniques 1996, Academic Press, Inc., San Diego.

A "labeled protein or polypeptide" is one that is bound, either covalently, through a linker or a chemical bond, or noncovalently, through ionic, van der Waals, electrostatic, or hydrogen bonds to a label such that the presence of the labeled protein or polypeptide may be detected by detecting the presence of the label bound to the labeled protein or polypeptide. Alternatively, methods using high affinity interactions may achieve the same results where one of a pair of binding partners binds to the other, e.g., biotin, streptavidin.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that may be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence. An amino acid residue in a protein "corresponds" to a given residue when it occupies the same essential structural position within the protein as the given residue. For example, a selected residue in a selected antibody (or Fab domain) corresponds to light chain threonine at Kabat position 40, when the selected residue occupies the same essential spatial or other structural relationship as a light chain threonine at Kabat position 40. In some embodiments, where a selected protein is aligned for maximum homology with the light chain of an antibody (or Fab domain), the position in the aligned selected protein aligning with threonine 40 is said to correspond to threonine 40. Instead of a primary sequence alignment, a three dimensional structural alignment can also be used, e.g., where the structure of the selected protein is aligned for maximum correspondence with the light chain threonine at Kabat position 40, and the overall structures compared. In this case, an amino acid that occupies the same essential position as threonine 40 in the structural model is said to correspond to the threonine 40 residue.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids sequences encode any given amino acid residue. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

"Nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acid as used herein also refers to nucleic acids that have the same basic chemical structure as a naturally occurring nucleic acid. Such analogues have modified sugars and/or modified ring substituents, but retain the same basic chemical structure as the naturally occurring nucleic acid. A nucleic acid mimetic refers to chemical compounds that have a structure that is different the general chemical structure of a nucleic acid, but that functions in a manner similar to a naturally occurring nucleic acid. Examples of such analogues include, without limitation, phosphorothiolates, phosphoramidates, methyl phosphonates, chiral-methyl phosphonates, 2-O-methyl ribonucleotides, and peptide-nucleic acids (PNAs).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, 95%, 98%, or 99% identity over a specified region, e.g., of the entire polypeptide sequences of the invention or individual domains of the polypeptides of the invention), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length. The present invention includes polypeptides that are substantially identical to any of SEQ ID NOs:1-35.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross-reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell. The level of expression of non-coding nucleic acid molecules (e.g., siRNA) may be detected by standard PCR or Northern blot methods well known in the art. See, Sambrook et al., 1989 *Molecular Cloning: A Laboratory Manual*, 18.1-18.88.

Expression of a transfected gene can occur transiently or stably in a cell. During "transient expression" the transfected gene is not transferred to the daughter cell during cell division. Since its expression is restricted to the transfected cell, expression of the gene is lost over time. In contrast, stable expression of a transfected gene can occur when the gene is co-transfected with another gene that confers a selection advantage to the transfected cell. Such a selection advantage may be a resistance towards a certain toxin that is presented to the cell. Expression of a transfected gene can further be accomplished by transposon-mediated insertion into to the host genome. During transposon-mediated insertion, the gene is positioned in a predictable manner between two transposon linker sequences that allow insertion into the host genome as well as subsequent excision. Stable expression of a transfected gene can further be accomplished by infecting a cell with a lentiviral vector, which after infection forms part of (integrates into) the cellular genome thereby resulting in stable expression of the gene.

The terms "plasmid", "vector" or "expression vector" refer to a nucleic acid molecule that encodes for genes and/or regulatory elements necessary for the expression of genes. Expression of a gene from a plasmid can occur in cis or in trans. If a gene is expressed in cis, the gene and the regulatory elements are encoded by the same plasmid. Expression in trans refers to the instance where the gene and the regulatory elements are encoded by separate plasmids.

The terms "transfection", "transduction", "transfecting" or "transducing" can be used interchangeably and are defined as a process of introducing a nucleic acid molecule or a protein to a cell. Nucleic acids are introduced to a cell using non-viral or viral-based methods. The nucleic acid molecules may be gene sequences encoding complete proteins or functional portions thereof. Non-viral methods of transfection include any appropriate transfection method that does not use viral DNA or viral particles as a delivery system to introduce the nucleic acid molecule into the cell. Exemplary non-viral transfection methods include calcium phosphate transfection, liposomal transfection, nucleofection, sonoporation, transfection through heat shock, magnetifection and electroporation. In some embodiments, the nucleic acid molecules are introduced into a cell using electroporation following standard procedures well known in the art. For viral-based methods of transfection any useful viral vector may be used in the methods described herein. Examples for viral vectors include, but are not limited to retroviral, adenoviral, lentiviral and adeno-associated viral vectors. In some embodiments, the nucleic acid molecules are introduced into a cell using a retroviral vector following standard procedures well known in the art. The terms "transfection" or "transduction" also refer to introducing proteins into a cell from the external environment. Typically, transduction or transfection of a protein relies on attachment of a peptide or protein capable of crossing the cell membrane to the protein of interest. See, e.g., Ford et al. (2001) *Gene Therapy* 8:1-4 and Prochiantz (2007) *Nat. Methods* 4:119-20.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody plays a significant role in determining the specificity and affinity of binding. In some embodiments, antibodies or fragments of antibodies may be derived from different organisms, including humans, mice, rats, hamsters, camels, etc. Antibodies of the invention may include antibodies that have been modified or mutated at one or more amino acid positions to improve or modulate a desired function of the antibody (e.g. glycosylation, expression, antigen recognition, effector functions, antigen binding, specificity, etc.).

Antibodies are large, complex molecules (molecular weight of ~150,000 or about 1320 amino acids) with intricate internal structure. A natural antibody molecule contains two identical pairs of polypeptide chains, each pair having one light chain and one heavy chain. Each light chain and heavy chain in turn consists of two regions: a variable ("V") region involved in binding the target antigen, and a constant ("C") region that interacts with other components of the immune system. The light and heavy chain variable regions come together in 3-dimensional space to form a variable region that binds the antigen (for example, a receptor on the surface of a cell). Within each light or heavy chain variable region, there are three short segments (averaging 10 amino acids in length) called the complementarity determining regions ("CDRs"). The six CDRs in an antibody variable domain (three from the light chain and three from the heavy chain) fold up together in 3-dimensional space to form the actual antibody binding site which docks onto the target antigen. The position and length of the CDRs have been precisely defined by Kabat, E. et al., Sequences of Proteins of Immunological Interest, U.S. Department of Health and Human Services, 1983, 1987. The part of a variable region not contained in the CDRs is called the framework ("FR"), which forms the environment for the CDRs.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) or light chain variable region and variable heavy chain (VH) or heavy chain variable region refer to these light and heavy chain regions, respectively. The terms variable light chain (VL) and light chain variable region as referred to herein may be used interchangeably. The terms variable heavy chain (VH) and heavy chain variable region as referred to herein may be used interchangeably. The Fc (i.e. fragment crystallizable region) is the "base" or "tail" of an immunoglobulin and is typically composed of two heavy chains that contribute two or three constant domains depending on the class of the antibody. By binding to specific proteins the Fc region ensures that each antibody generates an appropriate immune response for a given antigen. The Fc region also binds to various cell receptors, such as Fc receptors, and other immune molecules, such as complement proteins.

The term "antigen" as provided herein refers to molecules capable of binding to the antibody region provided herein, wherein the binding site is not the peptide binding site.

Antibodies exist, for example, as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region, thereby converting the F(ab)'2 dimer into an Fab' monomer. The Fab' monomer is essentially the antigen binding portion with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

A single-chain variable fragment (scFv) is typically a fusion protein of the variable regions of the heavy (VH) and light chains (VL) of immunoglobulins, connected with a short linker peptide of 10 to about 25 amino acids. The linker may usually be rich in glycine for flexibility, as well as serine or threonine for solubility. The linker can either connect the N-terminus of the VH with the C-terminus of the VL, or vice versa.

The epitope of a mAb is the region of its antigen to which the mAb binds. Two antibodies bind to the same or overlapping epitope if each competitively inhibits (blocks) binding of the other to the antigen. That is, a 1×, 5×, 10×, 20× or 100× excess of one antibody inhibits binding of the other by at least 30% but preferably 50%, 75%, 90% or even 99% as measured in a competitive binding assay (see, e.g., Junghans et al., Cancer Res. 50:1495, 1990). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

For preparation of suitable antibodies of the invention and for use according to the invention, e.g., recombinant, monoclonal, or polyclonal antibodies, many techniques known in the art can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy, Alan R. Liss, Inc. (1985); Coligan, Current Protocols in Immunology (1991); Harlow & Lane, Antibodies, A Laboratory Manual (1988); and Goding, Monoclonal Antibodies: Principles and Practice (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, Immunology (3rd ed. 1997)). Techniques for the production of single chain antibodies or recombinant antibodies (U.S. Pat. No. 4,946,778, U.S. Pat. No. 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625, 126; 5,633,425; 5,661,016, Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); and Lonberg & Huszar, Intern. Rev. Immunol. 13:65-93 (1995)). Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)). Antibodies can also be made bispecific, i.e., able to recognize two different antigens (see, e.g., WO 93/08829, Traunecker et al., EMBO J. 10:3655-3659 (1991); and Suresh et al., Methods in Enzymology 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art (e.g., U.S. Pat. Nos. 4,816,567; 5,530,101; 5,859,205; 5,585,089; 5,693,761; 5,693,762; 5,777,085; 6,180,370; 6,210,671; and 6,329,511; WO 87/02671; EP Patent Application 0173494; Jones et al. (1986) Nature 321:522; and Verhoyen et al. (1988) Science 239:1534). Humanized antibodies are further described in, e.g., Winter and Milstein (1991) Nature 349:293. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Morrison et al., PNAS USA, 81:6851-6855 (1984), Jones et al., Nature 321:522-525 (1986); Riechmann et al., Nature 332:323-327 (1988); Morrison and Oi, Adv. Immunol., 44:65-92 (1988), Verhoeyen et al., Science 239:1534-1536 (1988) and Presta, Curr. Op. Struct. Biol. 2:593-596 (1992), Padlan, Molec. Immun., 28:489-498 (1991); Padlan, Molec. Immun., 31(3):169-217 (1994)), by substituting rodent CDRs or CDR sequences for the corresponding sequences of a human antibody. Accordingly, such humanized antibodies are chimeric antibodies (U.S. Pat. No. 4,816, 567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies. For example, polynucleotides comprising a first sequence coding for humanized immunoglobulin framework regions and a second sequence set coding for the desired immunoglobulin complementarity determining regions can be produced synthetically or by combining appropriate cDNA and genomic DNA segments. Human constant region DNA sequences can be isolated in accordance with well known procedures from a variety of human cells.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of, and for use according to the invention include humanized and/or chimeric monoclonal antibodies.

A "therapeutic antibody" as provided herein refers to any antibody or functional fragment thereof that is used to treat cancer, autoimmune diseases, transplant rejection, cardiovascular disease or other diseases or conditions such as those described herein. Non-limiting examples of therapeutic antibodies include murine antibodies, murinized or humanized chimera antibodies or human antibodies including, but not limited to, Erbitux (cetuximab), ReoPro (abciximab), Simulect (basiliximab), Remicade (infliximab); Orthoclone OKT3 (muromonab-CD3); Rituxan (rituximab), Bexxar (tositumomab) Humira (adalimumab), Campath (alemtuzumab), Simulect (basiliximab), Avastin (bevacizumab), Cimzia (certolizumab pegol), Zenapax (daclizumab), Soliris (eculizumab), Raptiva (efalizumab), Mylotarg (gemtuzumab), Zevalin (ibritumomab tiuxetan), Tysabri (natalizumab), Xolair (omalizumab), Synagis (palivizumab), Vectibix (panitumumab), Lucentis (ranibizumab), and Herceptin (trastuzumab).

Techniques for conjugating therapeutic agents to antibodies are well known (see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery" in Controlled Drug Delivery ($2^{nd}$ Ed.), Robinson et al. (eds.), pp. 623-53 (Marcel Dekker, Inc. 1987); Thorpe, "Antibody Carriers Of Cytotoxic Agents In Cancer Therapy: A Review" in Monoclonal Antibodies '84: Biological And Clinical Applications, Pinchera et al. (eds.), pp. 475-506 (1985); and Thorpe et al., "The Preparation And Cytotoxic Properties Of Antibody-Toxin Conjugates", Immunol. Rev., 62:119-58 (1982)). As used herein, the term "antibody-drug conjugate" or "ADC" refers to a therapeutic agent conjugated or otherwise covalently bound to an antibody. A "therapeutic agent" as referred to herein, is a composition useful in treating or preventing a disease such as cancer.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions typically requires an antibody that is selected for its specificity for a particular protein. For example, polyclonal antibodies can be selected to obtain only a subset of antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity).
protein).

A "ligand" refers to an agent, e.g., a polypeptide or other molecule, capable of binding to a receptor.

The term "recombinant" when used with reference, for example, to a cell, a nucleic acid, a protein, or a vector, indicates that the cell, nucleic acid, protein or vector has been modified by or is the result of laboratory methods. Thus, for example, recombinant proteins include proteins produced by laboratory methods. Recombinant proteins can include amino acid residues not found within the native (non-recombinant) form of the protein or can be include amino acid residues that have been modified, e.g., labeled.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be, for example, a compound as described herein and a steric hindering chemical molecule. In embodiments contacting includes, for example, allowing a compound described herein to interact with a steric hindering chemical molecule.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

"Patient" or "subject in need thereof" refers to a living organism suffering from or prone to a disease or condition that can be treated by administration of a composition or pharmaceutical composition as provided herein. Non-limiting examples include humans, other mammals, bovines, rats, mice, dogs, monkeys, goat, sheep, cows, deer, and other non-mammalian animals. In some embodiments, a patient is human.

The terms "disease" or "condition" refer to a state of being or health status of a patient or subject capable of being treated with a compound, pharmaceutical composition, or method provided herein. In embodiments, the disease is cancer (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma).

The terms "treating", or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, include prevention of an injury, pathology, condition, or disease. In embodiments, "treating" refers to treatment of cancer.

An "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "therapeutically effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

As used herein, the term "cancer" refers to all types of cancer, neoplasm or malignant tumors found in mammals, including leukemias, lymphomas, melanomas, neuroendocrine tumors, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g., hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma. Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

As used herein, the terms "metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

"Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. In embodiments, an anti-cancer agent is a chemotherapeutic. In embodiments, an anti-cancer agent is an agent identified herein having utility in methods of treating cancer. In embodiments, an anti-cancer agent is an agent approved by the FDA or similar regulatory agency of a country other than the USA, for treating cancer.

The term "associated" or "associated with" in the context of a substance or substance activity or function associated with a disease (e.g., diabetes, cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma)) means that the disease (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma) is caused by (in whole or in part), or a symptom of the disease is caused by (in whole or in part) the substance or substance activity or function.

"Chemotherapeutic" or "chemotherapeutic agent" is used in accordance with its plain ordinary meaning and refers to a chemical composition or compound having antineoplastic properties or the ability to inhibit the growth or proliferation of cells.

The term "aberrant" as used herein refers to different from normal. When used to describe enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by using a method as described herein), results in reduction of the disease or one or more disease symptoms.

Recombinant Nucleic Acids

Provided herein are compositions which exhibit novel diagnostic capabilities and allow to rapidly add functionality to adoptive immunotherapy. The recombinant proteins provided herein are useful, inter alia, for a broad variety of therapeutic and diagnostic purposes. For example, the recombinant proteins provided herein including embodiments thereof may be used as non-invasive means to characterize chimeric antigen receptor (CAR) T cells before and/or during treatment of diseases (e.g., cancer). By adding functionality to the CAR immunoreceptors a population of patients with antigen-positive tumors can be efficiently treated and monitored irrespective of their HLA genotype. Adoptive immunotherapy using T lymphocytes that express these functionally improved tumor-specific CARs can be a powerful therapeutic strategy for the treatment of cancer and other diseases (e.g., infectious diseases (e.g., HIV infection)). Further, using the recombinant proteins provided herein including embodiments thereof allow for testing and improvement of the functionality and safety of CAR T cells.

In one aspect, an isolated nucleic acid is provided. The nucleic acid encodes a protein including (i) an antibody region including a central cavity formed by a heavy chain variable (VH) region, a light chain variable (VL) region, a heavy chain constant region (CH) and a light chain constant region (CL), wherein the central cavity forms a peptide binding site including framework region amino acid residues; and (ii) a transmembrane domain.

In another aspect, an isolated nucleic acid is provided. The nucleic acid encodes a protein including (i) an antibody region including a central cavity formed by a heavy chain variable (VH) region and a light chain variable (VL) region, wherein the central cavity forms a peptide binding site including framework region amino acid residues; and (ii) a transmembrane domain.

An "antibody region" as provided herein refers to a monovalent or multivalent protein moiety that forms part of the protein provided herein including embodiments thereof. A person of ordinary skill in the art would therefor immediately recognize that the antibody region is a protein moiety capable of binding an antigen (epitope). Thus, the antibody region provided herein may include a domain of an antibody or fragment (e.g., Fab) thereof. In embodiments, the antibody region is a protein conjugate. A "protein conjugate" a provided herein refers to a construct consisting of more than one polypeptide, wherein the polypeptides are bound together covalently or non-covalently. In embodiments, the protein conjugate includes a Fab moiety (a monovalent Fab) covalently attached to an scFv moiety (a monovalent scFv). In embodiments, the protein conjugate includes a plurality (at least two) Fab moieties. In embodiments, the polypeptides of a protein conjugate are encoded by one nucleic acid molecule. In embodiments, the polypeptides of a protein conjugate are encoded by different nucleic acid molecules. In embodiments, the polypeptides are connected through a linker. In embodiments, the polypeptides are connected through a chemical linker.

In embodiments, the antibody region includes a plurality of variable light chain domains and a plurality of variable heavy chain domains. A "variable light chain domain" as provided herein refers to a polypeptide including a light chain variable (VL) region. In embodiments, the variable light chain domain is a light chain variable (VL) region. A "variable heavy chain domain" as provided herein refers to a polypeptide including a heavy chain variable (VH) region. In embodiments, the variable heavy chain domain is a heavy chain variable (VH) region. In embodiments, each of said plurality of variable light chain domains and plurality of variable heavy chain domains is chemically different. Where the plurality of variable light chain domains and plurality of variable heavy chain domains is chemically different, each of the variable light chain domains and the variable heavy chain domains bind a different antigen (epitope). The antigens bound by chemically different variable light chain domains and different variable heavy chain domains may form part of the same protein or a different protein. In embodiments, the antigen forms part of a cancer cell. In embodiments, the antibody region includes a first variable light chain domain and a first variable heavy chain domain and a second variable light chain domain and a second variable heavy chain domain. The first variable heavy chain domain and the first variable light chain domain form a first paratope binding a first epitope and the second variable heavy chain domain and the second variable light chain domain form a second paratope binding to a second epitope, wherein the first and the second paratope are independently different. The term "paratope" refers to the antigen binding site of an antibody or fragment thereof.

In embodiments, the antibody region includes a first variable light chain domain and a first variable heavy chain domain, a second variable light chain domain and a second variable heavy chain domain, a third variable light chain domain and a third variable heavy chain domain, and a forth variable light chain domain and a forth variable heavy chain domain. The first variable heavy chain domain and the first variable light chain domain form a first paratope binding a first epitope, the second variable heavy chain domain and the second variable light chain domain form a second paratope binding to a second epitope, the third variable heavy chain domain and the third variable light chain domain form a third paratope binding a third epitope, the forth variable heavy chain domain and the forth variable light chain domain form a forth paratope binding to a second epitope, wherein the first, the second, the third and the forth paratope are independently different.

In embodiments, the first, the second, the third and the forth paratope are connected through a chemical linker. In embodiments, the chemical linker is a covalent linker, a non-covalent linker, a peptide linker (a linker including a peptide moiety), a cleavable peptide linker, a substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene or any combination thereof. Thus, a chemical linker as provided herein may include a plurality of chemical moieties, wherein each of the plurality of moieties is chemically different. In embodiments, the linker is a peptide linker. In embodiments, the peptide linker has a length of about 5- to about 15 amino acid residues.

In embodiments, the antibody region is a bispecific antibody. In embodiments, the antibody region is a tetravalent antibody. In embodiments, the antibody region is a tetravalent IgG. In embodiments, the antibody region is a dual-variable domain immunoglobulin as described in Jakob C G et al. (MAbs. 2013 May 1; 5(3): 358-363) and Byrne H et al. (Cell Volume 31, Issue 11, p 621-632, November 2013), which are hereby incorporated by reference in their entirety and for all purposes.

In embodiments, the antibody region includes SEQ ID NO:31 and SEQ ID NO:32. In embodiments, the antibody region includes SEQ ID NO:33 and SEQ ID NO:34. In embodiments, the antibody region includes SEQ ID NO:35 and SEQ ID NO:36. In embodiments, the antibody region includes SEQ ID NO:37 and SEQ ID NO:38. In embodiments, the antibody region includes SEQ ID NO:39 and SEQ ID NO:40. In embodiments, the antibody region includes SEQ ID NO:41 and SEQ ID NO:42. In embodiments, the antibody region includes SEQ ID NO:43 and SEQ ID NO:44. In embodiments, the antibody region includes SEQ ID NO:45 and SEQ ID NO:46. In embodiments, the antibody region includes SEQ ID NO:47 and SEQ ID NO:48. In embodiments, the antibody region includes SEQ ID NO:49 and SEQ ID NO:50. In embodiments, the antibody region includes SEQ ID NO:51 and SEQ ID NO:52. In embodiments, the antibody region includes SEQ ID NO:53 and SEQ ID NO:54. In embodiments, the antibody region includes SEQ ID NO:55 and SEQ ID NO:56. In embodiments, the antibody region includes SEQ ID NO:57 and SEQ ID NO:58. In embodiments, the antibody region includes SEQ ID NO:59 and SEQ ID NO:60. In embodiments, the antibody region includes SEQ ID NO:61 and SEQ ID NO:62. In embodiments, the antibody region includes SEQ ID NO:63 and SEQ ID NO:64. In embodiments, the antibody region includes SEQ ID NO:65 and SEQ ID NO:66. In embodiments, the antibody region includes SEQ ID NO:67 and SEQ ID NO:68. In embodiments, the antibody region includes SEQ ID NO:69 and SEQ ID NO:70. In embodiments, the antibody region includes SEQ ID NO:71 and SEQ ID NO:72. In embodiments, the antibody region includes SEQ ID NO:73 and SEQ ID NO:74. In embodiments, the antibody region includes SEQ ID NO:75 and SEQ ID NO:76. In embodiments, the antibody region includes SEQ ID NO:77 and SEQ ID NO:78. In embodiments, the antibody region includes SEQ ID NO:79 and SEQ ID NO:80. In embodiments, the antibody region includes SEQ ID NO:81 and SEQ ID NO:82. In embodiments, the antibody region includes SEQ ID NO:111 and SEQ ID NO:112. In embodiments, the antibody region includes SEQ ID NO:113 and SEQ ID NO:114. In embodiments, the antibody region includes SEQ ID NO:115 and SEQ ID NO:116. In embodiments, the antibody region includes SEQ ID NO:117 and SEQ ID NO:118. In embodiments, the antibody region includes SEQ ID NO:119 and SEQ ID NO:120.

The "heavy chain variable (VH) region" as provided herein is a domain which includes the variable region of a heavy chain of an antibody or a fragment thereof. Likewise, the "light chain variable (VL) region" as provided herein is a domain including the variable region of a light chain of an antibody or a fragment thereof. In embodiments, the heavy chain variable (VH) region is the variable region of the heavy chain of an antibody. In embodiments, the heavy chain variable (VH) region is the variable region of the heavy chain of an antibody fragment. In embodiments, the heavy chain variable (VH) region is the variable region of the heavy chain of a Fab. In embodiments, the light chain variable (VL) region is the variable region of the light chain of an antibody. In embodiments, the light chain variable (VL) region is the variable region of the light chain of an antibody fragment. In embodiments, the light chain variable (VL) region is the variable region of the light chain of a Fab.

In embodiments, the antibody region further includes a heavy chain constant region (CH) and a light chain constant region (CL). In embodiments, the heavy chain constant region (CH) is the constant region of the heavy chain of an antibody or fragment thereof. In embodiments, the light chain constant region (CL) is the constant region of the light chain of an antibody or fragment thereof. In embodiments, the heavy chain constant region (CH) is the constant region of a Fab. In embodiments, the light chain constant region (CL) is the constant region of the light chain of a Fab. In embodiments, the heavy chain constant region (CH) is the constant region of a F(ab)'2 dimer. In embodiments, the light chain constant region (CL) is the constant region of the light chain of a F(ab)'2 dimer. In embodiments, the antibody region includes an Fc domain. In embodiments, the antibody region is a humanized antibody region. In embodiments, the antibody region is a humanized mouse antibody region. In embodiments, the antibody region does not include an scFV antibody region. Where the antibody region does not include a scFv antibody region, the antibody region does not include a fusion protein of the variable regions of the heavy (VH) and light chains (VL) of immunoglobulins, connected with a short linker peptide.

Figure 4A:
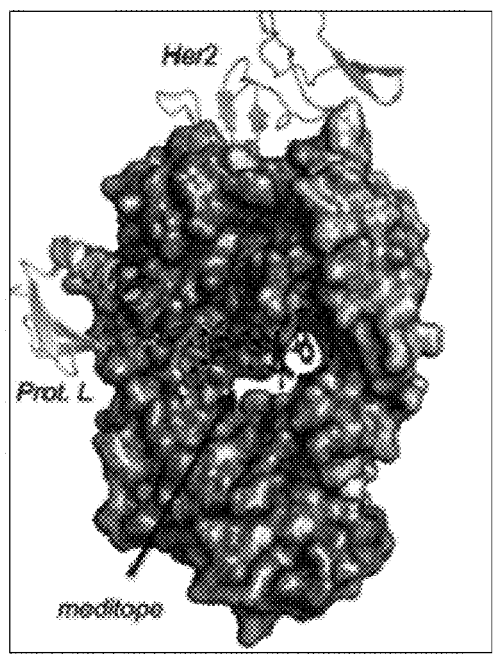
FIG. 4A-4D. Meditope Studies.
Figure 4B:
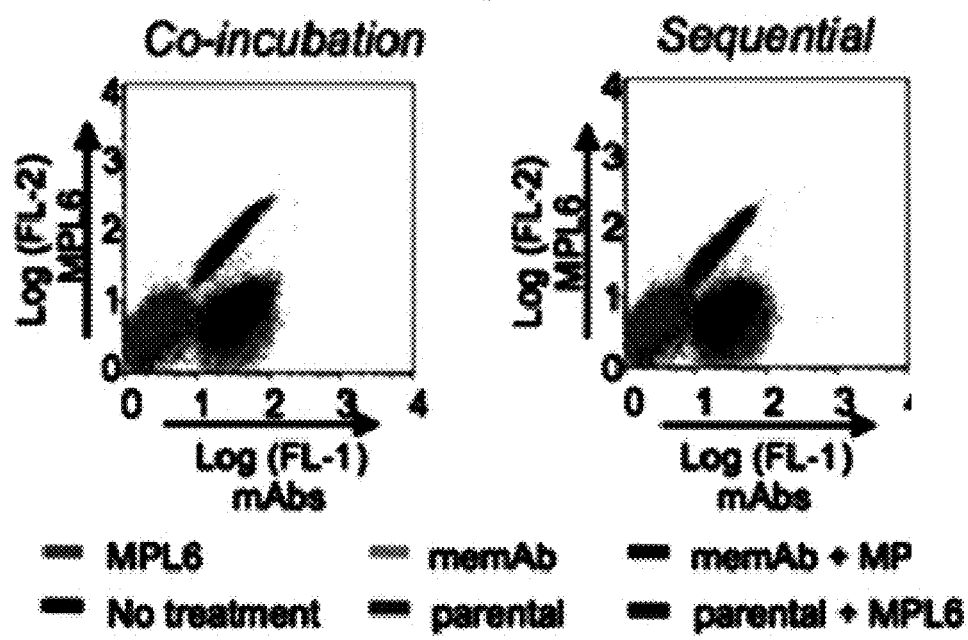
Figure 4C:
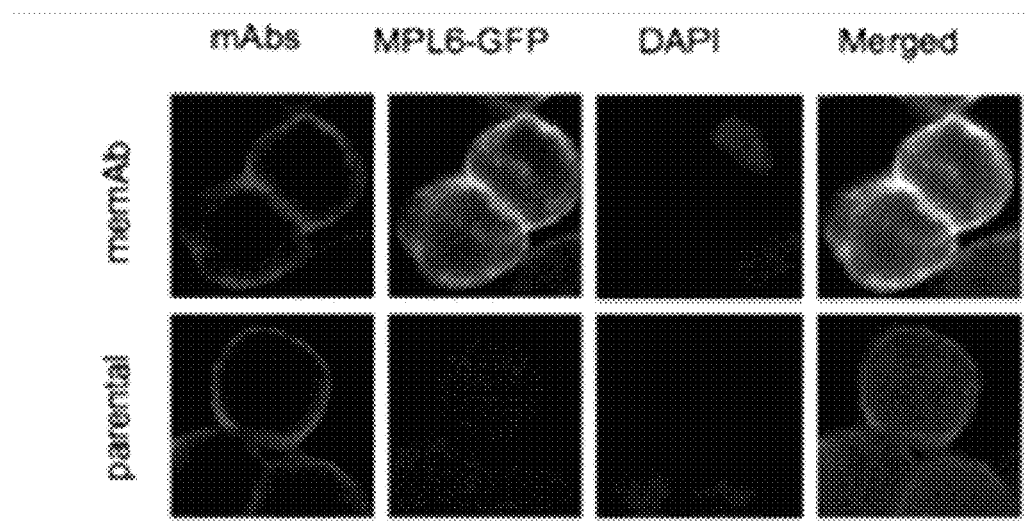
Figure 4D:
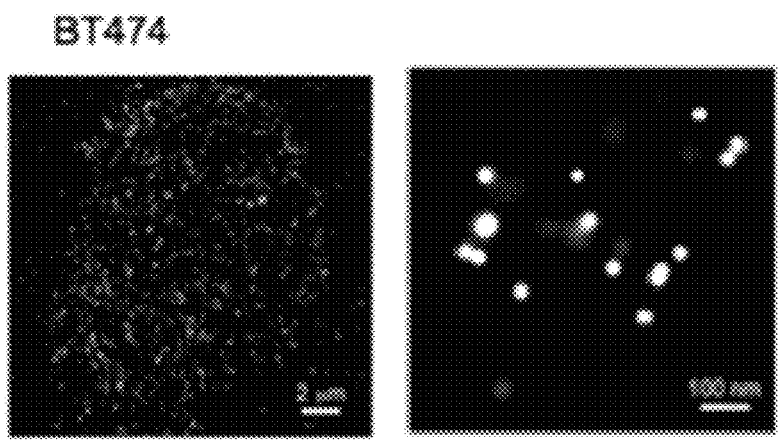

The "central cavity" with respect to the three-dimensional structure of a Fab, refers to the internal cavity of the Fab lined by portions of the heavy and light chain variable and constant regions and including amino acids lining a hole within the cavity. In embodiments, the central cavity including the hole has a structure, e.g., as depicted in, or similar to, FIG. 4A. In embodiments, where the antibody region includes a Fab, the central cavity thus is lined by residues of the VH, VL, CH1, and CL regions. The central cavity does not include the antigen binding site. Thus, in embodiments the compound that binds to the central cavity does not impact (e.g. measurably impact) the binding of the antibody region to the epitope. In other words, in embodiments, occupancy of this site does not affect antigen binding. In embodiments, the central cavity is lined by amino acid residues capable of interacting with a compound including a peptidyl moiety (e.g. a meditope) provided herein including embodiments thereof (e.g., a peptide of formula (I) or (II)). The amino acids residues capable of interacting with the compound including a peptidyl moiety (e.g. a meditope) may from part of the peptide binding site (also referred to herein as a meditope binding site). The peptide binding site may be engineered into any appropriate antibody thereby forming an antibody or antibody region with the peptide binding site (also referred to herein as a meditope enabled antibody or meditope enabled antibody region).

In embodiments, the amino acid residues lining the central cavity include a residue at a position corresponding to Kabat position 83, a residue at a position corresponding to Kabat position 30 or a residue at a position corresponding to Kabat position 52. In embodiments, the amino acid residues lining the central cavity include a residue at a position corresponding to Kabat position 40, a residue at a position corresponding to Kabat position 41, a residue at a position corresponding to Kabat position 30, a residue at a position corresponding to Kabat position 52, a residue at a position corresponding to Kabat position 83, or a residue at a position corresponding to Kabat position 85. In embodiments, the amino acid residues lining the central cavity include a residue at a position corresponding to Kabat position 40. In embodiments, the amino acid residues lining the central cavity include a residue at a position corresponding to Kabat position 41. In embodiments, the amino acid residues lining the central cavity include a residue at a position corresponding to Kabat position 30. In embodiments, the amino acid residues lining the central cavity include a residue at a position corresponding to Kabat position 52. In embodiments, the amino acid residues lining the central cavity include a residue at a position corresponding to Kabat 83. In embodiments, the amino acid residues lining the central cavity include a residue at a position corresponding to Kabat position 85.

In embodiments, the amino acid residues lining the central cavity include a residue at a position corresponding to Kabat position 30. In embodiments, the residue at a position corresponding to Kabat position 30 is a negatively charged amino acid residue. In embodiments, the residue at a position corresponding to Kabat position 30 is aspartic acid. In embodiments, the amino acid residues lining the central cavity include a residue at a position corresponding to Kabat position 52. In embodiments, the residue at a position corresponding to Kabat position 52 is a negatively charged amino acid residue. In embodiments, the residue at a position corresponding to Kabat position 52 is aspartic acid. In embodiments, the amino acid residues lining the central cavity include a residue at a position corresponding to Kabat position 83. In embodiments, the residue at a position corresponding to Kabat position 83 is a negatively charged amino acid residue. In embodiments, the residue at a position corresponding to Kabat position 83 is glutamic acid. In embodiments, the residue at a position corresponding to Kabat position 83 is isoleucine. In embodiments, the amino acid residues lining the central cavity include a residue at a position corresponding to Kabat position 85.

In embodiments, the central cavity is lined by (formed by) a light chain residue at a position corresponding to Kabat position Gln38, Thr40, Gln41, Gly42, Ser43, Asp 52, Asp85, Ile83, Tyr87, Lys103, Val163, Thr164, or Glu165. A "light chain residue" as provided herein refers to a residue forming part of a light chain of an antibody or antibody fragment. In embodiments, the central cavity is lined (e.g., formed) by a light chain residue at a position corresponding to Kabat position Gln38. In embodiments, the central cavity is lined (e.g., formed) by a light chain residue at a position corresponding to Kabat position Thr40 In embodiments, the central cavity is lined (e.g., formed) by a light chain residue at a position corresponding to Kabat position Gln41. In embodiments, the central cavity is lined (e.g., formed) by a light chain residue at a position corresponding to Kabat position Gly42. In embodiments, the central cavity is lined (e.g., formed) by a light chain residue at a position corresponding to Kabat position to Ser43. In embodiments, the central cavity is lined (e.g., formed) by a light chain residue at a position corresponding to Kabat position Asp85. In embodiments, the central cavity is lined (e.g., formed) by a light chain residue at a position corresponding to Kabat position Tyr87. In embodiments, the central cavity is lined (e.g., formed) by a light chain residue at a position corresponding to Kabat position Lys103. In embodiments, the central cavity is lined (e.g., formed) by a light chain residue at a position corresponding to Kabat position Val163. In embodiments, the central cavity is lined (e.g., formed) by a light chain residue at a position corresponding to Kabat position Thr164 In embodiments, the central cavity is lined (e.g., formed) by a light chain residue at a position corresponding to Kabat position Glu165.

In embodiments, the central cavity is lined by (formed by) a heavy chain residue at a position corresponding to Kabat position Asp 30, Gln39, Pro40, Thr91, Ala92, Ile93, Tyr95, Gln112, Leu115, Glu155, Pro156, Pro174, Ala175, or Tyr183. A "heavy chain residue" as provided herein refers to a residue forming part of a heavy chain of an antibody or antibody fragment. In embodiments, the central cavity is lined (e.g., formed) by a heavy chain residue at a position corresponding to Kabat position Gln39. In embodiments, the central cavity is lined (e.g., formed) by a heavy chain residue at a position corresponding to Kabat position. In embodiments, the central cavity is lined (e.g., formed) by a heavy chain residue at a position corresponding to Kabat position Pro40. In embodiments, the central cavity is lined (e.g., formed) by a heavy chain residue at a position corresponding to Kabat position Thr91. In embodiments, the central cavity is lined (e.g., formed) by a heavy chain residue at a position corresponding to Kabat position Ala92. In embodiments, the central cavity is lined (e.g., formed) by a heavy chain residue at a position corresponding to Kabat position Ile93. In embodiments, the central cavity is lined (e.g., formed) by a heavy chain residue at a position corresponding to Kabat position Tyr95. In embodiments, the central cavity is lined (e.g., formed) by a heavy chain residue at a position corresponding to Kabat position Gln112. In embodiments, the central cavity is lined (e.g., formed) by a heavy chain residue at a position corresponding to Kabat position Leu115. In embodiments, the central cavity is lined (e.g., formed) by a heavy chain residue at a position corresponding to Kabat position Glu155. In embodiments, the central cavity is lined (e.g., formed) by a heavy chain residue at a position corresponding to Kabat position Pro156. In embodiments, the central cavity is lined (e.g., formed) by a heavy chain residue at a position corresponding to Kabat position Pro174. In embodiments, the central cavity is lined (e.g., formed) by a heavy chain residue at a position corresponding to Kabat position Ala175. In embodiments, the central cavity is lined (e.g., formed) by a heavy chain residue at a position corresponding to Kabat position Tyr183.

The central cavity provided herein includes a peptide binding site (also referred to herein as a meditope binding site) including framework region amino acid (FR) residues. In embodiments, the peptide binding site does not include CDR residues of the heavy chain or the light chain. In embodiments, the peptide binding site includes FR residues of the heavy chain or the light chain. In embodiments, the peptide binding site includes FR residues of the heavy chain and the light chain. In embodiments, the peptide binding site includes a residue at a position corresponding to Kabat position 83, a residue at a position corresponding to Kabat position 30 or a residue at a position corresponding to Kabat position 52. In embodiments, the peptide binding site includes a residue at a position corresponding to Kabat position 40, a residue at a position corresponding to Kabat position 41, a residue at a position corresponding to Kabat position 30, a residue at a position corresponding to Kabat position 52, a residue at a position corresponding to Kabat position 83, or a residue at a position corresponding to Kabat position 85. In embodiments, the peptide binding site includes a residue at a position corresponding to Kabat position 40. In embodiments, the peptide binding site includes a residue at a position corresponding to Kabat position 41. In embodiments, the peptide binding site includes a residue at a position corresponding to Kabat position 30. In embodiments, the peptide binding site includes a residue at a position corresponding to Kabat position 52. In embodiments, the peptide binding site includes a residue at a position corresponding to Kabat position 83. In embodiments, the peptide binding site includes a residue at a position corresponding to Kabat position 85. In embodiments, residues forming a peptide binding site are described in published US application US20120301400 A1, which is hereby incorporate by reference in its entirety and for all purposes.

In embodiments, the central cavity is lined by amino acid residues capable of binding a compound including a peptidyl moiety. Thus, in embodiments, the peptide binding site provided herein is capable of binding a compound including a peptidyl moiety. In embodiments, the peptide binding site is capable of binding the peptidyl moiety. In embodiments, the peptide binding site provided herein is bound to a compound including a peptidyl moiety. In embodiments, the peptide binding site is bound to the peptidyl moiety. In embodiments, the peptidyl moiety is a moiety as described in published US application US20120301400 A1 and Avery et al. 2015 (Scientific Reports 5:7817) which are hereby incorporated by reference in their entirety and for all purposes.

In embodiments, the compound that binds to the peptide binding site is a peptide or includes a peptidyl moiety. In embodiments, the compound is a substituted peptide. In embodiments, the peptide is between 5 and 16 amino acids in length. In embodiments, the compound includes a substituted peptidyl moiety. In embodiments, the peptidyl moiety is between 5 and 16 amino acids in length. The peptide or peptidyl moiety provided herein may also be referred to as a "meditope." In embodiments, the peptide or peptidyl moiety has the formula:

X1-X2-X3-X4-X5-X6-X7-X8-X9-X10-X11-X12 (I).

Where the sequence of Formula (I) is a peptidyl moiety, a person having ordinary skill in the art will immediately understand that the peptidyl moiety is attached to the remainder of the compound at one or more attachments points. In formula (I), X1 is Cys, Gly, β-alanine, 2,3-diaminopropionic acid, β-azidoalanine, or null; X2 is Gln or null; X3 is Phe, Tyr, β-β'-diphenyl-Ala, His, Asp, 2-bromo-L-phenylalanine, 3-bromo-L-phenylalanine, 4-bromo-L-phenylalanine, Asn, Gln, a modified Phe, a hydratable carbonyl-containing residue or a boronic acid-containing residue; X4 is Asp or Asn; X5 is Leu; β-β'-diphenyl-Ala, Phe, a non-natural analog of phenylalanine, tryptophan, tyrosine, a hydratable carbonyl-containing residue or a boronic acid-containing residue; X6 is Ser or Cys; X7 is Thr, Ser or Cys; X8 is Arg, a modified (substituted) Arg, a hydratable carbonyl or a boronic acid-containing residue; X9 is Arg or Ala; X10 is Leu, Gln, Glu, β-β'-diphenyl-Ala, Phe, a non-natural analog of phenylalanine, tryptophan, tyrosine, a hydratable carbonyl-containing residue or a boronic acid-containing residue; X11 is Lys; and X12 is Cys, Gly, 7-aminoheptanoic acid, β-alanine, diaminopropionic acid, propargylglycine, isoaspartic acid or null; wherein the modified Phe is a Phe with one or more halogen incorporated into the phenyl ring and wherein the modified Arg has a structure of the formula:

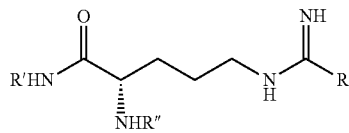

(IA). In formula (IA), R, R' and R'' are independently substituted or unsubstituted alkyl, substituted or unsubstituted aryl, substituted or unsubstituted heteroaryl, or NHR''' and R''' is substituted or unsubstituted alkyl, substituted or unsubstituted aryl, substituted or unsubstituted heteroaryl.

In embodiments, the peptide is a cyclic peptide. In embodiments, the peptidyl moiety is a cyclic peptidyl moiety. In embodiments, the peptide or peptidyl moiety includes a disulfide bridge, a thioether bridge, a lactam linkage, cycloaddition. In embodiments, the cyclic portion of the cyclic peptide or cyclic peptidyl moiety is formed through binding between X1 and X12, X1 and X11, X3 and X11, X4 and X11, or X2 and X12. In embodiments, the non-natural amino acid is β-β'-diphenyl-Ala, branched alkyl, substituted or unsubstituted aryl or substituted or unsubstituted heteroaryl. In embodiments, each of the one or more halogen is an ortho-, meta-, or para-bromo phenyl substituent.

In embodiments, the peptide or peptidyl moiety has the formula:

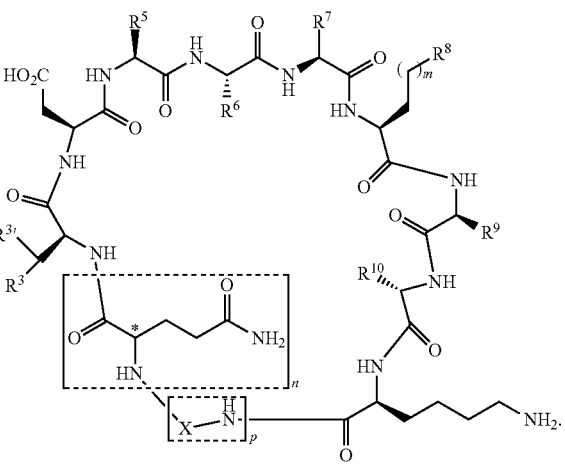

(II)

In formula (II), $R^3$ is hydrogen, $R^{3A}$-substituted or unsubstituted aryl, wherein $R^{3A}$ is hydrogen, halogen or $C_{1-4}$ unsubstituted alkyl. $R^{3'}$ is hydrogen, $R^{3A'}$-substituted or unsubstituted aryl, wherein $R^{3A'}$ is hydrogen, halogen or $C_{1-4}$ unsubstituted alkyl. $R^5$ is $R^{5A}$-substituted or unsubstituted $C_{1-8}$ (e.g., $C_{1-4}$) alkyl. $R^{5A}$ is oxo, acetal, ketal, —B(OH)$_2$, boronic ester, phosphonate ester, ortho ester, —CO$_2$C$_{1-4}$ alkyl, —CH═CH—CHO, —CH═CH—C(O)R$^{5A'}$, —CH═CH—CO$_2$R$^{5A'}$, —CO$_2$H, —CONH$_2$, or R$^{5A''}$-substituted or unsubstituted aryl, R$^{5A''}$-substituted or unsubstituted heteroaryl (e.g., naphthyl, imidazole, indole), wherein R$^{5A'}$ is substituted or unsubstituted C$_{1-4}$ alkyl and R$^{5A''}$ is —OH, fluoro, chloro, bromo or iodo. $R^6$ is -L$^{6'}$OH or -L$^{6'}$SH, wherein L$^{6'}$ is substituted or unsubstituted C$_{1-4}$ alkylene. $R^7$ is -L$^{7'}$OH or -L$^{7'}$SH, wherein L$^{7'}$ is substituted or unsubstituted C$_{1-4}$ alkyl. The symbol m is 0, 1, 2, 3, 4, or 5.

In formula (II), $R^8$ is —OH, —NR$^a$R$^b$, —N(R$^c$)C(O)R$^e$, or —N(R$^c$)C(═NR$^d$)R$^e$. R$^a$ is H. R$^b$ is H or C$_{1-8}$ alkyl optionally substituted with one or more substituents selected from the group consisting of oxo, acetal, and ketal, —B(OH)$_2$, —SH, boronic ester, phosphonate ester, ortho ester, —CH═CH—CHO, —CH═CH—C(O)C$_{1-4}$ alkyl, —CH═CH—CO$_2$C$_{1-4}$ alkyl, —CO$_2$H, or —CO$_2$C$_{1-4}$ alkyl group. R$^c$ is H, C$_{1-8}$ alkyl, C$_{3-8}$ cycloalkyl, branched alkyl, or aryl. R$^d$ is H or a C$_{1-8}$ alkyl, C$_{2-8}$ alkenyl, C$_{2-8}$ alkynyl, C$_{3-8}$ cycloalkyl, branched alkyl, or aryl group, each optionally substituted with one or more substituents selected from the group consisting of —N$_3$, —NH$_2$, —OH, —SH, halogen, oxo, acetal, ketal, —B(OH)$_2$, boronic ester, phosphonate ester, ortho ester, —CH═CH—CHO, —CH═CH—C(O)C$_{1-4}$alkyl, —CH═CH—CO$_2$C$_{1-4}$alkyl, —CO$_2$H, and —CO$_2$C$_{1-4}$ alkyl group. R$^e$ is H, —NHR$^d$; or a C$_{1-12}$ alkyl, C$_{3-8}$ cycloalkyl, C$_{2-12}$ alkenyl, C$_{2-8}$ alkynyl, or aryl group, each optionally substituted with one or more substituents selected from the group consisting of —N$_3$, —NH$_2$, —OH, —SH, oxo, $C_{2-4}$ acetal, $C_{2-4}$ ketal, —B(OH)$_2$, boronic ester, phosphonate ester, ortho ester, —CH═CH—CHO, —CH═CH—C(O)C$_{1-4}$ alkyl, —CH═CH—CO$_2$C$_{1-4}$ alkyl, and —CO$_2$C$_{1-4}$ alkyl group.

In formula (II), $R^9$ is substituted or unsubstituted $C_{1-4}$ alkyl. $R^{10}$ is $R^{10A}$-substituted or unsubstituted $C_{1-8}$ alkyl, wherein $R^{10A}$ is oxo, acetal, ketal, —B(OH)$_2$, boronic ester, phosphonate ester, ortho ester, —CH═CH—CHO, —CH═CH—C(O)C$_{1-4}$ alkyl, —CH═CH—CO$_2$C$_{1-4}$ alkyl, —CO$_2$C$_{1-4}$ alkyl, —CO$_2$H, —CONH$_2$, $R^{10B}$-substituted or unsubstituted phenyl, $R^{10B}$-substituted or unsubstituted naphthyl, $R^{10B}$-substituted or unsubstituted imidazolyl, or $R^{10B}$-substituted or unsubstituted indolyl, wherein $R^{10B}$ is —OH or halogen. The symbol n is 0 or 1. The symbol p is 0 or 1.

In formula (II), X is $R^X$-substituted or unsubstituted $C_{1-8}$ alkylene, $R^X$-substituted or unsubstituted $C_{2-8}$ alkenylene, $R^X$ is oxo, —C(O), —NH$_2$, —NHC(O) or —NHC(O)$R^y$, wherein one carbon of the alkenylene is optionally replaced with —C(O)NH, a 5-membered heteroarylene, or —S—S, and $R^y$ is —C$_{1-4}$ alkyl, —CH($R^z$)C(O) or —CH($R^z$)CO$_2$H, wherein $R^z$ is H or $R^{z'}$-substituted or unsubstituted —C$_{1-4}$ alkyl, wherein $R^{z'}$ is —OH, —SH, or —NH$_2$. Formula (I) or (II) includes all appropriate pharmaceutically acceptable salts. More information regarding the concepts of peptide binding sites (meditope binding sites) and peptides (meditopes) can be found in international application serial no. PCT/US2011/055656, PCT/US2015/053880, PCT/US2012/032938 and US application serial no. U.S. Ser. No. 14/453,586, which are hereby incorporated in their entirety and for all purposes.

The compounds provided herein may include a therapeutic agent, a diagnostic agent or a detectable agent (also referred to herein as a detectable agent) attached to the peptidyl moiety. In embodiments, the compound is conjugated to a therapeutic agent, a diagnostic agent, or a detectable agent. In embodiments, the peptidyl moiety (e.g., the peptide of formula (I) or (II)) is conjugated to a therapeutic agent, a diagnostic agent or a detectable agent. In embodiments, the antibody region is conjugated to a therapeutic agent, a diagnostic agent, or a detectable agent.

The therapeutic agent, diagnostic agent or detectable agent may be attached through a chemical linker to the compound (e.g. to the peptidyl moiety) and/or the antibody region provided herein including embodiments thereof. In embodiments, the chemical linker is a covalent linker, a non-covalent linker, a peptide linker (a linker including a peptide moiety), a cleavable peptide linker, a substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene or any combination thereof.

A chemical linker as provided herein may include a plurality of chemical moieties, wherein each of the plurality of moieties is chemically different. In embodiments, the therapeutic agent, diagnostic agent or detectable agent is attached to the compound through a non-covalent or covalent linker. In embodiments, the therapeutic agent, diagnostic agent or detectable agent is attached to the peptidyl moiety through a non-covalent or covalent linker. In embodiments, the therapeutic agent, diagnostic agent or detectable agent is attached to the antibody region through a non-covalent or covalent linker. Typically, the linker may be a covalent linker as described herein and formed through conjugate (e.g. "click") chemistry. The linker may further be a cleavable peptide linker as described herein. Where the therapeutic, diagnostic or detectable agent forms part (e.g., through covalent attachment) of the compound, the peptidyl moiety and/or the antibody region provided herein, including embodiments thereof, the therapeutic, diagnostic or detectable agent may be referred to as a "therapeutic moiety", "diagnostic moiety", or "detectable moiety", respectively. In embodiments, the peptide moiety (meditope) contains a reactive amine functionality (e.g., Lys1 1), which is used for conjugation of the meditope (peptidyl moiety), e.g., to a scaffold or linker or to a functional moiety, such as a diagnostic, e.g., imaging, agent or therapeutic moiety as described herein. In embodiments, thiol functionalities are introduced in any suitable position on the meditope (peptidyl moiety) and are selectively modified using reagents containing imagining agents, other proteins and peptides, metal chelators, siRNAs, nanoparticles, and cytotoxic drugs. Coupling of therapeutic or diagnostic moieties to the peptidyl moiety provided herein can be performed using peptide chemistry methodology well known in the art and described, for example in WO 2013055404 A1, which is hereby incorporated by reference for all purposes and its entirety.

Therapeutic moieties as provided herein may include, without limitation, peptides, proteins, nucleic acids, nucleic acid analogs, small molecules, antibodies, enzymes, prodrugs, cytotoxic agents (e.g. toxins) including, but not limited to ricin, doxorubicin, daunorubicin, taxol, ethidium bromide, mitomycin, etoposide, tenoposide, vincristine, vinblastine, colchicine, dihydroxy anthracin dione, actinomycin D, diphteria toxin, Pseudomonas exotoxin (PE) A, PE40, abrin, and glucocorticoid. In embodiments, the therapeutic moiety is an anti-cancer agent or chemotherapeutic agent as described herein. In embodiments, the therapeutic moiety is a nucleic acid moiety, a peptide moiety or a small molecule drug moiety. In embodiments, the therapeutic moiety is a nucleic acid moiety. In embodiments, the therapeutic moiety is an antibody moiety. In embodiments, the therapeutic moiety is a peptide moiety. In embodiments, the therapeutic moiety is a small molecule drug moiety. In embodiments, the therapeutic moiety is a nuclease. In embodiments, the therapeutic moiety is an immunostimulator. In embodiments, the therapeutic moiety is a toxin. In embodiments, the therapeutic moiety is a nuclease.

The compound, peptidyl moiety or antibody region provided herein may include an imaging or detectable moiety. In embodiments, the detectable moiety is connected to the compound through a covalent linker. In embodiments, the detectable moiety is connected to the antibody region through a covalent linker. In embodiments, detectable moiety is connected to peptidyl moiety through a covalent linker. An "imaging or detectable moiety" as provided herein is a monovalent compound detectable by spectroscopic, photochemical, biochemical, immunochemical, chemical, or other physical means. In embodiments, the imaging moiety is covalently attached to the compound. In embodiments, the imaging moiety is covalently attached to the antibody region. In embodiments, the imaging moiety is covalently attached to the peptidyl moiety. Exemplary imaging moieties include without limitation $^{32}$P, radionuclides, positron-emitting isotopes, fluorescent dyes, fluorophores, antibodies, bioluminescent molecules, chemoluminescent molecules, photoactive molecules, metals, electron-dense reagents, enzymes (e.g., as commonly used in an ELISA), magnetic contrast agents, quantum dots, nanoparticles, biotin, digoxigenin, haptens and proteins or other entities which can be made detectable, e.g., by incorporating a radiolabel into a peptide or antibody specifically reactive with a target peptide. Any method known in the art for conjugating an antibody to the moiety may be employed, e.g., using methods described in Hermanson, Bioconjugate Techniques 1996, Academic Press, Inc., San Diego. Exemplary fluorophores include fluorescein, rhodamine, GFP, coumarin, FITC, AlExa fluor, Cy3, Cy5, BODIPY, and cyanine dyes. Exemplary radionuclides include Fluorine-18, Gallium-68, and Copper-64. Exemplary magnetic contrast agents include gadolinium, iron oxide and iron platinum, and manganese. In embodiments, the imaging moiety is a bioluminescent molecule. In embodiments, the imaging moiety is a photoactive molecule. In embodiments, the imaging moiety is a metal. In embodiments, the imaging moiety is a nanoparticle.

A transmembrane domain as provided herein refers to a polypeptide forming part of a biological membrane. The transmembrane domain provided herein is capable of spanning a biological membrane (e.g., a cellular membrane) from one side of the membrane through to the other side of the membrane. In embodiments, the transmembrane domain spans from the intracellular side to the extracellular side of a cellular membrane. Transmembrane domains may include non-polar, hydrophobic residues, which anchor the proteins provided herein including embodiments thereof in a biological membrane (e.g., cellular membrane of a T cell). Any transmembrane domain capable of anchoring the proteins provided herein including embodiments thereof are contemplated. In embodiments, the transmembrane domain is L-selectin. The term "L-selectin" as provided herein includes any of the recombinant or naturally-occurring forms of the L-selectin protein, also known as CD62L, or variants or homologs thereof that maintain L-selectin activity (e.g. within at least 50%, 80%, 90%, 95%, 96%, 97%, 98%, 99% or 100% activity compared to L-selectin). In embodiments, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring L-selectin polypeptide. In embodiments, L-selectin is the protein as identified by the NCBI sequence reference GI:262206315, homolog or functional fragment thereof. Non-limiting examples of transmembrane domains include, the transmembrane domains of CD8, CD4 or CD3-zeta.

In embodiments, the transmembrane domain is a CD28 transmembrane domain. The term "CD28 transmembrane domain" as provided herein includes any of the recombinant or naturally-occurring forms of the transmembrane domain of CD28, or variants or homologs thereof that maintain CD28 transmembrane domain activity (e.g. within at least 50%, 80%, 90%, 95%, 96%, 97%, 98%, 99% or 100% activity compared to the CD28 transmembrane domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD28 transmembrane domain polypeptide. In embodiments, the CD28 transmembrane domain is the protein as identified by SEQ ID NO:22, SEQ ID NO:2, homolog or functional fragment thereof. In embodiments, CD28 is the protein as identified by the NCBI sequence reference GI:340545506, homolog or functional fragment thereof.

In embodiments, the transmembrane domain is the protein identified by SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, homolog or functional fragment thereof.

In embodiments, the isolated nucleic acid provided herein includes an intracellular T-cell signaling sequence encoding an intracellular T-cell signaling domain. In embodiments, the intracellular T-cell signaling domain is a CD3 ζ intracellular T-cell signaling domain. An "intracellular T-cell signaling domain" as provided herein includes amino acid sequences capable of providing primary signaling in response to binding of an antigen to the antibody region provided herein including embodiments thereof. In embodiments, the signaling of the intracellular T-cell signaling domain results in activation of the T cell expressing the same. In embodiments, the signaling of the intracellular T-cell signaling domain results in proliferation (cell division) of the T cell expressing the same. In embodiments, the signaling of the intracellular T-cell signaling domain results expression by said T cell of proteins known in the art to characteristic of activated T cell (e.g., CTLA-4, PD-1, CD28, CD69). In embodiments, the intracellular T-cell signaling domain includes the signaling domain of the zeta chain of the human CD3 complex. In embodiments, the intracellular T-cell signaling domain is a CD3 ζ intracellular T-cell signaling domain. In embodiments, the intracellular T-cell signaling domain is SEQ ID NO:11.

In embodiments, the isolated nucleic acid provided herein includes an intracellular co-stimulatory signaling sequence encoding an intracellular co-stimulatory signaling domain. An "intracellular co-stimulatory signaling domain" as provided herein includes amino acid sequences capable of providing co-stimulatory signaling in response to binding of an antigen to the antibody region provided herein including embodiments thereof. In embodiments, the signaling of the co-stimulatory signaling domain results in production of cytokines and proliferation of the T cell expressing the same. In embodiments, the intracellular co-stimulatory signaling domain is a CD28 intracellular co-stimulatory signaling domain, a 4-1BB intracellular co-stimulatory signaling domain, a ICOS intracellular co-stimulatory signaling domain, or an OX-40 intracellular co-stimulatory signaling domain. In embodiments, the intracellular co-stimulatory signaling domain includes a CD28 intracellular co-stimulatory signaling domain, a 4-1BB intracellular co-stimulatory signaling domain, a ICOS intracellular co-stimulatory signaling domain, an OX-40 intracellular co-stimulatory signaling domain or any combination thereof. Exemplary intracellular co-stimulatory signaling domains including sequences and accession numbers are listed in Table 2. In embodiments, the intracellular co-stimulatory signaling domain includes the protein identified by SEQ ID NO:12, SEQ ID NO:13, SEQ ID NO:14, SEQ ID NO:15 or SEQ ID NO:16. In embodiments, the intracellular co-stimulatory signaling domain is SEQ ID NO:12, SEQ ID NO:13, SEQ ID NO:14, SEQ ID NO:15 or SEQ ID NO:16.

In embodiments, the isolated nucleic acid provided herein includes a linker sequence encoding a linker domain. In embodiments, the linker domain is between the transmembrane domain and the intracellular T-cell signaling domain. In embodiments, the linker domain is between the intracellular T-cell signaling domain and the intracellular co-stimulatory signaling domain. In embodiments, the linker domain includes the sequence GGCGG or GGG.

In embodiments, the isolated nucleic acid provided herein includes a spacer sequence encoding a spacer region. In embodiments, the spacer region is between the transmembrane domain and the antibody region. A "spacer region" as provided herein is a polypeptide connecting the antibody region with the transmembrane domain. In embodiments, the spacer region connects the heavy chain constant region with the transmembrane domain. In embodiments, the binding affinity of the antibody region to an antigen is increased compared to the absence of the spacer region. In embodiments, the steric hindrance between an antibody region and an antigen is decreased in the presence of the spacer region.

In embodiments, the spacer region includes an Fc region. Examples of spacer regions contemplated for the compositions and methods provided herein include without limitation, immunoglobulin molecules or fragments thereof (e.g., IgG1, IgG2, IgG3, IgG4) and immunoglobulin molecules or fragments thereof (e.g., IgG1, IgG2, IgG3, IgG4) including mutations affecting Fc receptor binding. In embodiments, the spacer region is a fragment of an IgG (e.g., IgG4), wherein said fragment includes a deletion of the CH2 domain. The spacer region may be a peptide linker. In embodiments, the spacer region is a serine-glycine linker. In embodiments, the spacer region has the sequence GGSG. In embodiments, the spacer region has the sequence GSGSGSGS. In embodiments, the spacer region is at least 4 amino acids in length. In embodiments, the spacer region is about 4 amino acids in length. In embodiments, the spacer region is between 4 and 250 amino acids in length. The spacer region may include residues capable of extending the half-life in vivo (e.g., plasma) of the proteins provided herein. In embodiments, the spacer region is 10 amino acids in length. In embodiments, the spacer region is 229 amino acids in length. In embodiments, the spacer region is GGGSSGGGSG. The spacer region may be "pasylated." The term "pasylated" or "pasylation" is used in its customary sense and refers to an amino acid sequences, which due to their high content in proline, alanine and serine form highly soluble biological polymers. Thus, in embodiments, the spacer region includes about 200 proline, alanine and serine residues combined. In embodiments, the spacer region includes from about 10 to about 200 proline, alanine and serine residues combined. In embodiments, the spacer region includes hydrophilic residues. In embodiments, the recombinant protein does not include a spacer region. In embodiments, the nucleic acid does not include a spacer sequence encoding a spacer region. In embodiments, the nucleic acid does not include a spacer sequence encoding a spacer region as described in WO 2015105522 A1.

In embodiments, the nucleic acid includes (i) a heavy chain sequence encoding a heavy chain domain of the protein, the heavy chain domain includes a variable heavy chain domain and the transmembrane domain; and (ii) a light chain sequence encoding a light chain domain of the protein, the light chain domain includes a variable light chain domain, wherein the variable heavy chain domain and the variable light chain domain together form at least a portion of the antibody region.

In embodiments, the isolated nucleic acid encodes from the 5' end to 3' end: a light chain sequence, a heavy chain sequence, a transmembrane sequence and an intracellular co-stimulatory signaling sequence. In embodiments, the isolated nucleic acid encodes from the 5' end to 3' end: a heavy chain sequence, a transmembrane sequence, an intracellular co-stimulatory signaling sequence and a light chain sequence. In embodiments, the isolated nucleic acid encodes from the 5' end to 3' end: a light chain sequence, a self-cleaving peptidyl linker sequence, a heavy chain sequence, a spacer sequence, a transmembrane sequence, an intracellular co-stimulatory signaling sequence and an intracellular T-cell signaling sequence. In embodiments, the isolated nucleic acid encodes from the 5' end to 3' end: a heavy chain sequence, a spacer sequence, a transmembrane sequence, an intracellular co-stimulatory signaling sequence, an intracellular T-cell signaling sequence, a self-cleaving peptidyl linker sequence and a light chain sequence.

A "light chain sequence" as provided herein refers to the nucleic acid sequence encoding for a light chain domain provided herein. A light chain domain provided herein may include a light chain variable (VL) region and/or a light chain constant region (CL). A "heavy chain sequence" as provided herein refers to the nucleic acid sequence encoding for a heavy chain domain provided herein. A heavy chain domain provided herein may include heavy chain variable (VH) region and/or a heavy chain constant region (CH). A "transmembrane sequence" as provided herein refers to the nucleic acid sequence encoding for a transmembrane domain provided herein. An "intracellular T-cell signaling sequence" as provided herein refers to the nucleic acid sequence encoding for a intracellular T-cell signaling domain provided herein. An "intracellular co-stimulatory signaling sequence" as provided herein refers to the nucleic acid sequence encoding for a intracellular co-stimulatory signaling domain provided herein.

In embodiments, the isolated nucleic acid includes a self-cleaving peptidyl sequence encoding a self-cleaving peptidyl domain between the heavy chain sequence and the light chain sequence. In embodiments, the self-cleaving peptidyl linker sequence is a T2A sequence. In embodiments, the self-cleaving peptidyl linker sequence is a T2A sequence or a 2A sequence. In embodiments, the self-cleaving peptidyl linker sequence is a foot-and-mouth disease virus sequence. In embodiments, the self-cleaving peptidyl linker sequence is PVKQLLNFDLLKLAGD-VESNPGP (SEQ ID NO:83). In embodiments, the self-cleaving peptidyl linker sequence is an equine rhinitis A virus sequence. In embodiments, the self-cleaving peptidyl linker sequence is QCTNYALLKLAGDVESNPGP (SEQ ID NO:84). In embodiments, the self-cleaving peptidyl linker sequence is a porcine teschovirus 1 sequence. In embodiments, the self-cleaving peptidyl linker sequence is ATNFSLLKQAGDVEENPGP (SEQ ID NO:85). In embodiments, the self-cleaving peptidyl linker sequence is Thosea asigna virus sequence. In embodiments, the self-cleaving peptidyl linker sequence is EGRGSLLTCGD-VESNPGP (SEQ ID NO:86). In embodiments, the light chain sequence is 3' to the heavy chain sequence. In embodiments, the light chain sequence is 5' to the heavy chain sequence.

In embodiments, the antibody region is a cetuximab meditope enabled domain, trastuzumab meditope enabled domain, pertuzumab meditope enabled domain, M5A meditope enabled domain or rituximab meditope enabled domain. In embodiments, the antibody region is a humanized cetuximab meditope enabled domain. In embodiments, the antibody region is a humanized rituximab meditope enabled domain.

In another aspect, an isolated nucleic acid is provided. The isolated nucleic acid encodes a protein including a first portion including an antibody heavy chain variable domain and a second portion including an antibody light chain variable domain and an antibody light chain constant domain, wherein the first portion further includes a transmembrane domain. In embodiments, the protein is the protein identified by SEQ ID NO:17. In embodiments, the protein is the protein identified by SEQ ID NO:28. In embodiments, the protein is the protein identified by SEQ ID NO:98. In embodiments, the protein is the protein identified by SEQ ID NO:110.

In embodiments, the protein includes from the N-terminus to the C-terminus: a signaling peptide of SEQ ID NO:18, a heavy chain domain of SEQ ID NO:19, a hinge region of SEQ ID NO:20, a spacer region of SEQ ID NO:21, a transmembrane domain of SEQ ID NO:22, an intracellular co-stimulatory signaling domain of SEQ ID NO:23, a linker domain of SEQ ID NO:24, an intracellular T-cell signaling domain of SEQ ID NO:25, a first self-cleaving peptidyl linker domain of SEQ ID NO:26, a marker peptide of SEQ ID NO:29, a second self-cleaving peptidyl linker domain of SEQ ID NO:30, a signaling peptide of SEQ ID NO:18 and a light chain domain of SEQ ID NO:27. In embodiments, the protein includes from the N-terminus to the C-terminus: a signaling peptide of SEQ ID NO:18, a heavy chain domain of SEQ ID NO:19, a hinge region of SEQ ID NO:20, a spacer region of SEQ ID NO:21, a transmembrane domain of SEQ ID NO:22, an intracellular co-stimulatory signaling domain of SEQ ID NO:23, a linker domain of SEQ ID NO:24, an intracellular T-cell signaling domain of SEQ ID NO:25, a first self-cleaving peptidyl linker domain of SEQ ID NO:26, a marker peptide of SEQ ID NO:29, a second self-cleaving peptidyl linker domain of SEQ ID NO:30, a signaling peptide of SEQ ID NO:18 or a light chain domain of SEQ ID NO:27. In embodiments, the protein includes from the N-terminus to the C-terminus: a signaling peptide of SEQ ID NO:18, a heavy chain domain of SEQ ID NO:19, a hinge region of SEQ ID NO:20, a spacer region of SEQ ID NO:21, a transmembrane domain of SEQ ID NO:22, an intracellular co-stimulatory signaling domain of SEQ ID NO:23, a linker domain of SEQ ID NO:24, an intracellular T-cell signaling domain of SEQ ID NO:25, a self-cleaving peptidyl linker domain of SEQ ID NO:26, a signaling peptide of SEQ ID NO:18 and a light chain domain of SEQ ID NO:27. In embodiments, the protein includes from the N-terminus to the C-terminus: a signaling peptide of SEQ ID NO:18, a heavy chain domain of SEQ ID NO:19, a hinge region of SEQ ID NO:20, a spacer region of SEQ ID NO:21, a transmembrane domain of SEQ ID NO:22, an intracellular co-stimulatory signaling domain of SEQ ID NO:23, a linker domain of SEQ ID NO:24, an intracellular T-cell signaling domain of SEQ ID NO:25, a self-cleaving peptidyl linker domain of SEQ ID NO:26, a signaling peptide of SEQ ID NO:18 or a light chain domain of SEQ ID NO:27.

The term "signaling peptide" as referred to herein is used according to its ordinary meaning in the art and refers to a peptide having a length of about 5-30 amino acids. A signaling peptide is present at the N-terminus of newly synthesized proteins that form part of the secretory pathway. Proteins of the secretory pathway include, but are not limited to proteins that reside either inside certain organelles (the endoplasmic reticulum, Golgi or endosomes), are secreted from the cell, or are inserted into a cellular membrane. In embodiments, the signaling peptide forms part of the transmembrane domain of a protein.

The term "heavy chain domain" as referred to herein is used according to its ordinary meaning in the art and refers to a polypeptide including a heavy chain variable (VH) region and a heavy chain constant region (CH). The term "light chain domain" as referred to herein is used according to its ordinary meaning in the art and refers to a polypeptide including a light chain variable (VL) region and a light chain constant region (CL).

In embodiments, the protein includes from the N-terminus to the C-terminus: a signaling peptide of SEQ ID NO:87, a light chain domain of SEQ ID NO:88, a self-cleaving peptidyl linker domain of SEQ ID NO:89, a heavy chain domain of SEQ ID NO:90, a hinge region of SEQ ID NO:91, a first spacer region of SEQ ID NO:92, a second spacer region of SEQ ID NO:93, a transmembrane domain of SEQ ID NO:94, an intracellular co-stimulatory signaling domain of SEQ ID NO:95, a linker domain of SEQ ID NO:96, and an intracellular T-cell signaling domain of SEQ ID NO:97. In embodiments, the protein includes from the N-terminus to the C-terminus: a signaling peptide of SEQ ID NO:87, a light chain domain of SEQ ID NO:88, a self-cleaving peptidyl linker domain of SEQ ID NO:89, a heavy chain domain of SEQ ID NO:90, a hinge region of SEQ ID NO:91, a first spacer region of SEQ ID NO:92, a second spacer region of SEQ ID NO:93, a transmembrane domain of SEQ ID NO:94, an intracellular co-stimulatory signaling domain of SEQ ID NO:95, a linker domain of SEQ ID NO:96, or an intracellular T-cell signaling domain of SEQ ID NO:97.

In embodiments, the protein includes from the N-terminus to the C-terminus: a signaling peptide of SEQ ID NO:99, a heavy chain domain of SEQ ID NO:100, a hinge region of SEQ ID NO:101, a first spacer region of SEQ ID NO:102, a second spacer region of SEQ ID NO:103, a transmembrane domain of SEQ ID NO:104, an intracellular co-stimulatory signaling domain of SEQ ID NO:105, a linker domain of SEQ ID NO:106, and an intracellular T-cell signaling domain of SEQ ID NO:107, a self-cleaving peptidyl linker domain of SEQ ID NO:108, and a light chain domain of SEQ ID NO:109. In embodiments, the protein includes from the N-terminus to the C-terminus: a signaling peptide of SEQ ID NO:99, a heavy chain domain of SEQ ID NO:100, a hinge region of SEQ ID NO:101, a first spacer region of SEQ ID NO:102, a second spacer region of SEQ ID NO:103, a transmembrane domain of SEQ ID NO:104, an intracellular co-stimulatory signaling domain of SEQ ID NO:105, a linker domain of SEQ ID NO:106, and an intracellular T-cell signaling domain of SEQ ID NO:107, a self-cleaving peptidyl linker domain of SEQ ID NO:108, or a light chain domain of SEQ ID NO:109.

In embodiments, the first portion further includes an intracellular T-cell signaling domain. In embodiments, the intracellular T-cell signaling domain is SEQ ID NO:11. In embodiments, the intracellular T-cell signaling domain is a CD3 ζ intracellular T-cell signaling domain. In embodiments, the first portion includes an intracellular co-stimulatory signaling domain. In embodiments, the intracellular co-stimulatory signaling domain is a CD28 intracellular co-stimulatory signaling domain, a 4-1BB intracellular co-stimulatory signaling domain, a ICOS intracellular co-stimulatory signaling domain, or an OX-40 intracellular co-stimulatory signaling domain. In embodiments, the intracellular co-stimulatory signaling domain is SEQ ID NO:12, SEQ ID NO:13, SEQ ID NO:14, SEQ ID NO:15 or SEQ ID NO:16.

In embodiments, the first portion includes a linker domain. In embodiments, the linker domain is between the transmembrane domain and the intracellular T-cell signaling domain. In embodiments, the linker domain is between the intracellular T-cell signaling domain and the intracellular co-stimulatory signaling domain. In embodiments, the linker domain comprises the sequence GGCGG or GGG.

In embodiments, the first portion includes a CD3 ζ intracellular T-cell signaling domain and intracellular co-stimulatory signaling domain. In embodiments, the first portion includes from the amino terminus to the carboxy terminus: the heavy chain variable domain, a heavy chain constant domain, the transmembrane domain, the CD3 ζ intracellular T-cell signaling domain and an intracellular co-stimulatory signaling domain.

In embodiments, the isolated nucleic acid molecule provided herein includes a spacer region positioned between the heavy chain variable domain and the transmembrane domain. In embodiments, the spacer region includes a hinge region. In embodiments, the hinge region is a CD8 hinge region. In embodiments, the hinge region is a CD28 hinge region. A "spacer region" as provided herein is a polypeptide connecting the antibody heavy chain variable domain with the transmembrane domain. Where the first portion of the protein provided herein including embodiments thereof, includes a heavy chain constant domain, the heavy chain constant domain connects the heavy chain variable domain with the spacer region and the spacer region connects the heavy chain constant domain with the transmembrane domain. Thus in embodiments, the spacer region connects the heavy chain variable domain with the transmembrane domain. In embodiments, the spacer region connects the heavy chain constant domain with the transmembrane domain.

In embodiments, the antibody heavy chain variable domain and the antibody light chain variable domain are humanized. In embodiments, the first portion includes a heavy chain constant domain. In embodiments, the isolated nucleic acid includes a self-cleaving peptidyl sequence between the first portion and the second portion. In embodiments, the self-cleaving peptidyl encoding sequence is a T2A encoding sequence or a 2A encoding sequence. In embodiments, the self-cleaving peptidyl encoding sequence is a T2A encoding sequence or 2A encoding sequence. In embodiments, the nucleic acid sequence encoding the second portion is 3' to the nucleic acid sequence encoding the first portion.

In embodiments, the protein or antibody region provided herein including embodiments thereof competes for antigen binding with, specifically binds to the same antigen or epitope as, and/or contains one, more, or all CDRs (or CDRs comprising at least at or about 75, 80, 85, 90, 91, 92, 93, 94, 95, 96, 97, 98, or 99% identity to the CDRs), e.g., including a heavy chain CDR 1, 2, and/or 3 and/or a light chain CDR1, 2, and/or 3, of one or more known antibodies, including any commercially available antibody, such as abagovomab, abciximab, adalimumab, adecatumumab, alemtuzumab, altumomab, altumomab pentetate, anatumomab, anatumomab mafenatox, arcitumomab, atlizumab, basiliximab, bectumomab, ectumomab, belimumab, benralizumab, bevacizumab, brentuximab, canakinumab, capromab, capromab pendetide, catumaxomab, certolizumab, clivatuzumab tetraxetan, daclizumab, denosumab, eculizumab, edrecolomab, efalizumab, etaracizumab, ertumaxomab, fanolesomab, Fbta05, fontolizumab, gemtuzumab, girentuximab, golimumab, ibritumomab, igovomab, infliximab, ipilimumab, labetuzumab, mepolizumab, muromonab, muromonab-CD3, natalizumab, necitumumab, nimotuzumab, ofatumumab, omalizumab, oregovomab, palivizumab, panitumumab, ranibizumab, rituximab, satumomab, sulesomab, ibritumomab, ibritumomab tiuxetan, tocilizumab, tositumomab, trastuzumab, Trbs07, ustekinumab, visilizumab, votumumab, zalutumumab, and/or brodalumab; and/or anrukinzumab, bapineuzumab, dalotuzumab, demcizumab, ganitumab, inotuzumab, mavrilimumab, moxetumomab pasudotox, rilotumumab, sifalimumab, tanezumab, tralokinumab, tremelimumab, urelumab, the antibody produced by the hybridoma 10B5 (see Edelson & Unanue, Curr Opin Immunol, 2000 August; 12(4):425-31), B6H12.2 (abcam) or other anti-CD47 antibody (see Chao et al., Cell, 142, 699-713, Sep. 3, 2010).

In embodiments, the protein or antibody region specifically binds to an antigen selected from the group consisting of: CA-125, glycoprotein (GP) IIb/IIIa receptor, TNF-alpha, CD52, TAG-72, Carcinoembryonic antigen (CEA), interleukin-6 receptor (IL-6R), IL-2, interleukin-2 receptor a-chain (CD25), CD22, B-cell activating factor, interleukin-5 receptor (CD125), VEGF, VEGF-A, CD30, IL-1beta, prostate specific membrane antigen (PSMA), CD3, EpCAM, EGF receptor (EGFR), MUC1, human interleukin-2 receptor, Tac, RANK ligand, a complement protein, e.g., C5, EpCAM, CD11a, e.g., human CD11a, an integrin, e.g., alpha-v beta-3 integrin, vitronectin receptor alpha v beta 3 integrin, HER2, neu, CD3, CD15, CD20 (small and/or large loops), Interferon gamma, CD33, CA-IX, TNF alpha, CTLA-4, carcinoembryonic antigen, IL-5, CD3 epsilon, CAM, Alpha-4-integrin, IgE, e.g., IgE Fc region, an RSV antigen, e.g., F protein of respiratory syncytial virus (RSV), TAG-72, NCA-90 (granulocyte cell antigen), IL-6, GD2, GD3, IL-12, IL-23, IL-17, CTAA16.88, IL13, interleukin-1 beta, beta-amyloid, IGF-1 receptor (IGF-1R), delta-like ligand 4 (DLL4), alpha subunit of granulocyte macrophage colony stimulating factor receptor, hepatocyte growth factor, IFN-alpha, nerve growth factor, IL-13, CD326, Programmed cell death 1 ligand 1 (PD-L1, a.k.a. CD274, B7-H1), CD47, and CD137.

In embodiments, the protein or antibody region is an anti-CD19 protein, anti-CD20 protein, anti-CD22 protein, anti-CD30 protein, anti-CD33 protein, anti-CD44v6/7/8 protein, anti-CD 123 protein, anti-CEA protein, anti-EGP-2 protein, anti-EGP-40 protein, anti-erb-B2 protein, anti-erb-B2,3,4 protein, anti-FBP protein, anti-fetal acetylcholine receptor protein, anti-GD2 protein, anti-GD3 protein, anti-Her2/neu protein, anti-IL-13R-a2 protein, anti-KDR protein, anti k-light chain protein, anti-LeY protein, anti-L1 cell adhesion molecule protein, anti-MAGE-A1 protein, anti-mesothelin protein, anti-murine CMV infected cell protein, anti-MUC2 protein, anti-NKGD2 protein, anti, oncofetal antigen protein, anti-PCSA protein, anti-PSMA protein, anti-TAA (targeted by mAb IfE) protein, anti-EGFR protein, anti-TAG-72 protein or anti-VEGF-72 protein.

In embodiments, the protein or antibody region has a light chain sequence including P8, V9 or I9, I10 or L10, Q38, R39, T40, N41 G42, S43, P44, R45, D82, I83, A84, D85, Y86, Y87, G99, A100, G101, T102, K103, L104, E105, R142, S162, V163, T164, E165, Q166, D167, S168, and/or Y173, according to Kabat numbering, and/or has a heavy chain having Q6, P9, R38, Q39, S40, P41, G42, K43, G44, L45, S84, D86, T87, A88, I89, Y90, Y91, W103, G104, Q105, G106, T107, L108, V111, T110, Y147, E150, P151, V152, T173, F174, P175, A176, V177, Y185, S186, and/or L187, according to Kabat numbering.

Also provided are complexes including an antibody region or protein bound to one or more compounds including a peptidyl moiety as provided herein. The antibody region or protein may be any of the antibodies described herein including fragments thereof. The one or more compounds including a peptidyl moiety as provided herein may include any one or more of the compounds described herein, such as those described in this section, including monovalent and multivalent compounds, and labeled compounds.

In another aspect, an expression vector including a nucleic acid provided herein including embodiments thereof is provided. In embodiments, the expression vector is a viral vector. In embodiments, the virus is a lentivirus or onco-retrovirus. In embodiments, the virus is a lentivirus or onco-retrovirus.

In another aspect, a mammalian cell including the expression vector provided herein including embodiments thereof is provided. In embodiments, the mammalian cell is a natural killer (Nk) cell. In embodiments, the mammalian cell is an induced pluripotent stem cell. In embodiments, the mammalian cell is a hematopoietic stem cell. In embodiments, the mammalian cell includes a first polypeptide and a second polypeptide, the first polypeptide including a heavy chain variable domain, a heavy chain constant domain, a transmembrane domain, a CD3 ζ signaling domain and a co-stimulatory T-cell signaling domain, the second polypeptide including a light chain variable domain and a light chain constant domain.

In another aspect, a T lymphocyte including the expression vector provided herein including embodiments thereof is provided. In embodiments, the T lymphocyte includes a first polypeptide and a second polypeptide, the first polypeptide including a heavy chain variable domain, a heavy chain constant domain, a transmembrane domain, a CD3 ζ signaling domain and a co-stimulatory T-cell signaling domain, the second polypeptide including a light chain variable domain and a light chain constant domain.

Recombinant Proteins

In another aspect, a recombinant protein is provided. The recombinant protein includes (i) an antibody region including a central cavity formed by a heavy chain variable (VH) region and a light chain variable (VL) region, wherein the central cavity forms a peptide binding site including framework region amino acid residues; and (ii) a transmembrane domain. In embodiments, the antibody region further includes a heavy chain constant region (CH) and a light chain constant region (CL). In embodiments, the antibody region includes an Fc domain. In embodiments, the antibody region is a humanized antibody region (e.g. a humanized mouse antibody region). In embodiments, the antibody region does not include a scFv antibody region.

In embodiments, the protein further includes an intracellular T-cell signaling domain as described herein. In embodiments, the intracellular T-cell signaling domain is a CD3 ζ intracellular T-cell signaling domain. In embodiments, the protein further includes an intracellular co-stimulatory signaling domain. In embodiments, the intracellular co-stimulatory signaling domain is a CD28 intracellular co-stimulatory signaling domain, a 4-1BB intracellular co-stimulatory signaling domain, a ICOS intracellular co-stimulatory signaling domain, or an OX-40 intracellular co-stimulatory signaling domain.

In embodiments, the protein further includes a spacer region. In embodiments, the spacer region is between the transmembrane domain and the antibody region.

In embodiments, the protein further includes a linker domain. In embodiments, the linker domain is between the transmembrane domain and the intracellular T-cell signaling domain. In embodiments, the linker domain is between the intracellular T-cell signaling domain and the intracellular co-stimulatory signaling domain. In embodiments, the linker domain includes the sequence GGCGG or GGG. In embodiments, the antibody region is a cetuximab meditope enabled domain, trasuzumab meditope enabled domain, pertuzumab meditope enabled domain, M5A meditope enabled domain or rituximab meditope enabled domain. In embodiments, a compound including an peptidyl moiety is bound to the peptide binding site. In embodiments, the compound is a multivalent meditope. A "multivalent meditope" as provided herein is a peptidyl moiety as described herein. Thus, a multivalent meditope is capable of binding the peptide binding site provided herein including embodiments thereof. In embodiments, the multivalent meditope binds to the FR lining the peptide binding site. In embodiments, the multivalent meditope is bound to therapeutic or diagnostic moiety through a chemical linker. In embodiments, the multivalent meditope has the structure of formula (I) or (II). The proteins and compounds may be any of the protein or compounds described herein including embodiments thereof.

In another aspect, a recombinant protein is provided. The recombinant protein includes a first portion including an antibody heavy chain variable domain and a second portion including an antibody light chain variable domain and an antibody light chain constant domain, wherein the first portion further includes a transmembrane domain, and wherein the antibody heavy chain variable domain, the antibody light chain variable domain and the antibody light chain constant domain together form an antibody region.

In another aspect, a mammalian cell including the recombinant protein provided herein including embodiments thereof is provided, wherein the transmembrane domain is within the cell membrane of the mammalian cell. In embodiments, the mammalian cell is a natural killer (Nk) cell. In embodiments, the mammalian cell is an induced pluripotent stem cell. In embodiments, the mammalian cell is a hematopoietic stem cell.

In another aspect, a T lymphocyte including the recombinant protein provided herein including embodiments thereof is provided, wherein the transmembrane domain is within the cell membrane of the T lymphocyte.

Pharmaceutical Compositions

Pharmaceutical compositions provided by the present invention (e.g., proteins and compounds provided herein) include compositions wherein the active ingredient (e.g. compositions described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, the recombinant proteins described herein will contain an amount of active ingredient effective to achieve the desired result, e.g., modulating the activity of a target molecule, and/or reducing, eliminating, or slowing the progression of disease symptoms. Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of cancer and severity of such symptoms), kind of concurrent treatment, complications from the disease being treated or other health-related problems. Other therapeutic regimens or agents can be used in conjunction with the methods and compounds of the invention. Adjustment and manipulation of established dosages (e.g., frequency and duration) are well within the ability of those skilled in the art.

For any composition (e.g., recombinant protein, nucleic acid) provided herein, the therapeutically effective amount can be initially determined from cell culture assays. Target concentrations will be those concentrations of active compound(s) that are capable of achieving the methods described herein, as measured using the methods described herein or known in the art. As is well known in the art, effective amounts for use in humans can also be determined from animal models. For example, a dose for humans can be formulated to achieve a concentration that has been found to be effective in animals. The dosage in humans can be adjusted by monitoring effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to affect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred "Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

The pharmaceutical preparation is optionally in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The unit dosage form can be of a frozen dispersion.

Methods of Treatment

In another aspect, a method of treating cancer is provided. The method includes administering to a subject in need thereof an effective amount of the mammalian cell provided herein including embodiments thereof, wherein the antibody region is an anti-cancer antibody region.

In another aspect, a method of treating cancer is provided. The method includes administering to a subject in need thereof an effective amount of the T-lymphocyte provided herein including embodiments thereof, wherein the antibody region is an anti-cancer antibody region. In embodiments, the T-lymphocyte is an autologous T-lymphocyte. In embodiments, the T-lymphocyte is a heterologous T-lymphocyte. In embodiments, the cancer is a solid tumor cancer or hematologic malignancy. In embodiments, the cancer is ovarian cancer, renal cell carcinoma, a B-cell malignancy, leukemia, lymphoma, breast cancer, colorectal cancer, prostate cancer, neuroblastoma, melanoma, medulloblastoma, lung cancer, osteosarcoma, glioblastoma or glioma. In embodiments, the leukemia is acute lymphoid leukemia. In embodiments, the leukemia is chronic lymphocytic leukemia. In embodiments, the leukemia is acute myeloid leukemia. In embodiments, the leukemia is chronic myeloid leukemia.

In another aspect, a method of reprogramming a T lymphocyte is provided. The method includes contacting a T lymphocyte with the expression vector provided herein including embodiments thereof.

In another aspect, a method of detecting a cancer is provided. The method includes (i) administering to a cancer patient an effective amount of a T lymphocyte including the recombinant protein provided herein including embodiments thereof and a compound including a peptidyl moiety capable of binding to the peptide binding site, wherein the compound further includes a detectable label, and wherein the antibody region is an anti-cancer antibody region. The method includes (ii) allowing the compound to bind to the peptide binding site thereby forming a recombinant protein-compound complex. And (iii) the recombinant protein-compound complex is detected within the cancer patient thereby detecting the cancer.

As used herein, "treatment" or "treating," or "palliating" or "ameliorating" are used interchangeably herein. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made. Treatment includes preventing the disease, that is, causing the clinical symptoms of the disease not to develop by administration of a protective composition prior to the induction of the disease; suppressing the disease, that is, causing the clinical symptoms of the disease not to develop by administration of a protective composition after the inductive event but prior to the clinical appearance or reappearance of the disease; inhibiting the disease, that is, arresting the development of clinical symptoms by administration of a protective composition after their initial appearance; preventing re-occurring of the disease and/or relieving the disease, that is, causing the regression of clinical symptoms by administration of a protective composition after their initial appearance. For example, certain methods herein treat cancer (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma). For example certain methods herein treat cancer by decreasing or reducing or preventing the occurrence, growth, metastasis, or progression of cancer; or treat cancer by decreasing a symptom of cancer. Symptoms of cancer (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma) would be known or may be determined by a person of ordinary skill in the art.

As used herein the terms "treatment," "treat," or "treating" refers to a method of reducing the effects of one or more symptoms of a disease or condition characterized by expression of the protease or symptom of the disease or condition characterized by expression of the protease. Thus in the disclosed method, treatment can refer to a 10%, 20%, 30%, 40%, 50%, 60%, 70%, 80%, 90%, or 100% reduction in the severity of an established disease, condition, or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition. Further, as used herein, references to decreasing, reducing, or inhibiting include a change of 10%, 20%, 30%, 40%, 50%, 60%, 70%, 80%, 90% or greater as compared to a control level and such terms can include but do not necessarily include complete elimination.

An "effective amount" is an amount sufficient to accomplish a stated purpose (e.g. achieve the effect for which it is administered, treat a disease, reduce enzyme activity, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme or protein relative to the absence of the antagonist. A "function disrupting amount," as used herein, refers to the amount of antagonist required to disrupt the function of an enzyme or protein relative to the absence of the antagonist. Guidance can be found in the literature for appropriate dosages for given classes of pharmaceutical products. For example, for the given parameter, an effective amount will show an increase or decrease of at least 5%, 10%, 15%, 20%, 25%, 40%, 50%, 60%, 75%, 80%, 90%, or at least 100%. Efficacy can also be expressed as "-fold" increase or decrease. For example, a therapeutically effective amount can have at least a 1.2-fold, 1.5-fold, 2-fold, 5-fold, or more effect over a control. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols.

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In embodiments, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

"Anti-cancer agent" is used in accordance with its plain ordinary meaning and refers to a composition (e.g. compound, drug, antagonist, inhibitor, modulator) having anti-neoplastic properties or the ability to inhibit the growth or proliferation of cells. In embodiments, an anti-cancer agent is a chemotherapeutic. In embodiments, an anti-cancer agent is an agent identified herein having utility in methods of treating cancer. In embodiments, an anti-cancer agent is an agent approved by the FDA or similar regulatory agency of a country other than the USA, for treating cancer.

The compositions described herein can be used in combination with one another, with other active agents known to be useful in treating a cancer such as anti-cancer agents.

Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin (including recombinant interleukin II, or r1L.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-azaepothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, lnanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, lso-eleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™) erlotinib (Tarceva™), cetuximab (Erbitux™), lapatinib (Tykerb™), panitumumab (Vectibix™) vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like. In embodiments, the compositions herein may be used in combination with adjunctive agents that may not be effective alone, but may contribute to the efficacy of the active agent in treating cancer.

In embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In embodiments, co-administration can be accomplished by co-formulation, i.e., preparing a single pharmaceutical composition including both active agents. In embodiments, the active agents can be formulated separately. In embodiments, the active and/or adjunctive agents may be linked or conjugated to one another.

EXAMPLES

Applicants have discovered a unique binding site for a cyclic peptide (also referred to herein as a "meditope") within the central cavity of the Fab arm of the therapeutic mAb, cetuximab (1). Applicants demonstrated that this site is unique to cetuximab and absent in human mAbs. Applicants have also shown, biochemically and in cell culture and in animal xenograft studies, that occupancy of this site does not affect antigen binding. Moreover, Applicants demonstrated that this site can be grafted onto human mAbs ("meditope-enabling"), indicating that this peptide binding site may for example be used as a beacon for targeting imaging agents or as a "hitch" to tether new functionality to mAbs. Through extensive engineering, Applicants have improved the affinity of the meditope-Fab interaction by over 40,000-fold with an estimated half-life that exceeds six days at room temperature. Applicants further demonstrated that the fusion of the meditope to protein L, a Fab-binding protein, significantly improved the affinity and estimated the half-life of this complex to exceed 80 days. Finally, Applicants verified through SPR studies that conjugation of fluorescent markers, DOTA, GFP and other protein domains to the high affinity meditope and to the meditope-protein L (MPL) fusion do not affect the affinity of the MPL-Fab nor the Fab-antigen interactions. Collectively, these data show that functionality can be "snapped" on to any given meditope-enabled mAb.

CAR T cell therapy, which has produced durable responses especially in B cell malignancies(2-6), involves the reprogramming of patient T cells with an artificial receptor consisting of an extracellular antigen targeting moiety, a transmembrane domain and intracellular signaling modules, including CD3ζ and costimulatory domains of CD28 and/or CD137 (4-1BB), to activate the T cell and elicit an immune response. The antigen-targeting domain of the CAR generally is a tumor antigen recognizing single chain F variable antibody region (scFv). There is a need in the art for the ability to: 1) characterize the density of the CARs on the transformed cells, 2) to track administered CAR T cells at any point during the therapy and correlate this distribution to therapeutic outcomes, 3) to rapidly functionalize CAR T cells, and 4) to selectively eliminate CAR T cells if necessary. In embodiments, the constructs provided herein are capable of meeting these needs.

In embodiments, the constructs provided herein are useful in the following areas: (i) Application of super resolution microscopy to characterize CAR expression through direct observation of the receptor distribution on the T cells. Applicants have fused a photo-activatable GFP (paGFP) to a high affinity meditope, and demonstrated that meditope-enabled mAbs bound to cell-derived receptors can be "counted" and their cluster size can be quantified. Such information can be correlated with therapeutic efficacy and used in the clinic for "quality control." (ii) Imaging of meditope-enabled CAR T cells with a DOTA-conjugated, high affinity meditope in situ. Applicants have demonstrated that high affinity, conjugated meditopes do not affect antigen binding. Thus, meCAR T cells can be pre-labeled with $^{64}$Cu-DOTA-conjugated, high affinity meditopes and their migration can be traced. Alternatively, meCAR T cells can be administered, allowed to localize and proliferate, and then subsequently imaged. Pre-targeted, mAb-based imaging methods as proposed have been demonstrated to produce high quality PET images using engineered antibodies (9-11). (iii) Novel orthogonal functionality that can be rapidly added to the meCAR T cell. Specifically, meditopes may be conjugated to biologics that recognize a second tumor-associated ligand, potent cytotoxins, immune modulators including cytokines, and tumor-activated prodrugs. These meditopes may be directly attached to the meCAR T cells before administration or subsequently added after the meCAR T cells are established.

Example 1

Generation, Characterization and Identification of Meditope-Enabled CAR Constructs for Immunotherapy Different combinations of meditope-enabled Fab- and mAb-based CAR (meCAR) constructs that target HER2 positive tumors are generated, packaged each into a lentivirus, and transduced T-cells to generate meditope-enabled HER2+-CAR (meHER2+-CAR) T cells. The expression levels of each meCAR are characterized as well as its affinity for soluble extracellular HER2 with and without a DOTA-conjugated meditope. Finally, the tumor cell killing ability of each construct is quantified in the presence and absence of a DOTA-conjugated meditope in vitro.

CARs are a tool in the reprogramming of the immune system to recognize and destroy cancer cells. CARs are generally composed of an antigen recognition domain (e.g., an scFv), a spacer (e.g., the Fc domain of an IgG or hinge domain of CD8), a transmembrane region and intracellular costimulatory and activation domains (e.g., CD28 and/or CD137 and CD3 ζ chain). In embodiments, an antigen recognition domain composed of a meditope-enabled Fab or mAb provides a unique peptide binding site to rapidly and specifically add new functionality through the peptide without recourse to extensive re-engineering of the CAR itself. As noted, these functionalities may include the ability to image, target additional tumor-associated receptors, modulate immune function and selectively kill the CAR T cell. Provided herein are several expression plasmids for trastuzumab, an anti-HER2 mAb that is in the clinic for HER2 positive tumors and which Applicants have meditope-enabled (1). The order of light and heavy chain expression are altered and the efficacy of different internal ribosome entry sites versus the self-cleaving 2A peptide sequence (15) are tested. The binding of soluble HER2 are quantified as well as meditope for each construct using a variety of binding assays and super resolution microscopy. The in vitro functionality of the different CAR constructs are characterized by evaluating in vitro HER2-dependent T cell killing, degranulation, cytokine production and proliferation. The effect of meditope occupancy of the meCAR T cells are characterized using these same assays. A canonical HER2-specific CAR based on the scFv of trastuzumab are generated and characterized, which may serve as a reference point for both expression and functional assays.

A number of tumors aberrantly express HER2 including breast cancer, sarcomas, and lung cancer. Thus, there have been efforts in developing effective therapeutics, trastuzumab being one. However, 70% of HER2+ cancer patients do not respond to these systemic therapies and in fact may rapidly develop resistance to these agents (16). As such, vaccines to HER2 as well as HER2+ CAR T cells have been developed to go beyond the inhibition of HER2 signaling pathways and elicit a powerful immune response. Given the potency of CAR T cells and the possibility of adverse side effects (17), it is useful to monitor, modulate and potentially destroy HER2+ CAR T cells. Enabling CAR T cell with a meditope binding site addresses these problems.

Meditope Interaction and Optimization.

Figure 2A:
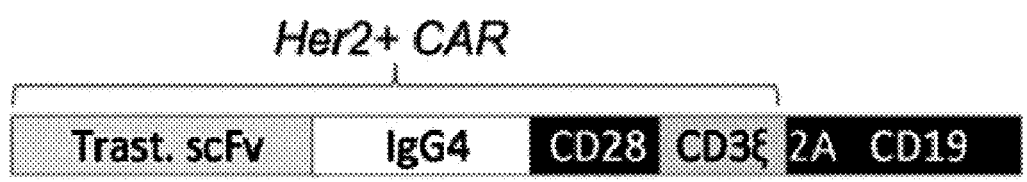
FIG. 2A-FIG. 2B: HER2-specific CAR.

Described herein is a unique peptide binding site within the Fab arm of cetuximab including unique amino acid residues lining the site not found in human antibodies. This site may be grafted onto human mAbs including trastuzumab, a humanized anti-CEA, and other mAbs. Peptide binding does not affect the ability of the meditope-enabled antibodies to bind to their antigens. Due to the position of the binding site being in the central cavity of the Fab, the peptide may be referred to as a "meditope" ("medius" and "topo") (FIG. 2A). Meditope-enabled antibodies "memAbs" refer to meditope-enabled Fabs as meFabs (1).

Figure 2B:
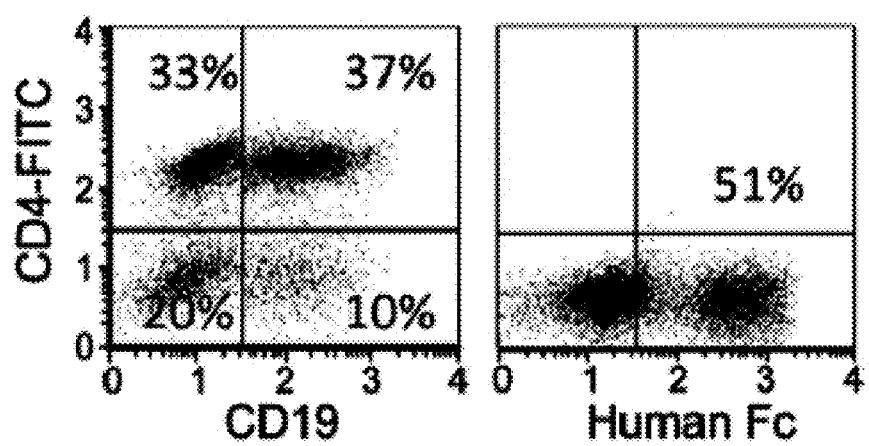

Multiple of meditope variants have been produced, their affinity measure and crystallographic data accumulated for each. In these studies critical residues were identified, non-natural amino acids as well as D-amino acids were introduced, and different cyclization strategies to significantly improve the binding affinity were used(FIG. 2B). Further, point mutations were introduced in the Fab at the meditope-binding interface (version 2) and observed a 100 fold increase in the binding affinity (FIG. 2B). Through these modifications, the affinity of meditopes increase from 1.2 μM to 860 pM at 37° C. (1000-fold increase). In addition, the termini of the meditope and protein L are, in embodiments, in close proximity when bound to the trastuzumab meFab (FIG. 2A) and demonstrated favorable avidity through the fusion of meditope to protein L through a short linker (MPL). The affinity of the MPL construct for the original trastuzumab meFab as measured by Kinexa experiments is $K_D$=14 pM, or 87,000-fold over the affinity of the individual components at 25° C. (data not shown). Assuming that each modification acts independently, a 258 million-fold increase in affinity for the combination of a synthetic MPL and the memAb. Fusion of GFP to the MPL construct does not affect memAb binding and the GFP-MPL binding to memAb does not affect the association or dissociation kinetics or the affinity of HER2 binding (as shown in Avery et al. (37)).

Alexa Fluor 647-labeled MPL was either co-administered with Alexa Fluor 488-labeled memAb to HER2 overexpressing SKBR3 cells or after the cells were treated with the memAb and extensively washed. In both cases, the labeled MPL colocalized with the memAb and antigen (data not shown). In addition, it was demonstrated by fluorescence microscopy that the fusion of the bulky GFP to the MPL does not affect cell binding (data not shown). Lastly, a photoactivatable GFP was fused to the MPL construct and super-resolution microscopy was used to quantify HER2 receptors on BT474 cells (data not shown).

HER2-Specific scFv-Derived CAR T Cells Target and Kill HER2-Positive Tumors.

Figure 3A:
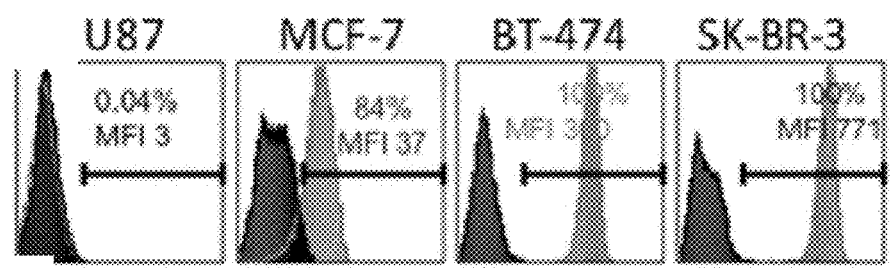
FIG. 3A-3B. HER2-28ζ Tcm kill both high and low expressing HER2 targets.
Figure 3B:
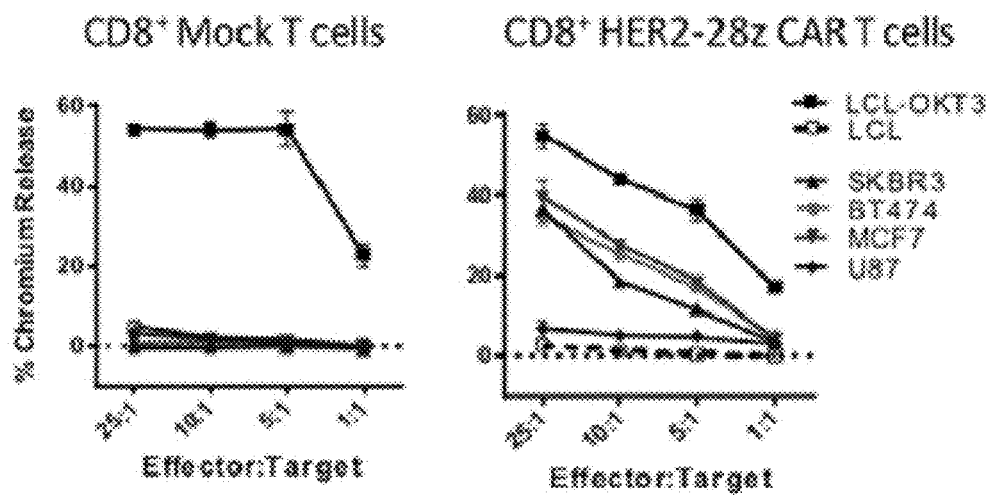

A second-generation HER2-specific CAR was generated composed of an scFv based on the trastuzumab antibody and intracellular signaling domains of CD28 and CD3ζ. A self-inactivating (SIN) lentiviral vector cassette was constructed encoding this HER2-specific scFv CAR (HER2-28ζ), followed by a 2A ribosomal skip sequence and a truncated CD19 (CD19t), an inert cell surface marker devoid of intracellular signaling that allows for specific detection of transduced T cells (FIG. 3A). The truncated CD19 (CD19t) as provided herein is also referred to as "marker peptide". The terms "marker peptide" or "tCD19" may be used interchangeably throughout. A human central memory T cells (Tcm) was constructed to express the HER2-2ζCAR and CD19t polypeptides via lentiviral transduction, and expanded ex vivo using CD3/CD28ζ Dynabeads® stimulation and growth in X-Vivo media supplemented with IL-2 and IL-15 as per cGMP-compatible manufacturing platform (FIG. 3B) (18).

Using mouse and non-human primate models relevant for human translation, it has been observed that T cells derived from $CD62L^+$ Tcm persist in the blood after adoptive transfer, migrate to memory T cell niches in the lymph nodes and bone marrow, re-acquire phenotypic properties of memory T cells, and respond to antigen challenge in vivo (21, 22, 24, 25). Tcm or CD62L+ memory/naïve T cells may be engineered to express meditope-enabled HER2-CARs, taking advantage of the intrinsic long-term persistence of memory T cells, and the cGMP-compatible manufacturing platform which has been used to produce clinical products for two phase I clinical trials (BB-INDs 14645 and 15490) (18).

HER2-28ζ Tcm exhibit potent HER2-specific cytolytic activity in vitro against a panel of target cell lines that display both low (MCF7) and high (BT-474 and SK-BR-3) HER2 expression levels (FIG. 4A-4D). Additionally, intracranial injection of HER2-28ζ Tcm can mediate regression of established brain tumors derived from the BT-474 HER2+ breast tumor cell line, and result in long term survival for 100% of the mice (data not shown).

Figure 5:
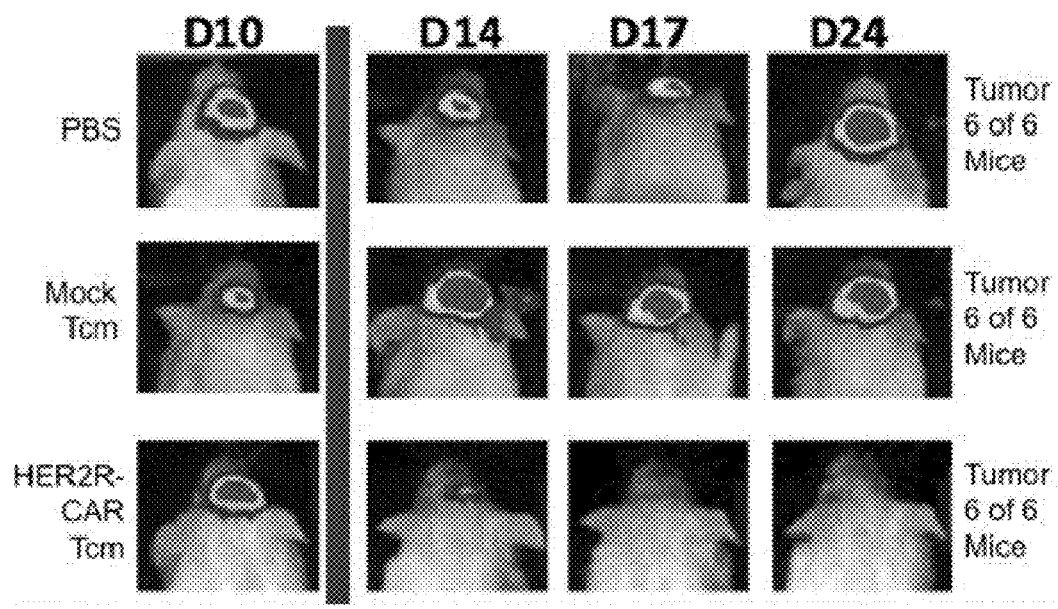
FIG. 5. HER2-scFv-CAR Tcm anti-tumor activity against intracranial engrafted breast tumors. Representative therapeutic responses to i.c. engrafted BT474 EGFP-ffLuc+ tumors ($1 \times 10^5$ cells) following intratumoral i.c. injection of HER2R-CAR T cells in NSG mice. On day 11, mice received either $1 \times 10^6$ HER2R Tcm, mock Tcm or PBS.

The synthetic meditope-enabled trastuzumab heavy and the light chains may be subcloned into a lentiviral expression vector (FIG. 5). Since each chain must be produced individually, an IRES motif will be incorporated between the light and heavy chain or use of a ribosomal skip sequence such as the T2A or the 2A sequence [15]. Further, a monomeric CAR using a meditope-enabled Fab may be created. Thus, the monomeric meditope-enabled Fab may be crosslinked with a bivalent meditope, allowing to regulation of the activity of the CAR T cell (FIG. 5). The transmembrane domain is replaced with monomeric L-selectin (26) and a simple poly glycine-serine linker is used.

Meditope-enabled CAR T cells. Primary human T cells, for example CD62L+ Tcm cells, will be isolated from the peripheral blood of at least three healthy donors, engineered by lentiviral transduction to express HER2-CARs, and evaluated in vitro for specificity and functional activity. Following expansion of meditope-enabled HER2+ CAR Tcm with OKT3/CD28 Dynabead® and cytokine (IL-2 and IL-15) stimulation, the expression level of each construct will be characterized by FACS using anti-CD19 as a marker of cell transduction and anti-Fc for CAR expression, an Alexa fluor 488-labeled, extracellular Her2-Fc construct for antigen binding, and an Alexa fluor 647-conjugated meditope for functional meditope-CAR docking. Positive CAR T cells will be enriched, if necessary, by anti-CD19 magnetic cell selection or FACS. The ability of each construct, meditope-enabled Fab and meditope enabled mAb, to target and lyse HER2-positive (low and high HER2-expressing tumor lines; FIG. 3A) and -negative breast cancer cell lines will be examined using standard chromium-release assays, and long-term co-culture assays (24-96 hrs) in the presence and absence of a DOTA-conjugated, high affinity meditope. To examine the effector function of different HER2-CAR T cells, HER2-dependent cytokine production will be measured, including secretion of IFNγ and TNFα following co-culture with tumor cells, again in the presence and absence of a DOTA-conjugated, high affinity meditope. Additionally, markers of activation and cytolytic activity will be included, namely CD69, Granzyme-B, and CD107a, as well as markers of cellular exhaustion, including PD-1. Furthermore, the antigen-dependent proliferative capacity of the different meditope-enabled HER2-CAR T cells in the presence and absence of DOTA-conjugated meditope will be measured by flow cytometry dye dilution analysis using CSFE. In each case, the results will be compared to the scFv CAR T cell. Methodologies for performing these in vitro functional assays are readily established in our group(6, 27).

Super resolution microscopy and autocorrelation analysis (28) will be used to investigate the distribution of receptors for each meditope-enabled CAR T cell. This approach will allow to quantitatively determine the size, occupancy, and density of proteins in the clusters. As demonstrated herein, an ultra-high affinity paGFP-MPL construct was produced and super resolution microscopy was utilized to detect single molecules with 15 nm resolution. In addition, a fluorescently labeled, high affinity 15-mer meditope was produced, which is less sterically constrained than the paGFP-MPL for super-resolution imaging. Using these reagents, ~12 individual cells expressing the meditope-enabled Fab or mAb will be analyzed and the efficacy of the meCAR T cell will be correlated with receptor distribution.

Example 2

Efficacy and In Vivo Imaging of Meditope-Enabled CAR in Animal Models

The efficacy of meditope-enabled CAR T cells on tumor growth inhibition will be evaluated and PET will be used to image meHER2+-CAR T cells pre-treated with $^{64}$Cu-labeled, DOTA-conjugated meditopes in NSG mice. NSG mice will be treated with the meHER2-CAR T cells and $^{64}$Cu labeled, DOTA-conjugated meditope will be administered at defined time points to assess meditope uptake by the meHER2-CAR T cells in situ.

Figure 6:
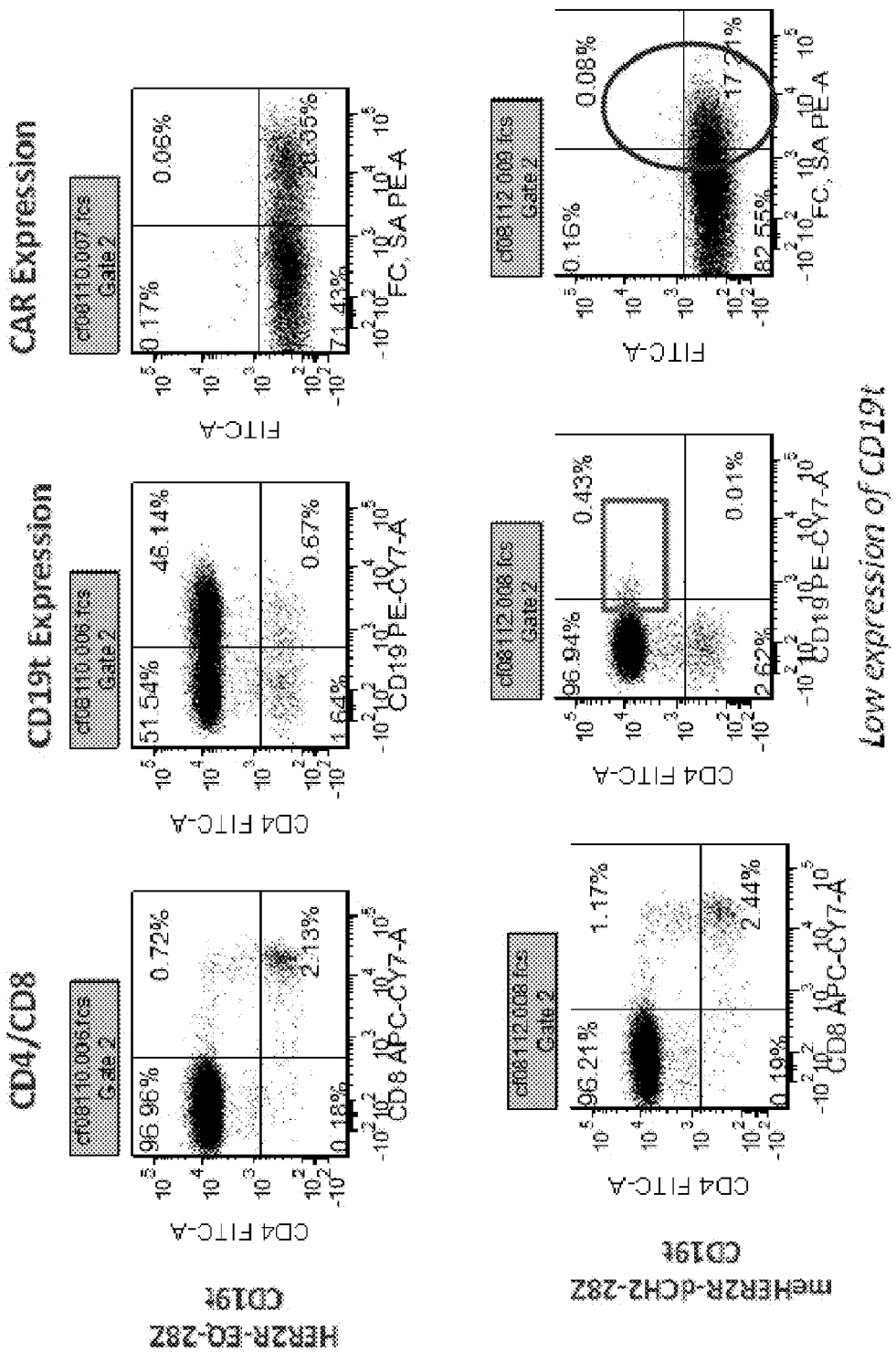
FIG. 6. meHER2R-CAR T cells. Primary human T cells were lentivirally transduced to express either the HER2-scFv-CAR (HER2R-EQ-28Z) or the meditope enabled HER2-CAR (meHER2R-dCH2-28Z). Cell surface expression of the meHER2-dCH2-28Z is confirmed by flow cytometry using anti-Fc antibody.
Figure 7:
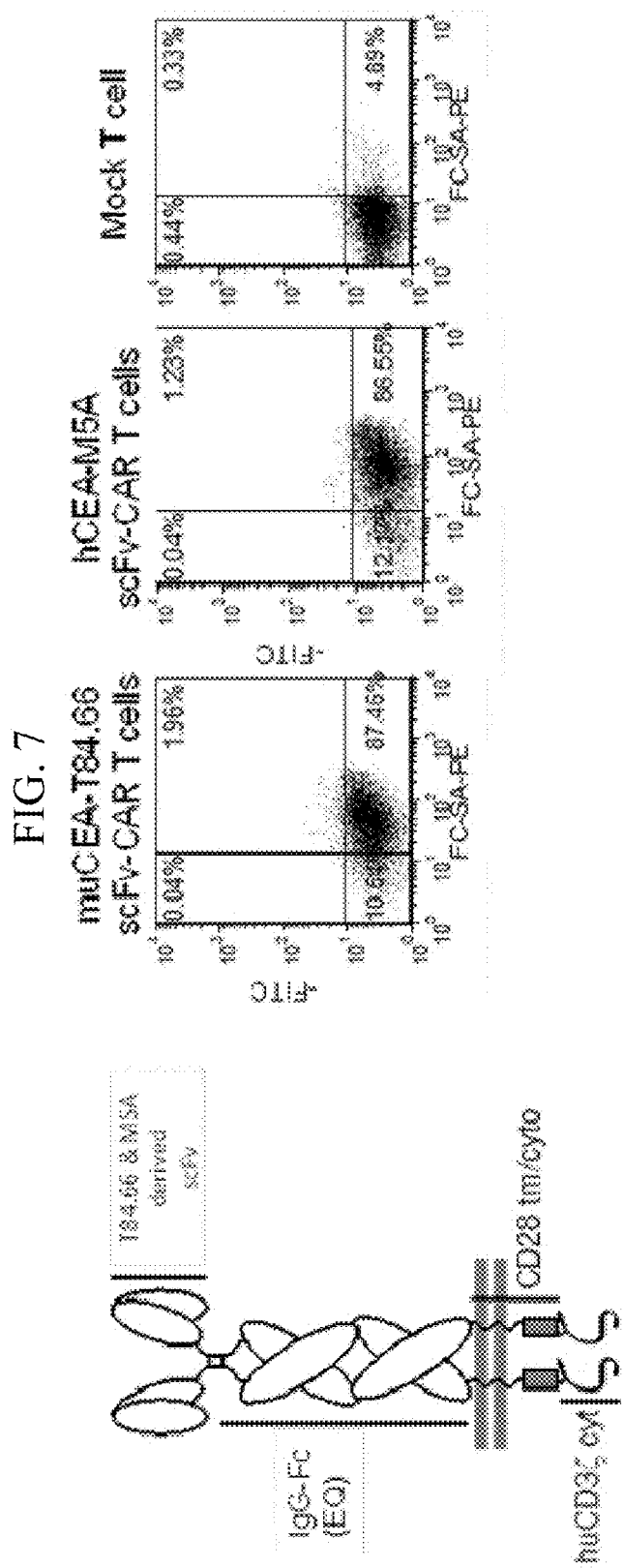
FIG. 7. Expression of murine T84.66 and humanized M5A derived scFv-CEA-specific CARs in Primary Human T cells. Both muT84.66 and M5A derived CEA-scFv-CARs are stably expressed by engineered cells.
Figure 8A:
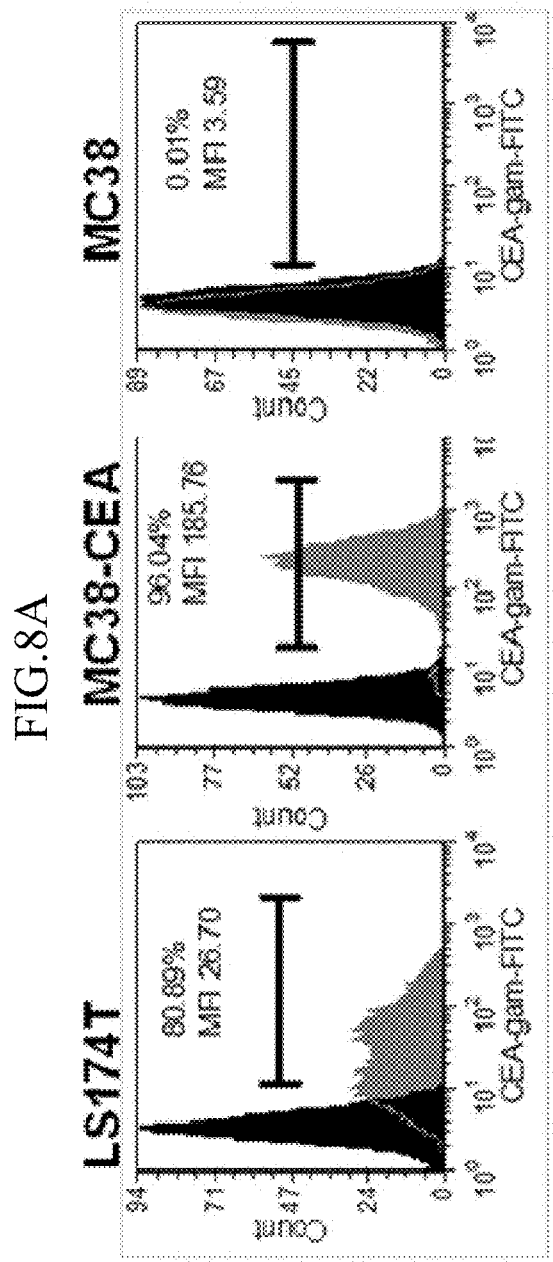
FIG. 8A-8B. Comparing murine T84.66 versus humanized M5A scFv-CEA-specific CART cells for killing of CEA+ targets.
Figure 8B:
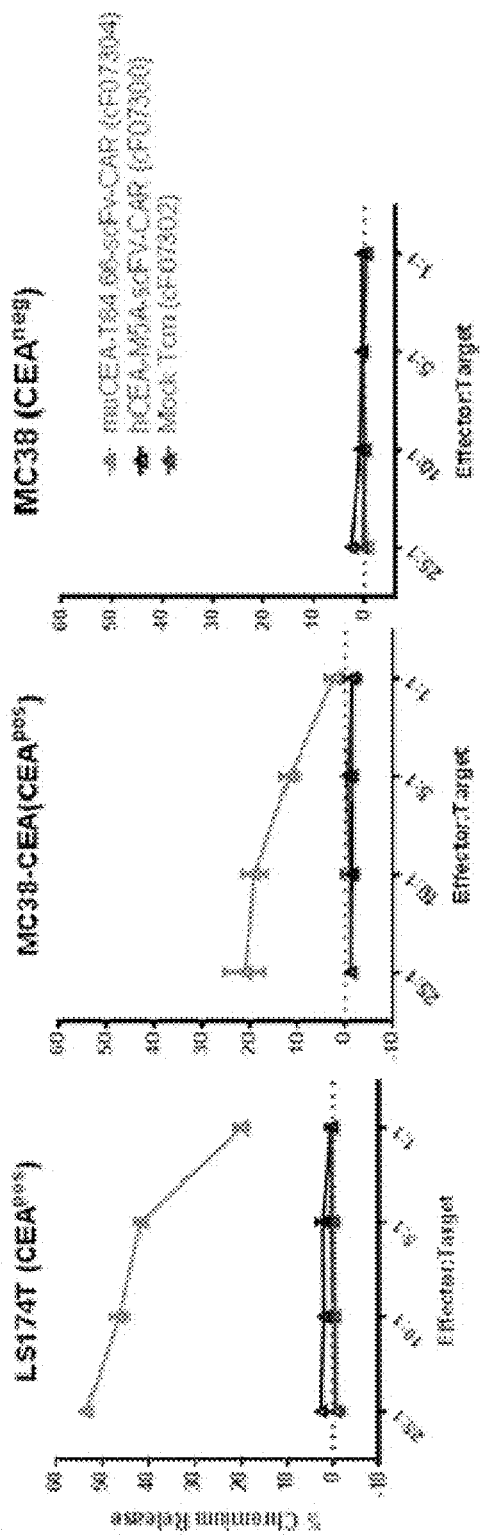
Figure 9:
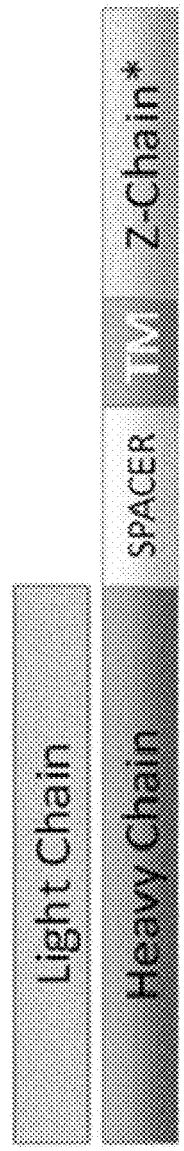
FIG. 9. Illustration of exemplary Fab and linker configuration.
Figure 10:
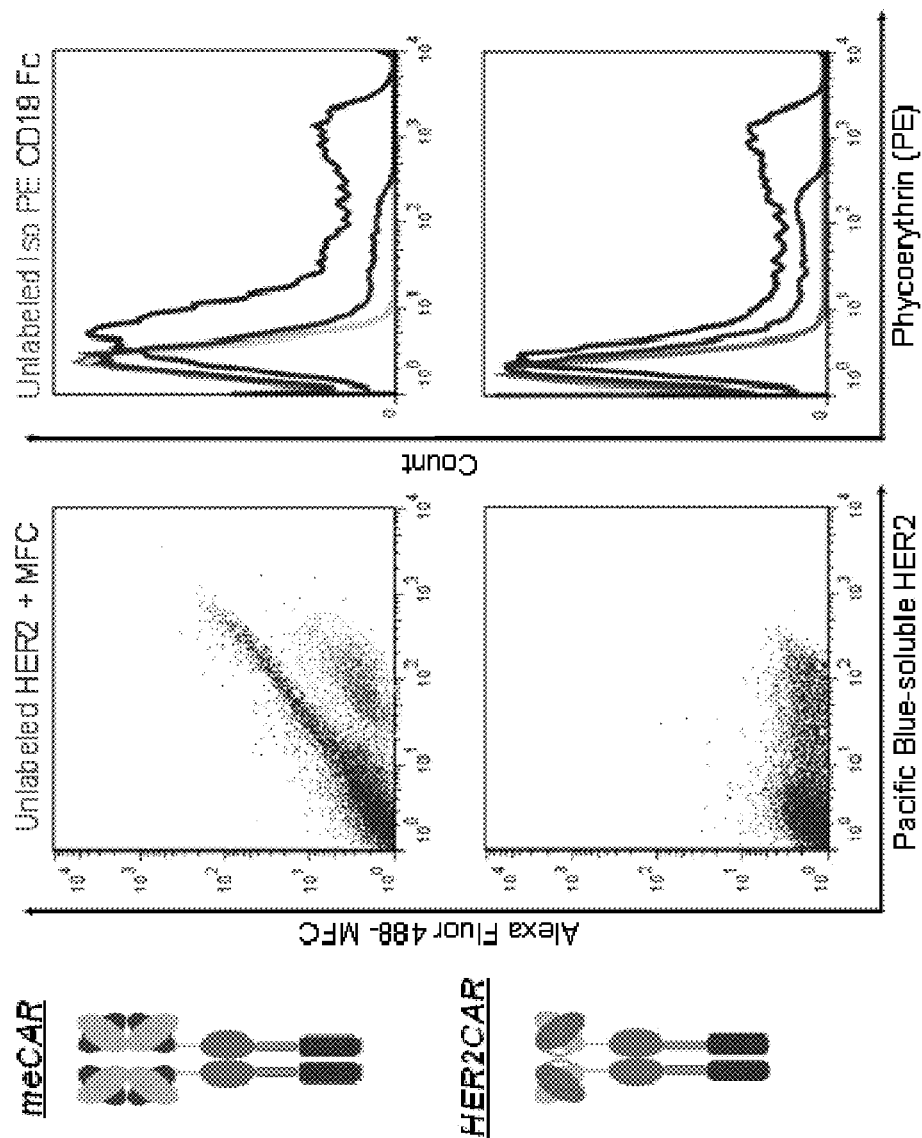
FIG. 10. CHO-S cells were transfected with either memAb trastuzumab Fab CAR (meCAR) or trastuzumab scFv-CAR (HER2CAR) plasmid for two days. The meCAR and HER2CAR construct differ only in the HER2-targeting component, each linked to CH3, CD28 transmembrane domain and CD3 zeta. A truncated CD19 can also be expressed from the plasmids and serves as a transfection control. The transfected CHO-S cells were filtered with 40 µm filter to remove debris and were washed once with 0.3% BSA-PBS. The cells were then labeled on ice for 1 h with: PE-anti-CD19 or isotype control, biotinylated anti-Fcγ followed by streptavidin-PE, or double-labeled with Pacific Blue-soluble HER2 and Alexa Fluor 488-meditope Fc (MFC). At the end of the incubations, the cells were washed once and resuspended in 800 µl of wash buffer. Sytox blue was added to the unlabeled cells for viability and membrane permeability assessments. Cells were gated with forward and side scatter only. Sytox Blue and Pacific Blue have considerable overlap in their spectra, thus the Sytox Blue signal of the unlabeled samples have "leaked" into the Pacific Blue channel. It has been noted that when CHO-S cells express membrane-bound proteins, their membrane becomes more permeable to Sytox Blue dye as shown with the group of cells in yellow oval. Both meCAR- and HER2CAR-transfected cells are CD19, CH3 and sHER2 positive, but only the meCAR is also positive for MFC binding.
Figure 11A:
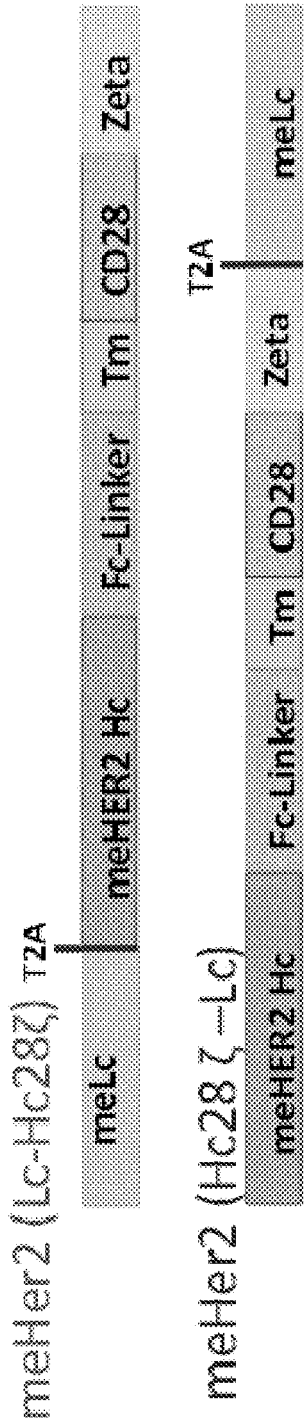
FIG. 11A-11C. Expression of meditope-enabled Fab-CARs in primary human T cells.
Figure 11B:
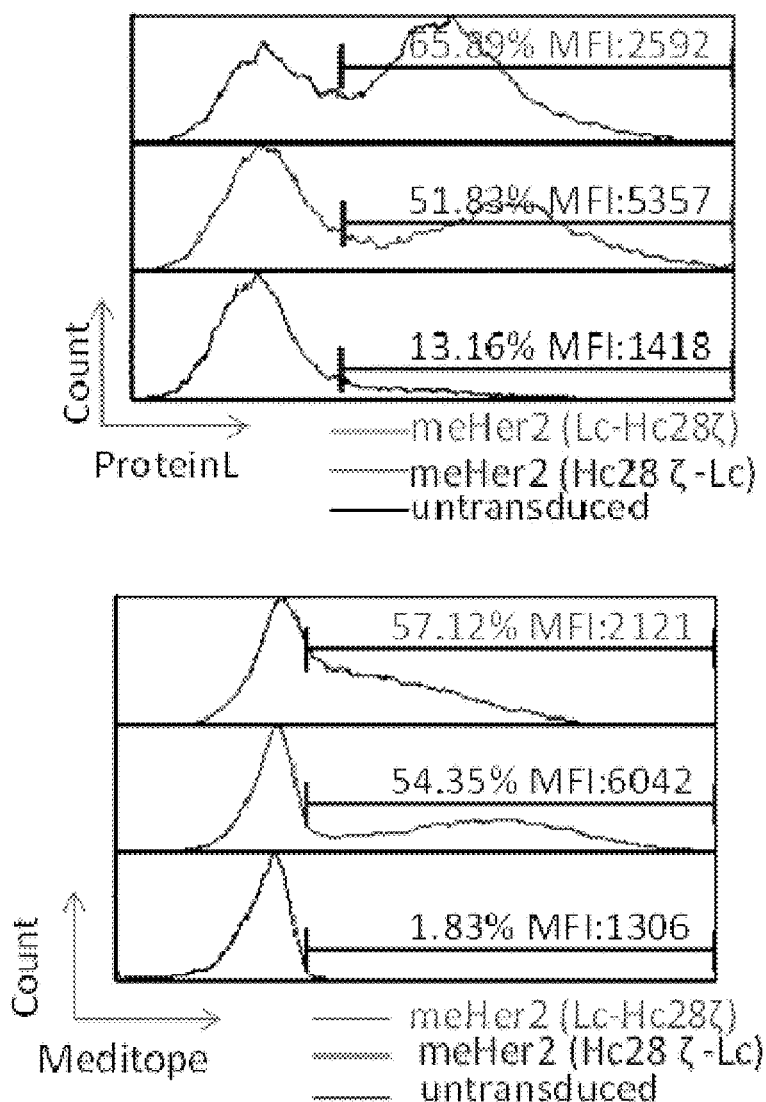
Figure 11C:
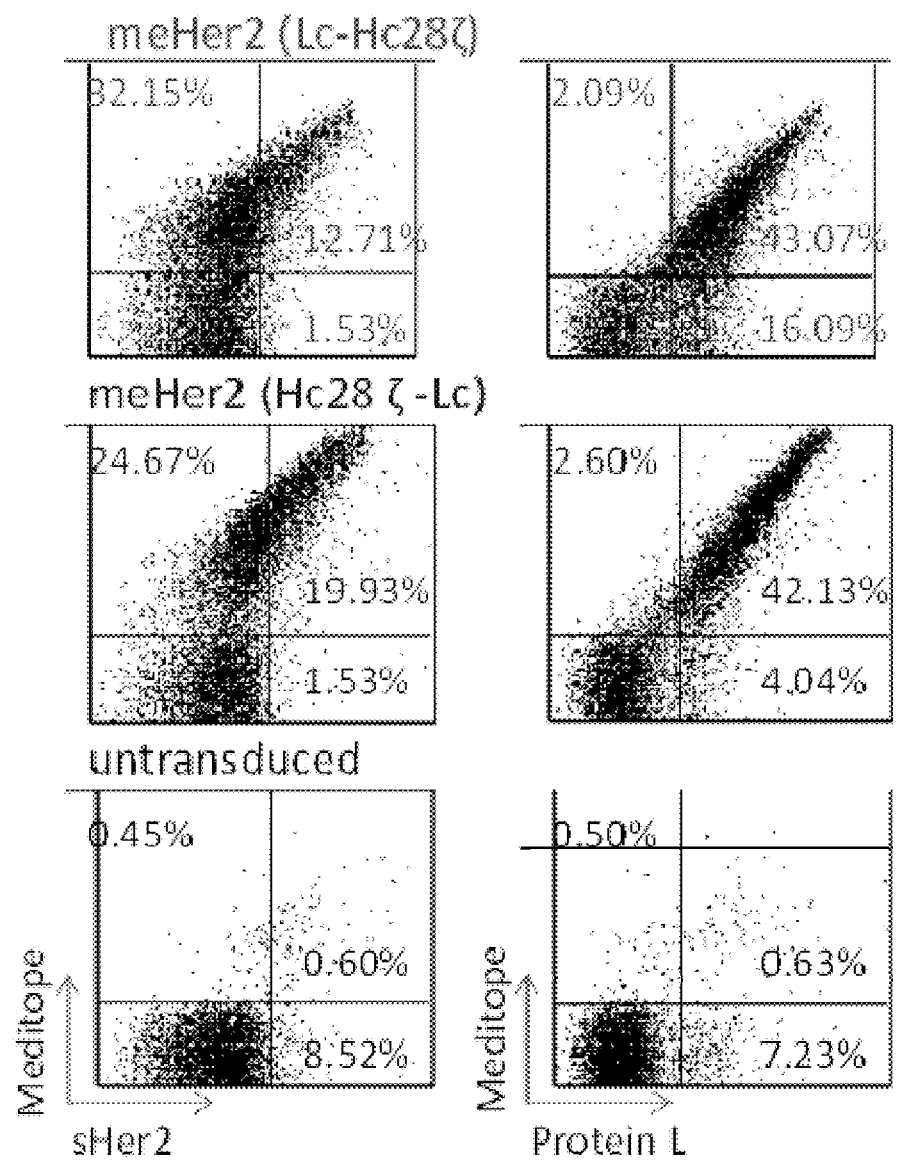
Figure 12A:
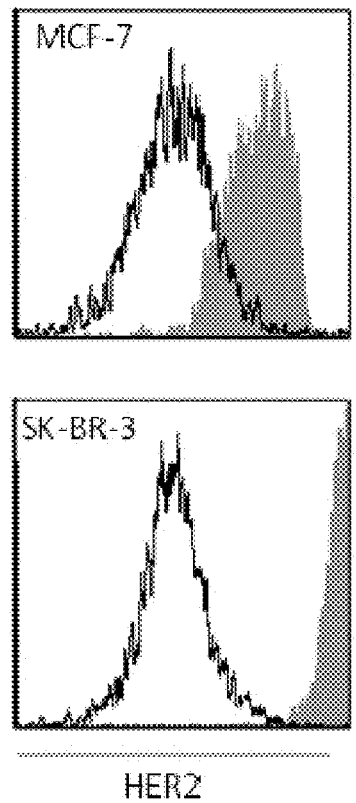
Figure 12B:
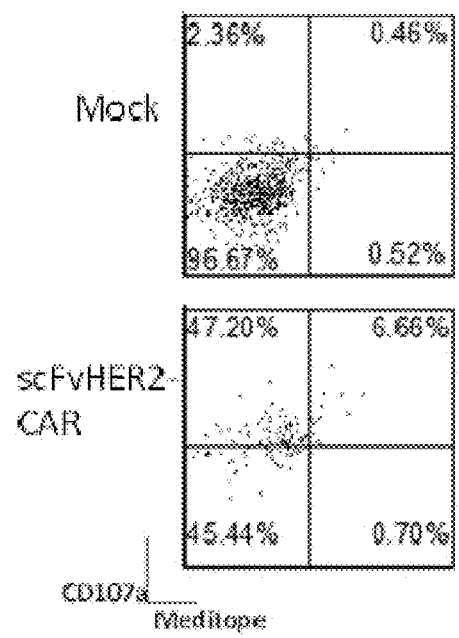
Figure 12D:
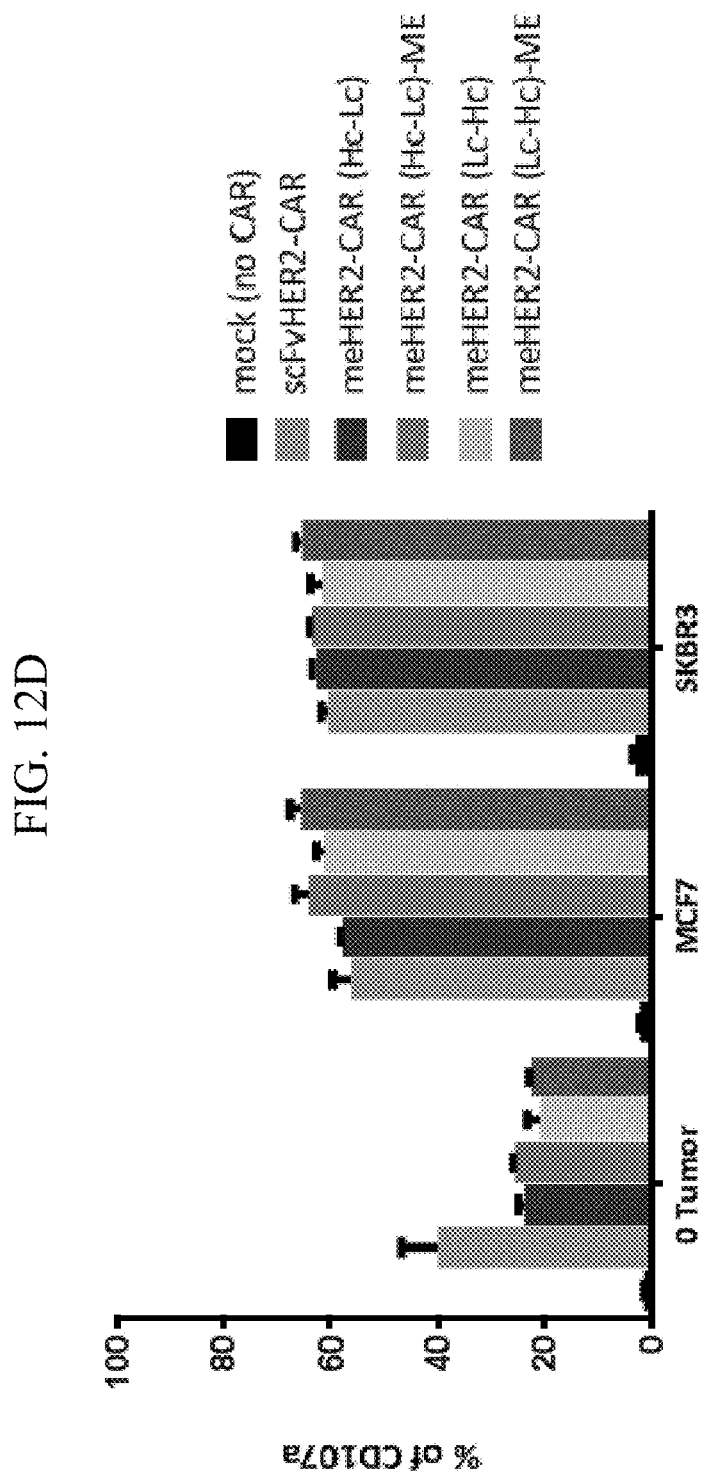
Figure 13A:
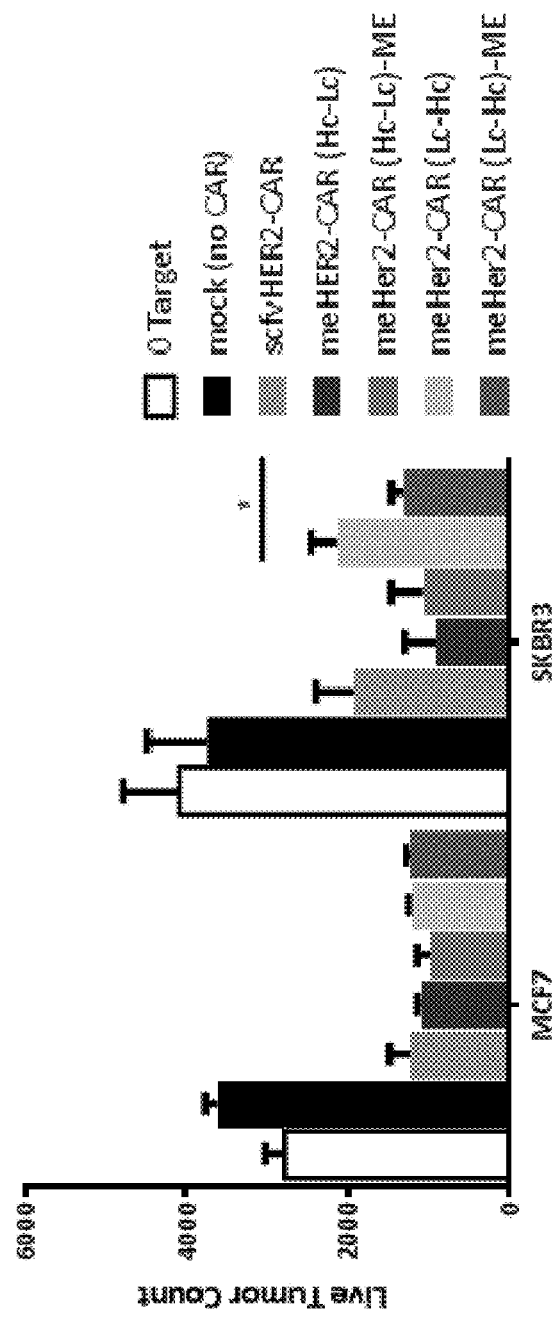
FIG. 13A-13B. Meditope-enabled HER2-CARs (meHER2) and scFvHER2 CAR-engineered T cells kill HER2+ targets at comparable efficiency and meditope peptide does not negatively impact T cell killing. Long term killing assay to compare killing potency of meHER2 and scFvHER2-CAR T cells. HD187.2 T cells were engineered to express either meHER2(Hc-Lc):28ζ CAR, meHER2(Lc-Hc):28ζ CAR, scFvHER2:28ζ CAR or no CAR (mock). Versions of the meHER2:28ζ-CAR differ only in the orientation of the heavy chain (Hc) and light chain (Lc), see FIG. 11. HER2-CAR T cells lines, or mock control were co-cultured with HER2$^+$ breast cancer lines, MCF-7 and SKBR3, for 48-hours at a 1:4 effector to target ratio (based on CAR expression). Killing was assessed by quantifying the number of live tumor cells remaining after co-incubation. A viability stain, DAPI (Molecular Probes™; Cat# D21490) and a human leukocyte antigen, CD45 (BD Biosciences; Cat#347464), were used to exclude the dead cells and T cells from the live tumor count. meCAR-T cells were incubated with and without meditope-AF647 (200 nM) prior to co-culture to evaluate the impact of meditope peptide on meHER2 redirected killing potential, FIG. 13A, Bar graph depicts the average live tumor count (DAPI-CD45-) of three replicate wells per combination.
Figure 13B:
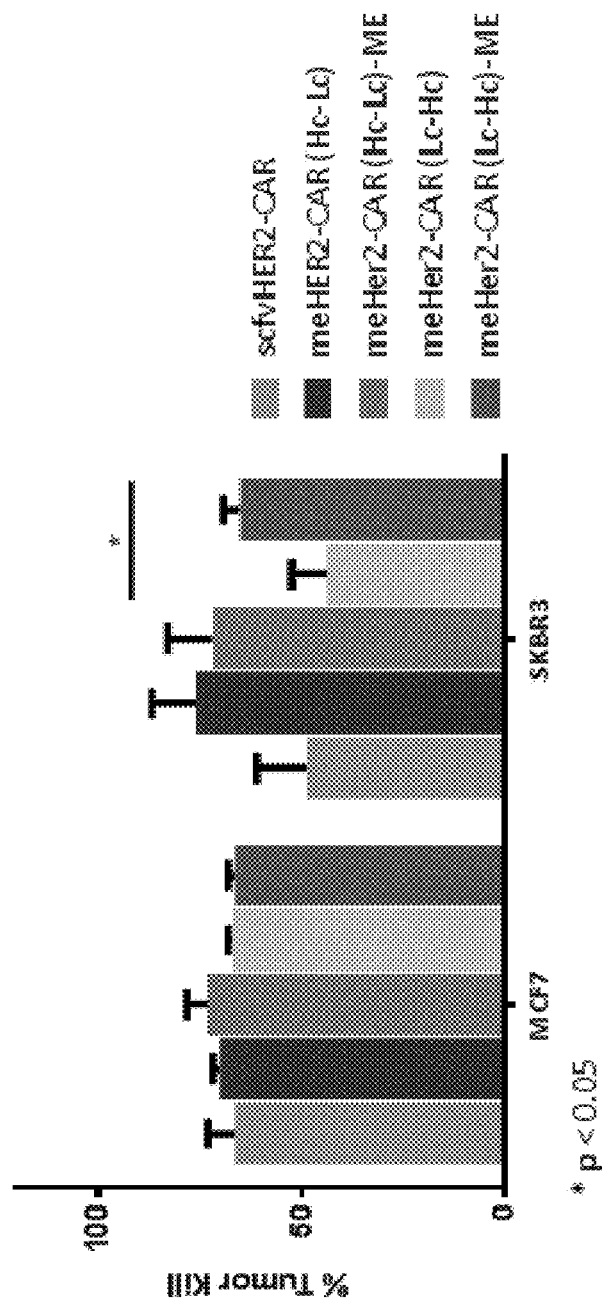

Pre-targeted imaging separates the slow accumulation of mAbs at the tumor and slow clearance of mAbs from the blood from the relatively short half-life of useful PET metals through a two-step process. First, the patient is administered a conjugated mAb (streptavidin or with a unique binding domain) and then a homing ligand carrying $^{64}$Cu. The homing ligand rapidly binds to the tumor associated, modified mAb or is rapidly excreted. Since the $^{64}$Cu undergoes less half-lives, the signal is higher. Also, since the tracer is rapidly cleared, the background is reduced. Pre-clinical images using this approach have produced significantly better images than direct conjugation methods (10). Imaging CAR T cell location, expansion and longevity in patients will be tremendously useful in the development and clinical evaluation of this therapy. In vivo CAR T cell mouse models for the treatment of solid tumors, including brain tumors (FIG. 6), are well established in our lab (27, 34).

A dual orthotropic and metastatic tumor xenograft model will be employed using female NOD-scid IL2Rγnull (NSG) mice and the HER2-amplified breast cancer line BT474 that has been engineered to express both firefly luciferase (ffLuc) for non-invasive Xenogen imaging and a fluorescent reporter EGFP (27). EGFP-ffLuc+ BT474 tumor cells will be implanted concurrently into the mammary fat pad (1×10$^6$ in a 50 μL mixture of PBS and Matrigel) to model primary disease, and intracranially (1×10$^5$ in 2 μL PBS) to model metastatic disease. Once tumors are established (typically 7-14 days), a single dose of 5×10$^6$ each HER2-meCAR Tcm or un-engineered Tcm (mock) or PBS will be infused intravenously. It has been shown that i.v. administered CAR T cell do traffic to the brain and mediate tumor regression (35, 36). Tumor growth/regression will be non-invasively quantified by Xenogen® IVIS optical imaging and caliper measurement, and survival analyzed by Kaplan-Meier. For these studies, T cell infiltration and persistence in tumors will be evaluated by immunohistochemistry using an Alexa Fluor-labeled meditope and CD3 markers, and Tcm persistence will be quantified by flow cytometry using Alexa Fluor-labeled meditopes, CD45, CD4/CD8, and CD62L markers in tumors and lymphoid tissue. Proliferation/apoptosis in tumors (Ki67, TUNEL), CAR T-cell activation and cytolytic function (CD69, Granzyme B, IFNγ) in tumors and in lymphoid tissues will be measured by flow cytometry. In vivo efficacy of meCAR T cells will be compared to previously characterized HER2-28ζ scFv CAR T cells. These studies will establish the capacity of meCAR T cells to mediate HER2+ tumor regression, and reveal potential differences in anti-tumor activity and T cell persistence between the meFab or memAb CAR T cells.

The high-affinity meditope with a C-terminal DOTA will be directly synthesized. The DOTA-meditope will be charged with $^{64}$Cu, purified by gel chromatography and mixed with the meCAR T cells. The cells will be administered to animals bearing EGFP-ffLuc+ BT474 tumors. MicroPET imaging will be conducted immediately following the injection and at defined time points thereafter. At day 1 and day 2, animals will be sacrificed and the bio distribution of the meditope and meCAR T cells will be determined for meCAR T cells at primary and metastatic disease sites. Next, pre-targeted imaging methods will be applied. The meCAR T cells will be administered in the same orthotopic and metastatic xenograft model. $^{64}$CU-DOTA meditope will be administered at 1 h post meCAR T cell administration and imaged at defined points thereafter (1, 2, 3 and 6 hours). The same imaging schedule will be conducted 1 day, 3 days and 10 days post meCAR T cell administration. Again, animals will be sacrificed and the bio distribution(s) will be determined through radiography.

Tables

TABLE 1

Examples of transmembrane domains.

| Protein | NCBI Accession No. | Length | Transmembrane Domain Sequence |
|---|---|---|---|
| CD3z | GI:623041 | 21aa | LCYLLDGILFIYGVILTALFL (SEQ ID NO: 1) |
| CD28 | GI:340545506 | 27aa | FWVLVVVGGVLACYSLLVTVAFI IFWV (SEQ ID NO: 2) |
| CD4 | GI:179143 | 22aa | MALIVLGGVAGLLLFIGLGIFF (SEQ ID NO: 3) |
| CD8 | GI:225007534 | 21aa | IYIWAPLAGTCGVLLLSLVIT (SEQ ID NO: 4) |
| CD8 | GI:225007534 | 23aa | IYIWAPLAGTCGVLLLSLVITLY (SEQ ID NO: 5) |
| CD8 | GI:225007534 | 24aa | IYIWAPLAGTCGVLLLSLVITLY C (SEQ ID NO: 6) |
| 41BB | GI:315259099 | 27aa | IISFFLALTSTALLFLLFFLTLR FSVV (SEQ ID NO: 7) |
| OX40 | GI:315360637 | 21aa | VAAILGLGLVLGLLGPLAILL (SEQ ID NO: 8) |
| ICOS | GI:251823951 | 21aa | FWLPIGCAAFVVVCILGCILI (SEQ ID NO: 9) |
| CD62L | GI:262206314 | 23aa | PLFIPVAVMVTAFSGLAFIIWLA (SEQ ID NO: 10) |

TABLE 2

Examples of signaling domains.

| Protein | NCBI Accession No. | Length | Endo Signaling |
|---|---|---|---|
| CD3ζ | GI:623041 | 113 aa | SEQ ID NO: 11 RVKFSRSADAPAYQQGQNQLYNELNLGRREEYDVL DKRRGRDPEMGGKPQRRKNPQEGLY: |

TABLE 2-continued

Examples of signaling domains.

| Protein | NCBI Accession No. | Length | Endo Signaling |
|---|---|---|---|
| CD28 | GI:34054550 6 | 42aa | SEQ ID NO: 12<br>RSKRSRLLHSDYMNMTPRRPGPTRKHYQPYAPPRD<br>FAAYRS: |
| CD28gg* | GI:34054550 6 | 42aa | SEQ ID NO: 13<br>RSKRSRGGHSDYMNMTPRRPGPTRKHYQPYAPPRD<br>FAAYRS (ref): |
| 41BB | GI:31525909 9 | 42 aa | SEQ ID NO: 14<br>KRGRKKLLYIFKQPFMRPVQTTQEEDGCSCRFPEE<br>EEGGCEL: |
| OX40 | GI:31536063 7 | 42 aa | SEQ ID NO: 15<br>ALYLLRRDQRLPPDAHKPPGGGSFRTPIQEEQADA<br>HSTLAKI: |
| ICOS | GI:25182395 1 | 38 aa | SEQ ID NO: 16<br>CWLTKKKYSSSVHDPNGEYMFMRAVNTAKKSRLT<br>DVTL: |

REFERENCES

1. Donaldson J M, Zer C, Avery K N, Bzymek K P, Horne D A, Williams J C. Identification and grafting of a unique peptide-binding site in the Fab framework of monoclonal antibodies. Proc Natl Acad Sci USA. 2013; 110(43): 17456-61. Epub 2013/10/09. doi: 10.1073/pnas.1307309110. PubMed PMID: 24101516 PMCID: PMC3808661.
2. Kochenderfer J N, Dudley M E, Feldman S A, Wilson W H, Spaner D E, Maric I, Stetler-Stevenson M, Phan G Q, Hughes M S, Sherry R M, Yang J C, Kammula U S, Devillier L, Carpenter R, Nathan D A, Morgan R A, Laurencot C, Rosenberg S A. B-cell depletion and remissions of malignancy along with cytokine-associated toxicity in a clinical trial of anti-CD19 chimeric-antigen-receptor-transduced T cells. Blood. 2012; 119(12):2709-20. Epub 2011/12/14. doi: 10.1182/blood-2011-10-384388. PubMed PMID: 22160384 PMCID: PMC3327450.
3. Davila M L, Riviere I, Wang X, Bartido S, Park J, Curran K, Chung S S, Stefanski J, Borquez-Ojeda O, Olszewska M, Qu J, Wasielewska T, He Q, Fink M, Shinglot H, Youssif M, Satter M, Wang Y, Hosey J, Quintanilla H, Halton E, Bernal Y, Bouhassira D C, Arcila M E, Gonen M, Roboz G J, Maslak P, Douer D, Frattini M G, Giralt S, Sadelain M, Brentjens R. Efficacy and toxicity management of 19-28z CAR T cell therapy in B cell acute lymphoblastic leukemia. Science translational medicine. 2014; 6(224):224ra25. Epub 2014/02/21. doi: 10.1126/scitranslmed.3008226. PubMed PMID: 24553386.
4. Grupp S A, Kalos M, Barrett D, Aplenc R, Porter D L, Rheingold S R, Teachey D T, Chew A, Hauck B, Wright J F, Milone M C, Levine B L, June C H. Chimeric antigen receptor-modified T cells for acute lymphoid leukemia. N Engl J Med. 2013; 368(16):1509-18. Epub 2013/03/27. doi: 10.1056/NEJMoa1215134. PubMed PMID: 23527958.
5. Kalos M, June C H. Adoptive T cell transfer for cancer immunotherapy in the era of synthetic biology. Immunity. 2013; 39(1):49-60. Epub 2013/07/31. doi: 10.1016/j.immuni.2013.07.002. PubMed PMID: 23890063 PMCID: PMC3809038.
6. Mardiros A, Dos Santos C, McDonald T, Brown C E, Wang X, Budde L E, Hoffman L, Aguilar B, Chang W C, Bretzlaff W, Chang B, Jonnalagadda M, Starr R, Ostberg J R, Jensen M C, Bhatia R, Forman S J. T cells expressing CD123-specific chimeric antigen receptors exhibit specific cytolytic effector functions and antitumor effects against human acute myeloid leukemia. Blood. 2013; 122(18):3138-48. Epub 2013/09/14. doi: 10.1182/blood-2012-12-474056. PubMed PMID: 24030378 PMCID: PMC3814731.
7. Turtle C J, Hudecek M, Jensen M C, Riddell S R. Engineered T cells for anti-cancer therapy. Curr Opin Immunol. 2012; 24(5):633-9. Epub 2012/07/24. doi: 10.1016/j.coi.2012.06.004. PubMed PMID: 22818942 PMCID: PMC3622551.
8. NCI. CAR T-Cell Therapy: Engineering Patients' Immune Cells to Treat Their Cancers 2013. Available from: http://www.cancer.gov/cancertopics/research-updates/2013/CAR-T-Cells.
9. Sharkey R M, Chang C H, Rossi E A, McBride W J, Goldenberg D M. Pretargeting: taking an alternate route for localizing radionuclides. Tumour Biol. 2012; 33(3): 591-600. Epub 2012/03/08. doi: 10.1007/s13277-012-0367-6. PubMed PMID: 22396041.
10. Goldenberg D M, Chang C H, Rossi E A, J W, McBride, Sharkey R M. Pretargeted molecular imaging and radioimmunotherapy. Theranostics. 2012; 2(5):523-40. Epub 2012/06/28. doi: 10.7150/thno.3582. PubMed PMID: 22737190 PMCID: PMC3364558.
11. Rossi E A, Goldenberg D M, Cardillo T M, McBride W J, Sharkey R M, Chang C H. Stably tethered multifunctional structures of defined composition made by the dock and lock method for use in cancer targeting. Proc Natl Acad Sci USA. 2006; 103(18):6841-6. Epub 2006/04/26. doi: 10.1073/pnas.0600982103. PubMed PMID: 16636283 PMCID: PMC1447525.

12. McConnell A D, Spasojevich V, Macomber J L, Krapf I P, Chen A, Sheffer J C, Berkebile A, Horlick R A, Neben S, King D J, Bowers P M. An integrated approach to extreme thermostabilization and affinity maturation of an antibody. Protein Eng Des Sel. 2013; 26(2):151-64. Epub 2012/11/23. doi: 10.1093/protein/gzs090. PubMed PMID: 23173178.

13. Honegger A. Engineering antibodies for stability and efficient folding. Handbook of experimental pharmacology. 2008(181):47-68. Epub 2007/12/12. doi: 10.1007/978-3-540-73259-4_3. PubMed PMID: 18071941.

14. Donaldson J M, Kari C, Fragoso R C, Rodeck U, Williams J C. Design and development of masked therapeutic antibodies to limit off-target effects: Application to anti-EGFR antibodies. Cancer Biol Ther. 2009; 8(22). PubMed PMID: 19783899.

15. Szymczak A L, Workman C J, Wang Y, Vignali K M, Dilioglou S, Vanin E F, Vignali D A. Correction of multi-gene deficiency in vivo using a single 'self-cleaving' 2A peptide-based retroviral vector. Nat Biotechnol. 2004; 22(5):589-94. Epub 2004/04/06. doi: 10.1038/nbt957. PubMed PMID: 15064769.

16. Kute T, Lack C M, Willingham M, Bishwokama B, Williams H, Barrett K, Mitchell T, Vaughn J P. Development of Herceptin resistance in breast cancer cells. Cytometry Part A: the journal of the International Society for Analytical Cytology. 2004; 57(2):86-93. Epub 2004/01/30. doi: 10.1002/cyto.a.10095. PubMed PMID: 14750129.

17. Morgan R A, Yang J C, Kitano M, Dudley M E, Laurencot C M, Rosenberg S A. Case report of a serious adverse event following the administration of T cells transduced with a chimeric antigen receptor recognizing ERBB2. Molecular therapy: the journal of the American Society of Gene Therapy. 2010; 18(4):843-51. Epub 2010/02/25. doi: 10.1038/mt.2010.24. PubMed PMID: 20179677 PMCID: PMC2862534.

18. Wang X, Naranjo A, Brown C E, Bautista C, Wong C W, Chang W C, Aguilar B, Ostberg J R, Riddell S R, Forman S J, Jensen M C. Phenotypic and functional attributes of lentivirus-modified CD19-specific human CD8+ central memory T cells manufactured at clinical scale. J Immunother. 2012; 35(9):689-701. Epub 2012/10/24. doi: 10.1097/CJI.0b013e318270dec7. PubMed PMID: 23090078 PMCID: PMC3525345.

19. Rosenberg S A, Yang J C, Sherry R M, Kammula U S, Hughes M S, Phan G Q, Citrin D E, Restifo N P, Robbins P F, Wunderlich J R, Morton K E, Laurencot C M, Steinberg S M, White D E, Dudley M E. Durable complete responses in heavily pretreated patients with metastatic melanoma using T-cell transfer immunotherapy. Clin Cancer Res. 2011; 17(13):4550-7. PubMed PMID: 21498393.

20. Kalos M, Levine B L, Porter D L, Katz S, Grupp S A, Bagg A, June C H. T cells with chimeric antigen receptors have potent antitumor effects and can establish memory in patients with advanced leukemia. Sci Transl Med. 2011; 3(95):95ra73. Epub 2011/08/13. doi: 3/95/95ra73 [pii]

21. Wang X, Berger C, Wong C W, Forman S J, Riddell S R, Jensen M C. Engraftment of human central memory-derived effector CD8+ T cells in immunodeficient mice. Blood. 2011; 117(6):1888-98. Epub 2010/12/03. doi: blood-2010-10-310599 [pii]

22. Berger C, Jensen M C, Lansdorp P M, Gough M, Elliott C, Riddell S R. Adoptive transfer of effector CD8 T cells derived from central memory cells establishes persistent T cell memory in primates. J Clin Invest. 2008; 118(1):294-305. PubMed PMID: 18060041.

23. Klebanoff C A, Gattinoni L, Restifo N P. Sorting through subsets: which T-cell populations mediate highly effective adoptive immunotherapy? J Immunother. 2012; 35(9): 651-60. Epub 2012/10/24. doi: 10.1097/CJI.0b013e31827806e6. PubMed PMID: 23090074 PMCID: PMCPMC3501135.

24. Gattinoni L, Klebanoff C A, Palmer D C, Wrzesinski C, Kerstann K, Yu Z, Finkelstein S E, Theoret M R, Rosenberg S A, Restifo N P. Acquisition of full effector function in vitro paradoxically impairs the in vivo antitumor efficacy of adoptively transferred CD8+ T cells. J Clin Invest. 2005; 115(6):1616-26. doi: 10.1172/JCI24480. PubMed PMID: 15931392 PMCID: PMC1137001.

25. Kaech S M, Wherry E J. Heterogeneity and cell-fate decisions in effector and memory CD8+ T cell differentiation during viral infection. Immunity. 2007; 27(3):393-405. doi: 10.1016/j.immuni.2007.08.007. PubMed PMID: 17892848 PMCID: PMC3431921.

26. Srinivasan S, Deng W, Li R. L-selectin transmembrane and cytoplasmic domains are monomeric in membranes. Biochim Biophys Acta. 2011; 1808(6):1709-15. Epub 2011/02/15. doi: 10.1016/j.bbamem.2011.02.006. PubMed PMID: 21316337 PMCID: PMC3078985.

27. Brown C E, Starr R, Aguilar B, Shami A F, Martinez C, D'Apuzzo M, Barish M E, Forman S J, Jensen M C. Stem-like tumor-initiating cells isolated from IL13Ralpha2 expressing gliomas are targeted and killed by IL13-zetakine-redirected T Cells. Clin Cancer Res. 2012; 18(8):2199-209. Epub 2012/03/13. doi: 10.1158/1078-0432.CCR-11-1669. PubMed PMID: 22407828 PMCID: PMC3578382.

28. Sengupta P, Jovanovic-Talisman T, Skoko D, Renz M, Veatch S L, Lippincott-Schwartz J. Probing protein heterogeneity in the plasma membrane using PALM and pair correlation analysis. Nat Methods. 2011; 8(11):969-75. Epub 2011/09/20. doi: 10.1038/nmeth.1704. PubMed PMID: 21926998 PMCID: PMC3400087.

29. Hudecek M, Lupo-Stanghellini M T, Kosasih P L, Sommermeyer D, Jensen M C, Rader C, Riddell S R. Receptor affinity and extracellular domain modifications affect tumor recognition by ROR1-specific chimeric antigen receptor T cells. Clin Cancer Res. 2013; 19(12):3153-64. Epub 2013/04/27. doi: 10.1158/1078-0432.CCR-13-0330. PubMed PMID: 23620405 PMCID: PMC3804130.

30. Wilkie S, Picco G, Foster J, Davies D M, Julien S, Cooper L, Arif S, Mather S J, Taylor-Papadimitriou J, Burchell J M, Maher J. Retargeting of human T cells to tumor-associated MUC1: the evolution of a chimeric antigen receptor. J Immunol. 2008; 180(7):4901-9. Epub 2008/03/21. PubMed PMID: 18354214.

31. Guest R D, Hawkins R E, Kirillova N, Cheadle E J, Arnold J, O'Neill A, Irlam J, Chester K A, Kemshead J T, Shaw D M, Embleton M J, Stern P L, Gilham D E. The role of extracellular spacer regions in the optimal design of chimeric immune receptors: evaluation of four different scFvs and antigens. J Immunother. 2005; 28(3):203-11. Epub 2005/04/20. PubMed PMID: 15838376.

32. Schlatter S, Stansfield S H, Dinnis D M, Racher A J, Birch J R, James D C. On the optimal ratio of heavy to light chain genes for efficient recombinant antibody production by CHO cells. Biotechnology progress. 2005;

33. Akamatsu Y, Pakabunto K, Xu Z, Zhang Y, Tsurushita N. Whole IgG surface display on mammalian cells: Application to isolation of neutralizing chicken monoclonal anti-IL-12 antibodies. J Immunol Methods. 2007; 327(1-2):40-52. Epub 2007/08/28. doi: 10.1016/j.jim.2007.07.007. PubMed PMID: 17719061.
34. Brown C E, Starr R, Martinez C, Aguilar B, D'Apuzzo M, Todorov I, Shih C C, Badie B, Hudecek M, Riddell S R, Jensen M C. Recognition and killing of brain tumor stem-like initiating cells by CD8+ cytolytic T cells. Cancer Res. 2009; 69(23):8886-93. Epub 2009/11/12. doi: 10.1158/0008-5472.CAN-09-2687. PubMed PMID: 19903840 PMCID: PMC2789196.
35. Brown C E, Vishwanath R P, Aguilar B, Starr R, Najbauer J, Aboody K S, Jensen M C. Tumor-derived chemokine MCP-1/CCL2 is sufficient for mediating tumor tropism of adoptively transferred T cells. J Immunol. 2007; 179(5):3332-41. Epub 2007/08/22. PubMed PMID: 17709550.
36. Miao H, Choi B D, Suryadevara C M, Sanchez-Perez L, Yang S, De Leon G, Sayour E J, McLendon R, Herndon J E, 2nd, Healy P, Archer G E, Bigner D D, Johnson L A, Sampson J H. EGFRvIII-Specific Chimeric Antigen Receptor T Cells Migrate to and Kill Tumor Deposits Infiltrating the Brain Parenchyma in an Invasive Xenograft Model of Glioblastoma. PLoS One. 2014; 9(4): e94281. Epub 2014/04/12. doi: 10.1371/journal.pone.0094281. PubMed PMID: 24722266 PMCID: PMC3983153.
37. Avery et al. 2015 (Scientific Reports 5:7817) Kendra N. Avery, Cindy Zer, Krzysztof P. Bzymek & John C. Williams. Development of a High Affinity, Non-covalent Biologic to Add Functionality to Fabs. Scientific Reports 5, Article Number: 7817 doi:10.1038/srep07817. Published 15 Jan. 2015.

Informal Sequence Listing

| Sequence | SEQ ID NO |
|---|---|
| LCYLLDGILFIYGVILTALFL | SEQ ID NO: 1 |
| FWVLVVVGGVLACYSLLVTVAFIIFWV: | SEQ ID NO: 2 |
| MALIVLGGVAGLLLFIGLGIFF: | SEQ ID NO: 3 |
| IYIWAPLAGTCGVLLLSLVIT: | SEQ ID NO: 4 |
| IYIWAPLAGTCGVLLLSLVITLY: | SEQ ID NO: 5 |
| IYIWAPLAGTCGVLLLSLVITLYC: | SEQ ID NO: 6 |
| IISFFLALTSTALLFLLFF LTLRFSVV: | SEQ ID NO: 7 |
| VAAILGLGLVLGLLGPLAILL: | SEQ ID NO: 8 |
| FWLPIGCAAFVVVCILGCILI: | SEQ ID NO: 9 |
| PLFIPVAVMVTAFSGLAFIIWLA: | SEQ ID NO: 10 |
| RVKFSRSADAPAYQQGQNQLYNELNLGRREEYDVLDKRRGRDPEMGGKPQRRKNPQEGLY: | SEQ ID NO: 11 |
| RSKRSRLLHSDYMNMTPRRPGPTRKHYQPYAPPRDFAAYRS: | SEQ ID NO: 12 |
| RSKRSRGGHSDYMNMTPRRPGPTRKHYQPYAPPRDFAAYRS(ref): | SEQ ID NO: 13 |
| KRGRKKLLYIFKQPFIVIRPVQTTQEEDGCSCRFPEEEEGGCEL: | SEQ ID NO: 14 |
| ALYLLRRDQRLPPDAHKPPGGGSFRTPIQEEQADAHSTLAKI: | SEQ ID NO: 15 |
| CWLTKKKYSSSVHDPNGEYMFMRAVNTAKKSRLTDVTL: | SEQ ID NO: 16 |
| meHer2Fab-IgG4(HL-CH3)-IgG4-CD28tm-CD28gg-Zeta-T2A-meLc: MLLLVTSLLLCELPHPAFLLIPEVQLVESGGGLVQPGGSLRLSCAASGFNIKDTYIHWVR QSPGKGLEWVARIYPTNGYTRYADSVKGRFTISADTSKNTAYLQMNSLRAEDTAIYYCS | SEQ ID NO: 17 |

```
RWGGDGFYAMDYWGQGTLVTVSSASTKGPSVFPLAPSSKSTSGGTAALGCLVKDYFPE

PVTVSWNSGALTSGVHTFPAVLQSSGLYSLSSVVTVPSSSLGTQTYICNVNHKPSNTKVD

KKVEPKSCESKYGPPCPPCPGGGSSGGGSGGQPREPQVYTLPPSQEEMTKNQVSLTCLV

KGFYPSDIAVEWESNGQPENNYKTTPPVLDSDGSFFLYSRLTVDKSRWQEGNVFSCSVM

HEALHNHYTQKSLSLSLGKMFWVLVVVGGVLACYSLLVTVAFIIFWVRSKRSRGGHSD

YMNMTPRRPGPTRKHYQPYAPPRDFAAYRSGGGRVKFSRSADAPAYQQGQNQLYNEL

NLGRREEYDVLDKRRGRDPEMGGKPRRKNPQEGLYNELQKDKMAEAYSEIGMKGERR

RGKGHDGLYQGLSTATKDTYDALHMQALPPRLEGGGEGRGSLLTCGDVEENPGPRML

LLVTSLLLCELPHPAFLLIPDIQMTQSPILLSASVGDRVTITCRASQDVNTAVAWYQQRT

NGSPRLLIYSASFLYSGVPSRFSGSRSGTDFTLTISSLQPEDEADYYCQQHYTTPPTFGAG

TKVEIKRTVAAPSVFIFPPSDEQLKSGTASVVCLLNNFYPREAKVQWKVDNALQSGNSQ

ESVTEQDSKDSTYSLSSTLTLSKADYEKHKVYACEVTHQGLSSPVTKSFNRGEC
```

| | |
|---|---|
| GMCSFRa signal peptide<br>MLLLVTSLLLCELPHPAFLLIP: | SEQ ID NO: 18 |
| Her2Fab (Her2 heavy chain variable and partial constant region)<br>EVQLVESGGGLVQPGGSLRLSCAASGFNIKDTYIHWVRQSPGKGLEWVARIYPTNGYTR<br>YADSVKGRFTISADTSKNTAYLQMNSLRAEDTAWYCSRWGGDGFYAMDYWGQGTLV<br>TVSSASTKGPSVFPLAPSSKSTSGGTAALGCLVKDYFPEPVTVSWNSGALTSGVHTFPAV<br>LQSSGLYSLSSVVTVPSSSLGTQTYICNVNHKPSNTKVDKKVEPKSC: | SEQ ID NO: 19 |
| IgG4(SmP)-Hinge<br>ESKYGPPCPPCP: | SEQ ID NO: 20 |
| Spacer (including IgG4-CH3)<br>GGGSSGGGSGGQPREPQVYTLPPSQEEMTKNQVSLTCLVKGFYPSDIAVEWESNGQPEN<br>NYKTTPPVLDSDGSFFLYSRLTVDKSRWQEGNVFSCSVMHEALHNHYTQKSLSLSLGK: | SEQ ID NO: 21 |
| CD28 transmembrane<br>MFWVLVVVGGVLACYSLLVTVAFIIFWV: | SEQ ID NO: 22 |
| CD28cyto (LLmGG)<br>RSKRSRGGHSDYMNMTPRRPGPTRKHYQPYAPPRDFAAYRS: | SEQ ID NO: 23 |
| Linker ((Gly)3)<br>GGG: | SEQ ID NO: 24 |
| Intracellular T-cell signaling domain (CD3-Zeta)<br>RVKFSRSADAPAYQQGQNQLYNELNLGRREEYDVLDKRRGRDPEMGGKPRRKNPQEG<br>LYNELQKDKMAEAYSEIGMKGERRRGKGHDGLYQGLSTATKDTYDALHMQALPPR: | SEQ ID NO: 25 |
| Self-cleaving peptidyl linker (T2A)<br>LEGGGEGRGSLLTCGDVEENPGPR: | SEQ ID NO: 26 |
| Antibody region (meLc (Her2 Light chain variable and constant region with mutation for meditope))<br>DIQMTQSPILLSASVGDRVTITCRASQDVNTAVAWYQQRTNGSPRLLIYSASFLYSGVPS<br>RFSGSRSGTDFTLTISSLQPEDEADYYCQQHYTTPPTFGAGTKVEIKRTVAAPSVFIFPPSD<br>EQLKSGTASVVCLLNNFYPREAKVQWKVDNALQSGNSQESVTEQDSKDSTYSLSSTLTL<br>SKADYEKHKVYACEVTHQGLSSPVTKSFNRGEC: | SEQ ID NO: 27 |
| meHer2Fab-IgG4(HL-CH3)-IgG4-CD28tm-<br>CD28gg-Zeta-T2A-CD19t-2A-meLc<br>MLLLVTSLLLCELPHPAFLLIPEVQLVESGGGLVQPGGSLRLSCAASGFNIKDTYIHWVR<br>QSPGKGLEWVARIYPTNGYTRYADSVKGRFTISADTSKNTAYLQMNSLRAEDTAIYYCS<br>RWGGDGFYAMDYWGQGTLVTVSSASTKGPSVFPLAPSSKSTSGGTAALGCLVKDYFPE | SEQ ID NO: 28 |

```
PVTVSWNSGALTSGVHTFPAVLQSSGLYSLSSVVTVPSSSLGTQTYICNVNHKPSNTKVD

KKVEPKSCESKYGPPCPPCPGGGSSGGGSGGQPREPQVYTLPPSQEEMTKNQVSLTCLV

KGFYPSDIAVEWESNGQPENNYKTTPPVLDSDGSFFLYSRLTVDKSRWQEGNVFSCSVM

HEALHNHYTQKSLSLSLGKMFWVLVVVGGVLACYSLLVTVAFIIFWVRSKRSRGGHSD

YMNMTPRRPGPTRKHYQPYAPPRDFAAYRSGGGRVKFSRSADAPAYQQGQNQLYNEL

NLGRREEYDVLDKRRGRDPEMGGKPRRKNPQEGLYNELQKDKMAEAYSEIGMKGERR

RGKGHDGLYQGLSTATKDTYDALHMQALPPRLEGGGEGRGSLLTCGDVEENPGPRMPP

PRLLFFLLFLTPMEVRPEEPLVVKVEEGDNAVLQCLKGTSDGPTQQLTWSRESPLKPFLK

LSLGLPGLGIHMRPLAIWLFIFNVSQQMGGFYLCQPGPPSEKAWQPGWTVNVEGSGELF

RWNVSDLGGLGCGLKNRSSEGPSSPSGKLMSPKLYVWAKDRPEIWEGEPPCVPPRDSLN

QSLSQDLTMAPGSTLWLSCGVPPDSVSRGPLSWTHVHPKGPKSLLSLELKDDRPARDM

WVMETGLLLPRATAQDAGKYYCHRGNLTMSFHLEITARPVLWHWLLRTGGWKVSAV

TLAYLIFCLCSLVGILHLQRALVLRRKRGGSTSEGRGSLLTCGDVEENPGPMETDTLLLW

VLLLWVPGSTGDIQMTQSPILLSASVGDRVTITCRASQDVNTAVAWYQQRTNGSPRLLI

YSASFLYSGVPSRFSGSRSGTDFTLTISSLQPEDEADYYCQQHYTTPPTFGAGTKVEIKRT

VAAPSVFIFPPSDEQLKSGTASVVCLLNNFYPREAKVQWKVDNALQSGNSQESVTEQDS

KDSTYSLSSTLTLSKADYEKHKVYACEVTHQGLSSPVTKSFNRGEC:

Marker peptide (CD19t)                                    SEQ ID NO: 29
MPPPRLLFFLLFLTPMEVRPEEPLVVKVEEGDNAVLQCLKGTSDGPTQQLTWSRESPLKP

FLKLSLGLPGLGIHMRPLAIWLFIFNVSQQMGGFYLCQPGPPSEKAWQPGWTVNVEGSG

ELFRWNVSDLGGLGCGLKNRSSEGPSSPSGKLMSPKLYVWAKDRPEIWEGEPPCVPPRD

SLNQSLSQDLTMAPGSTLWLSCGVPPDSVSRGPLSWTHVHPKGPKSLLSLELKDDRPAR

DMWVMETGLLLPRATAQDAGKYYCHRGNLTMSFHLEITARPVLWHWLLRTGGWKVS

AVTLAYLIFCLCSLVGILHLQRALVLRRKR:

Self-cleaving peptidyl linker (2A)                        SEQ ID NO: 30
GGSTSEGRGSLLTCGDVEENPGP:

CAMPATH1 (10E1) MEFAB (183) light chain                   SEQ ID NO: 31
DIQMTQSPILLSASVGDRVTITCKASQNIDKYLNWYQQRTNGSPRLLIYNTNNLQTGVPS

RFSGSGSGTDFTFTISSLQPEDIADYYCLQHISRPRTFGQGTKVEIKRTVAAPSVFIFPPSDE

QLKSGTASVVCLLNNFYPREAKVQWKVDNALQSGNSQESVTEQDSKDSTYSLSSTLTLS

KADYEKHKVYACEVTHQGLSSPVTKSFNRGEC:

CAMPATH1 (10E1) MEFAB (183) heavy chain                   SEQ ID NO: 32
QVQLQESGGGLVRPSQTLSLTCTVSGFTFTDFYMNWVRQSPGRGLEWIGFIRDKAKGYT

TEYNPSVKGRVTMLVDTSKNQFSLRLSSVTAADTAWYCAREGHTAAPFDYWGQGSLV

TVSSASTKGPSVFPLAPSSKSTSGGTAALGCLVKDYFPEPVTVSWNSGALTSGVHTFPAV

LQSSGLYSLSSVVTVPSSSLGTQTYICNVNHKPSNTKVDKKVE:

CAMPATH1 (10E1) MEFAB (E83) light chain                   SEQ ID NO: 33
DIQMTQSPILLSASVGDRVTITCKASQNIDKYLNWYQQRTNGSPRLLIYNTNNLQTGVPS

RFSGSGSGTDFTFTISSLQPEDEADYYCLQHISRPRTFGQGTKVEIKRTVAAPSVFIFPPSD

EQLKSGTASVVCLLNNFYPREAKVQWKVDNALQSGNSQESVTEQDSKDSTYSLSSTLTL

SKADYEKHKVYACEVTHQGLSSPVTKSFNRGEC:

CAMPATH1 (10E1) MEFAB (E83) heavy chain                   SEQ ID NO: 34
QVQLQESGGGLVRPSQTLSLTCTVSGFTFTDFYMNWVRQSPGRGLEWIGFIRDKAKGYT
```

TEYNPSVKGRVTMLVDTSKNQFSLRLSSVTAADTAWYCAREGHTAAPFDYWGQGSLV

TVSSASTKGPSVFPLAPSSKSTSGGTAALGCLVKDYFPEPVTVSWNSGALTSGVHTFPAV

LQSSGLYSLSSVVTVPSSSLGTQTYICNVNHKPSNTKVDKKVE:

Tissue factor Fab (1jps) MEFAB light chain      SEQ ID NO: 35
DIQMTQSPILLSASVGDRVTITCRASRDIKSYLNWYQQRTNGSPRLLIYYATSLAEGVPSR

FSGSGSGTDYTLTISSLQPEDIADYYCLQHGESPWTFGQGTKVEIKRTVAAPSVFIFPPSD

EQLKSGTASVVCLLNNFYPREAKVQWKVDNALQSGNSQESVTEQDSKDSTYSLSSTLTL

SKADYEKHKVYACEVTHQGLSSPVTKSFNRGEC

Tissue factor Fab (1jps) MEFAB heavy chain      SEQ ID NO: 36
EVQLVESGGGLVQPGGSLRLSCAASGFNIKEYYMEIWVRQSPGKGLEWVGLIDPEQGNT

IYDPKFQDRATISADNSKNTAYLQMNSLRAEDTAIYYCARDTAAYFDYWGQGTLVTVS

SASTKGPSVFPLAPSSKSTSGGTAALGCLVKDYFPEPVTVSWNSGALTSGVHTFPAVLQS

SGLYSLSSVVTVPSSSLGTQTYICNVNHKPSNTKVDKKVEPKSCDKTHT

Tissue factor Fab (1jps) MEFAB (183) light chain      SEQ ID NO: 37
DIQMTQSPILLSASVGDRVTITCRASRDIKSYLNWYQQRTNGSPRLLIYYATSLAEGVPSR

FSGSGSGTDYTLTISSLQPEDEADYYCLQHGESPWTFGQGTKVEIKRTVAAPSVFIFPPSD

EQLKSGTASVVCLLNNFYPREAKVQWKVDNALQSGNSQESVTEQDSKDSTYSLSSTLTL

SKADYEKHKVYACEVTHQGLSSPVTKSFNRGEC

Tissue factor Fab (1jps) MEFAB (183) heavy chain      SEQ ID NO: 38
EVQLVESGGGLVQPGGSLRLSCAASGFNIKEYYMEIWVRQSPGKGLEWVGLIDPEQGNT

IYDPKFQDRATISADNSKNTAYLQMNSLRAEDTAIYYCARDTAAYFDYWGQGTLVTVS

SASTKGPSVFPLAPSSKSTSGGTAALGCLVKDYFPEPVTVSWNSGALTSGVHTFPAVLQS

SGLYSLSSVVTVPSSSLGTQTYICNVNHKPSNTKVDKKVEPKSCDKTHT

ANT1-PRP - prion MEFAB (183) (GI: 19204296) light chain      SEQ ID NO: 39
EIVLTQSPIIIVISASPGEKVTMTCSASSSVSYMEIWYQQRTNGSPRRWIYDTSKLASGVPAR

FSGSGSGTSYSLTISSMEAEDIADYFCHQWRSNPYTFGGGTKLEIKRADAAPTVSIFPPSS

EQLTSGGASVVCFLNNFYPKEINVKWKIDGSERQNGVLNSWTDQDSKDSTYSMSSTLTL

TKDEYERHNSYTCEATHKTSTSPIVKSFNRNEC

ANTI-PRP - prion MEFAB (183) (GI: 19204296) heavy chain      SEQ ID NO: 40
EVQLQQSGGELVKPGSSVKISCKASRNTFTDYNLDWVKQSHGKTLEWIGNVYPNNGVT

GYNQKFRGKATLTVDKSSSTAYMELHSLTSEDSAIYYCALYYYDVSYWGQGTLVTVSS

AKTTPPSVYPLAPGSAAQTSMVTLGCLVKGYFPEPVTVTWNSGSLSSGVHTFPAVLQSD

LYTLSSSVTVPSSTWPSQSVTCNVAHPASSTKVDKKITPR

ANTI-PRP - prion MEFAB (1E83) (GI: 19204296) light chain      SEQ ID NO: 41
EIVLTQSPIIIVISASPGEKVTMTCSASSSVSYMHWYQQRTNGSPRRWIYDTSKLASGVPAR

FSGSGSGTSYSLTISSMEAEDEADYFCHQWRSNPYTFGGGTKLEIKRADAAPTVSIFPPSS

EQLTSGGASVVCFLNNFYPKEINVKWKIDGSERQNGVLNSWTDQDSKDSTYSMSSTLTL

TKDEYERHNSYTCEATHKTSTSPIVKSFNRNEC

ANT1-PRP - prion MEFAB (E83) (GI: 19204296) heavy chain      SEQ ID NO: 42
EVQLQQSGGELVKPGSSVKISCKASRNTFTDYNLDWVKQSHGKTLEWIGNVYPNNGVT

GYNQKFRGKATLTVDKSSSTAYMELHSLTSEDSAIYYCALYYYDVSYWGQGTLVTVSS

AKTTPPSVYPLAPGSAAQTSMVTLGCLVKGYFPEPVTVTWNSGSLSSGVHTFPAVLQSD

LYTLSSSVTVPSSTWPSQSVTCNVAHPASSTKVDKKITPR

| | |
|---|---|
| daclizumab MEFAB (183) light chain<br>DIQMTQSPILLSASVGDRVTITCSASSSISYMHWYQQRTNGSPRLLIYTTSNLASGVPARF<br>SGSGSGTEFTLTISSLQPDDIADYYCHQRSTYPLTFGQGTKVEVKRTVAAPSVFIFPPSDE<br>QLKSGTASVVCLLNNFYPREAKVQWKVDNALQSGNSQESVTEQDSKDSTYSLSSTLTLS<br>KADYEKHKVYACEVTHQGLSSPVTKSFNRGEC | SEQ ID NO: 43 |
| daclizumab (183) heavy chain<br>QVQLVQSGGEVKKPGSSVKVSCKASGYTFTSYRMHWVRQSPGQGLEWIGYINPSTGYT<br>EYNQKFKDKATITADESTNTAYMELSSLRSEDTAIYYCARGGGVFDYWGQGTLVTVSS<br>ASTKGPSVFPLAPSSKSTSGGTAALGCLVKDYFPEPVTVSWNSGALTSGVHTFPAVLQSS<br>GLYSLSSVVTVPSSSLGTQTYICNVNHKPSNTKVDKKVEP | SEQ ID NO: 44 |
| daclizumab MEFAB (E83) light chain<br>DIQMTQSPILLSASVGDRVTITCSASSSISYMHWYQQRTNGSPRLLIYTTSNLASGVPARF<br>SGSGSGTEFTLTISSLQPDDEADYYCHQRSTYPLTFGQGTKVEVKRTVAAPSVFIFPPSDE<br>QLKSGTASVVCLLNNFYPREAKVQWKVDNALQSGNSQESVTEQDSKDSTYSLSSTLTLS<br>KADYEKHKVYACEVTHQGLS SPVTKSFNRGEC | SEQ ID NO: 45 |
| daclizumab (E83) heavy chain<br>QVQLVQSGGEVKKPGSSVKVSCKASGYTFTSYRMEIWVRQSPGQGLEWIGYINPSTGYT<br>EYNQKFKDKATITADESTNTAYMELSSLRSEDTAIYYCARGGGVFDYWGQGTLVTVSS<br>ASTKGPSVFPLAPSSKSTSGGTAALGCLVKDYFPEPVTVSWNSGALTSGVHTFPAVLQSS<br>GLYSLSSVVTVPSSSLGTQTYICNVNHKPSNTKVDKKVEP | SEQ ID NO: 46 |
| MORAb-009 Anti-mesothelin monoclonal<br>antibody MEFAB (183) light chain<br>DIELTQSPIIIVISASPGEKVTMTCSASSSVSYMEIWYQQRTNGSPRRWIYDTSKLASGVPGR<br>FSGSGSGNSYSLTISSVEAEDIADYYCQQWSKHPLTFGSGTKVEIKRTVAAPSVFIFPPSD<br>EQLKSGTASVVCLLNNFYPREAKVQWKVDNALQSGNSQESVTEQDSKDSTYSLSSTLTL<br>SKADYEKHKVYACEVTHQGLSSPVTKSFNRGEC | SEQ ID NO: 47 |
| MORAb-009 Anti-mesothelin monoclonal<br>antibody MEFAB (183) heavy chain<br>EVQLQQSGGELEKPGASVKISCKASGYSFTGYTMNWVKQSHGKSLEWIGLITPYNGASS<br>YNQKFRGKATLTVDKSSSTAYMDLLSLTSEDSAIYFCARGGYDGRGFDYWGSGTPVTV<br>SSASTKGPSVFPLAPSSKSTSGGTAALGCLVKDYFPEPVTVSWNSGALTSGVHTFPAVLQ<br>SSGLYSLSSVVTVPSSSLGTQTYICNVNHKPSNTKVDKKVEPKSCDKTHTCPPC | SEQ ID NO: 48 |
| MORAb-009 Anti-mesothelin monoclonal<br>antibody MEFAB (E83) light chain<br>DIELTQSPIIIVISASPGEKVTMTCSASSSVSYMEIWYQQRTNGSPRRWIYDTSKLASGVPGR<br>FSGSGSGNSYSLTISSVEAEDEADYYCQQWSKHPLTFGSGTKVEIKRTVAAPSVFIFPPSD<br>EQLKSGTASVVCLLNNFYPREAKVQWKVDNALQSGNSQESVTEQDSKDSTYSLSSTLTL<br>SKADYEKHKVYACEVTHQGLSSPVTKSFNRGEC | SEQ ID NO: 49 |
| MORAb-009 Anti-mesothelin monoclonal<br>antibody MEFAB (E83) heavy chain<br>EVQLQQSGGELEKPGASVKISCKASGYSFTGYTMNWVKQSHGKSLEWIGLITPYNGASS<br>YNQKFRGKATLTVDKSSSTAYMDLLSLTSEDSAIYFCARGGYDGRGFDYWGSGTPVTV<br>SSASTKGPSVFPLAPSSKSTSGGTAALGCLVKDYFPEPVTVSWNSGALTSGVHTFPAVLQ<br>SSGLYSLSSVVTVPSSSLGTQTYICNVNHKPSNTKVDKKVEPKSCDKTHTCPPC | SEQ ID NO: 50 |
| anti-CD20 antibody Ofatumumab MEFAB (183) light chain<br>EIVLTQSPILLSLSPGERATLSCRASQSVSSYLAWYQQRTNGSPRLLIYDASNRATGIPAR | SEQ ID NO: 51 |

FSGSGSGTDFTLTISSLEPEDIADYYCQQRSNWPITFGQGTRLEIKRTVAAPSVFIFPPSDE

QLKSGTASVVCLLNNFYPREAKVQWKVDNALQSGNSQESVTEQDSKDSTYSLSSTLTLS

KADYEKHKVYACEVTHQGLSSPVTKSFNRGEC anti-CD20 antibody Ofatumumab MEFAB (183) heavy chain  SEQ ID NO: 52
EVQLVESGGGLVQPGRSLRLSCAASGFTFNDYAMHWVRQSPGKGLEWVSTISWNSGSI

GYADSVKGRFTISRDNAKKSLYLQMNSLRAEDTAIYYCAKDIQYGNYYYGMDVWGQG

TTVTVSSASTKGPSVFPLAPGSSKSTSGTAALGCLVKDYFPEPVTVSWNSGALTSGVHTF

PAVLQSSGLYSLSSVVTVPSSSLGTQTYICNVNHKPSNTKVDKKVEP anti-CD20 antibody Ofatumumab MEFAB (E83) light chain  SEQ ID NO: 53
EIVLTQSPILLSLSPGERATLSCRASQSVSSYLAWYQQRTNGSPRLLIYDASNRATGIPAR

FSGSGSGTDFTLTISSLEPEDIADYYCQQRSNWPITFGQGTRLEIKRTVAAPSVFIFPPSDE

QLKSGTASVVCLLNNFYPREAKVQWKVDNALQSGNSQESVTEQDSKDSTYSLSSTLTLS

KADYEKHKVYACEVTHQGLSSPVTKSFNRGEC anti-CD20 antibody Ofatumumab MEFAB (E83) heavy chain  SEQ ID NO: 54
EVQLVESGGGLVQPGRSLRLSCAASGFTFNDYAMHWVRQSPGKGLEWVSTISWNSGSI

GYADSVKGRFTISRDNAKKSLYLQMNSLRAEDTAIYYCAKDIQYGNYYYGMDVWGQG

TTVTVSSASTKGPSVFPLAPGSSKSTSGTAALGCLVKDYFPEPVTVSWNSGALTSGVHTF

PAVLQSSGLYSLSSVVTVPSSSLGTQTYICNVNHKPSNTKVDKKVEP

Notch! Negative Regulatory Region  SEQ ID NO: 55
antibody MEFAB (183) light chain
DIQMTQSPILLSASVGDRVTITCRASQDVSTAVAWYQQRTNGSPRLLIYSASFLYSGVPS

RFSGSGSGTDFTLTISSLQPEDIADYYCQQFYTTPSTFGQGTKVEIKRTVAAPSVFIFPPSD

EQLKSGTASVVCLLNNFYPREAKVQWKVDNALQSGNSQESVTEQDSKDSTYSLSSTLTL

SKADYEKHKVYACEVTHQGLSSPVTKSFNRGEC

Notch! Negative Regulatory Region  SEQ ID NO: 56
antibody MEFAB (183) heavy chain
EVQLVESGGGLVQPGGSLRLSCAASGFTFSSYWIHWVRQSPGKGLEWVARINPPNRSNQ

YADSVKGRFTISADTSKNTAYLQMNSLRAEDTAIYYCARGSGFRWVMDYWGQGTLVT

VSSASTKGPSVFPLAPSSKSTSGGTAALGCLVKDYFPEPVTVSWNSGALTSGVHTFPAVL

QSSGLYSLSSVVTVPSSSLGTQTYICNVNHKPSNTKVDKKVEPKSCDKTHT

Notch! Negative Regulatory Region  SEQ ID NO: 57
antibody MEFAB (E83) light chain
DIQMTQSPILLSASVGDRVTITCRASQDVSTAVAWYQQRTNGSPRLLIYSASFLYSGVPS

RFSGSGSGTDFTLTISSLQPEDEADYYCQQFYTTPSTFGQGTKVEIKRTVAAPSVFIFPPSD

EQLKSGTASVVCLLNNFYPREAKVQWKVDNALQSGNSQESVTEQDSKDSTYSLSSTLTL

SKADYEKHKVYACEVTHQGLSSPVTKSFNRGEC

Notch! Negative Regulatory Region  SEQ ID NO: 58
antibody MEFAB (E83) heavy chain
EVQLVESGGGLVQPGGSLRLSCAASGFTFSSYWIHWVRQSPGKGLEWVARINPPNRSNQ

YADSVKGRFTISADTSKNTAYLQMNSLRAEDTAIYYCARGSGFRWVMDYWGQGTLVT

VSSASTKGPSVFPLAPSSKSTSGGTAALGCLVKDYFPEPVTVSWNSGALTSGVHTFPAVL

QSSGLYSLSSVVTVPSSSLGTQTYICNVNHKPSNTKVDKKVEPKSCDKTHT anti-HER3 Fab RG7116 MEFAB (183) light chain  SEQ ID NO: 59
DIVMTQSPILLAVSLGERATINCKSSQSVLNSGNQKNYLTWYQQRTNGSPRLLIYWAST

RESGVPDRFSGSGSGTDFTLTISSLQAEDIADYYCQSDYSYPYTFGQGTKLEIKRTVAAPS

-continued

VFIFPPSDEQLKSGTASVVCLLNNFYPREAKVQWKVDNALQSGNSQESVTEQDSKDSTY

SLS STLTLSKADYEKHKVYACEVTHQGLSSPVTKSFNRGEC anti-HER3 Fab RG7116 MEFAB (183) heavy chain  SEQ ID NO: 60
QVQLVQSGGGVKKPGASVKVSCKASGYTFRSSYISWVRQSPGQGLEWMGWIYAGTGS

PSYNQKLQGRVTMTTDTSTSTAYMELRSLRSDDTAIYYCARHRDYYSNSLTYWGQGTL

VTVSSASTKGPSVFPLAPSSKSTSGGTAALGCLVKDYFPEPVTVSWNSGALTSGVHTFPA

VLQSSGLYSLSSVVTVPSSSLGTQTYICNVNHKPSNTKVDKKVEPKSCDKTH anti-HER3 Fab RG7116 MEFAB (E83) light chain  SEQ ID NO: 61
DIVMTQSPILLAVSLGERATINCKSSQSVLNSGNQKNYLTWYQQRTNGSPRLLIYWAST

RESGVPDRFSGSGSGTDFTLTISSLQAEDEADYYCQSDYSYPYTFGQGTKLEIKRTVAAP

SVFIFPPSDEQLKSGTASVVCLLNNFYPREAKVQWKVDNALQSGNSQESVTEQDSKDST

YSLSSTLTLSKADYEKHKVYACEVTHQGLSSPVTKSFNRGEC anti-HER3 Fab RG7116 MEFAB (E83) heavy chain  SEQ ID NO: 62
QVQLVQSGGGVKKPGASVKVSCKASGYTFRSSYISWVRQSPGQGLEWMGWIYAGTGS

PSYNQKLQGRVTMTTDTSTSTAYMELRSLRSDDTAIYYCARHRDYYSNSLTYWGQGTL

VTVSSASTKGPSVFPLAPSSKSTSGGTAALGCLVKDYFPEPVTVSWNSGALTSGVHTFPA

VLQSSGLYSLSSVVTVPSSSLGTQTYICNVNHKPSNTKVDKKVEPKSCDKTH

Rituximab MEFAB (183) light chain  SEQ ID NO: 63
QIVLSQSPIILSASPGEKVTMTCRASSSVSYIHWFQQRTNGSPRPWIYATSNLASGVPVRF

SGSGSGTSYSLTISRVEAEDIADYYCQQWTSNPPTFGGGTKLEIKRTVAAPSVFIFPPSDE

QLKSGTASVVCLLNNFYPREAKVQWKVDNALQSGNSQESVTEQDSKDSTYSLSSTLTLS

KADYEKHKVYACEVTHQGLSSPVTKSFNRGEC

Rituximab MEFAB (183) heavy chain  SEQ ID NO: 64
QVQLQQPGGGLVKPGASVKMSCKASGYTFTSYNMHWVKQTPGRGLEWIGAIYPGNGD

TSYNQKFKGKATLTADKSSSTAYMQLSSLTSEDSAIYYCARSTYYGGDWYFNVWGAGT

TVTVSAASTKGPSVFPLAPSSKSTSGGTAALGCLVKDYFPEPVTVSWNSGALTSGVHTFP

AVLQSSGLYSLSSVVTVPSSSLGTQTYICNVNHKPSNTKVDKKVEPKSC

Rituximab MEFAB (E83) light chain  SEQ ID NO: 65
QIVLSQSPIILSASPGEKVTMTCRASSSVSYIHWFQQRTNGSPRPWIYATSNLASGVPVRF

SGSGSGTSYSLTISRVEAEDEADYYCQQWTSNPPTFGGGTKLEIKRTVAAPSVFIFPPSDE

QLKSGTASVVCLLNNFYPREAKVQWKVDNALQSGNSQESVTEQDSKDSTYSLSSTLTLS

KADYEKHKVYACEVTHQGLSSPVTKSFNRGEC

Rituximab MEFAB (E83) heavy chain  SEQ ID NO: 66
QVQLQQPGGGLVKPGASVKMSCKASGYTFTSYNMHWVKQTPGRGLEWIGAIYPGNGD

TSYNQKFKGKATLTADKSSSTAYMQLSSLTSEDSAIYYCARSTYYGGDWYFNVWGAGT

TVTVSAASTKGPSVFPLAPSSKSTSGGTAALGCLVKDYFPEPVTVSWNSGALTSGVHTFP

AVLQSSGLYSLSSVVTVPSSSLGTQTYICNVNHKPSNTKVDKKVEPKSC anti-osteopontin antibody 23C3 MEFAB (183) light chain  SEQ ID NO: 67
YIQMTQSPILLSVSVGETVTITCRASENIYSFLAWYQQRTNGSPRLLVYAATNLADGVPS

RFSGSGSGTQFSLKINSLQSEDIADYYCQHFWGTPFTFGSGTKLEIKRSDAAPTVSIFPPSA

AQLSSGGGSVVCFLNNFYPKDINVKWKIDGAERGNGVLNSWTSQDSADSTYSMSSTLT

SGGDEYERHNSYTCEATHKTSTSPIVKSFNRGEC anti-osteopontin antibody 23C3 MEFAB (183) heavy chain  SEQ ID NO: 68
EVQLVESGGGLVQPKGSLKISCAASGFTFNIYAMNWVRQSPGKGLEWVARIRSQSNNY

```
TTYYADSVKDRFTISRDDSQSMLYLQMNNLKTEDTAIYYCVRQMGDYWGQGTTLTVSS

AVKTPPSVYPLAPGGGAISNSMVTLGCLVNGYFPEPVTVTWNAGSLGSGVHTFPAVLQS

DLYTLSSSVTVPVSTWPSEAVTCNVAHPASATSVDKAISPV
``` anti-osteopontin antibody 23C3 MEFAB (E83) light chain     SEQ ID NO: 69
```
YIQMTQSPILLSVSVGETVTITCRASENIYSFLAWYQQRTNGSPRLLVYAATNLADGVPS

RFSGSGSGTQFSLKINSLQSEDIADYYCQHFWGTPFTFGSGTKLEIKRSDAAPTVSIFPPSA

AQLSSGGGSVVCFLNNFYPKDINVKWKIDGAERGNGVLNSWTSQDSADSTYSMSSTLT

SGGDEYERHNSYTCEATHKTSTSPIVKSFNRGEC
``` anti-osteopontin antibody 23C3 MEFAB (E83) heavy chain     SEQ ID NO: 70
```
EVQLVESGGGLVQPKGSLKISCAASGFTFNIYAMNWVRQSPGKGLEWVARIRSQSNNY

TTYYADSVKDRFTISRDDSQSMLYLQMNNLKTEDTAIYYCVRQMGDYWGQGTTLTVSS

AVKTPPSVYPLAPGGGAISNSMVTLGCLVNGYFPEPVTVTWNAGSLGSGVHTFPAVLQS

DLYTLSSSVTVPVSTWPSEAVTCNVAHPASATSVDKAISPV
``` anti-uPAR Fab ATN-658 MEFAB (183) light chain     SEQ ID NO: 71
```
DVVMTQTPLLLSVTIGQPASISCKSSQSLLDSDGKTYLNWLLQRTNGSPRRLIYLVSKLD

SGVPDRFTGSGSGTDFTLKISRVEAEDIADYYCWQGTHFPLTFGAGTKLELKRADAAPT

VSIFPPSSEQLTSGGASVVCFLNNFYPKDINVKWKIDGSERQNGVLNSWTDQDSKDSTYS

MSSTLTLTKDEYERHNSYTCEATHKTSTSPIVKSFNRNEC
``` anti-uPAR Fab ATN-658 MEFAB (183) heavy chain     SEQ ID NO: 72
```
EVQLQQSGGGLVKTGASVKISCKASGYSFTSYYMEIWVKQSHGKSLEWIGEINPYNGGA

SYNQKIKGRATFTVDTSSRTAYMQFNSLTSEDSAIYYCARSIYGHSVLDYWGQGTSVSV

SSAKTTPPSVYPLAPGSAAQTNSMVTLGCLVKGYFPEPVTVTWNSGSLSSGVHTFPAVL

QSDLYTLSSSVTVPSSTWPSQTVTCNVAHPASSTKVDKKIVPRDCGCKPCIC
``` anti-uPAR Fab ATN-658 MEFAB (E83) light chain     SEQ ID NO: 73
```
DVVMTQTPLLLSVTIGQPASISCKSSQSLLDSDGKTYLNWLLQRTNGSPRRLIYLVSKLD

SGVPDRFTGSGSGTDFTLKISRVEAEDEADYYCWQGTHFPLTFGAGTKLELKRADAAPT

VSIFPPSSEQLTSGGASVVCFLNNFYPKDINVKWKIDGSERQNGVLNSWTDQDSKDSTYS

MSSTLTLTKDEYERHNSYTCEATHKTSTSPIVKSFNRNEC
``` anti-uPAR Fab ATN-658 MEFAB (E83) heavy chain     SEQ ID NO: 74
```
EVQLQQSGGGLVKTGASVKISCKASGYSFTSYYMEIWVKQSHGKSLEWIGEINPYNGGA

SYNQKIKGRATFTVDTSSRTAYMQFNSLTSEDSAIYYCARSIYGHSVLDYWGQGTSVSV

SSAKTTPPSVYPLAPGSAAQTNSMVTLGCLVKGYFPEPVTVTWNSGSLSSGVHTFPAVL

QSDLYTLSSSVTVPSSTWPSQTVTCNVAHPASSTKVDKKIVPRDCGCKPCIC
``` therapeutic influenza A MEFAB (183) light chain     SEQ ID NO: 75
```
IVLTQSPILLSVSPGERATLSCRASQVISHNLAWYQQRTNGSPRLLIYGASTRASGIPARFS

GSGSGTDYTLTITSLQPEDIADYYCQHYSNWPPRLTFGGGTKVEIKRTVAAPSVFIFPPSD

EQLKSGTASVVCLLNNFYPREAKVQWKVDNALQSGNSQESVTEQDSKDSTYSLSSTLTL

SKADYEKHKVYACEVTHQGLSSPVTKSFNRGEC
``` therapeutic influenza A MEFAB (183) heavy chain     SEQ ID NO: 76
```
EVQLQQSGGGLVKTGASVKISCKASGYSFTSYYMHWVKQSHGKSLEWIGEINPYNGGA

SYNQKIKGRATFTVDTSSRTAYMQFNSLTSEDSAIYYCARSIYGHSVLDYWGQGTSVSV

SSAKTTPPSVYPLAPGSAAQTNSMVTLGCLVKGYFPEPVTVTWNSGSLSSGVHTFPAVL

QSDLYTLSSSVTVPSSTWPSQTVTCNVAHPASSTKVDKKIVPRDCGCKPCIC
```

-continued

| | |
|---|---|
| therapeutic influenza A MEFAB (E83) light chain<br>IVLTQSPILLSVSPGERATLSCRASQVISHNLAWYQQRTNGSPRLLIYGASTRASGIPARFS<br><br>GSGSGTDYTLTITSLQPEDEADYYCQHYSNWPPRLTFGGGTKVEIKRTVAAPSVFIFPPS<br><br>DEQLKSGTASVVCLLNNFYPREAKVQWKVDNALQSGNSQESVTEQDSKDSTYSLSSTL<br><br>TLSKADYEKHKVYACEVTHQGLSSPVTKSFNRGEC | SEQ ID NO: 77 |
| therapeutic influenza A MEFAB (E83) heavy chain<br>EVQLQQSGGGLVKTGASVKISCKASGYSFTSYYMHWVKQSHGKSLEWIGEINPYNGGA<br><br>SYNQKIKGRATFTVDTSSRTAYMQFNSLTSEDSAIYYCARSIYGHSVLDYWGQGTSVSV<br><br>SSAKTTPPSVYPLAPGSAAQTNSMVTLGCLVKGYFPEPVTVTWNSGSLSSGVHTFPAVL<br><br>QSDLYTLSSSVTVPSSTWPSQTVTCNVAHPASSTKVDKKIVPRDCGCKPCIC | SEQ ID NO: 78 |
| West Nile Virus Envelope Protein DIII in complex<br>with neutralizing E16 antibody MEFAB (183) light chain<br>DIVMTQ SHILMSTSVGDRVSITCKASQDVSTAVAWYQQRTNGSPRLLISWASTRHTGVP<br><br>DRFTGSGSGTDYTLTISSVQAEDIADYYCQQHYTTPLTFGAGTKLELKRADAAPTVSIFP<br><br>PSSEQLTSGGASVVCFLNNFYPKDINVKWKIDGSERQNGVLNSWTDQDSKDSTYSMSST<br><br>LTLTKDEYERHNSYTCEATHKTSTSPIVKSFNRGEC | SEQ ID NO: 79 |
| West Nile Virus Envelope Protein DIII in complex<br>with neutralizing E16 antibody MEFAB (183) heavy chain<br>QVQLQQSGGGLMKPGASVQISCKATGYTFSDYWIEWVKQSPGHGLEWIGDILCGTGRT<br><br>RYNEKLKAMATFTADTSSNTAFMQLSSLTSEDSAIYYCARSASYGDYADYWGHGTTLT<br><br>VSSAKTTPPSVYPLAPGCGDTTGSSVTLGCLVKGYFPESVTVTWNSGSLSSSVHTFPALL<br><br>QSGLYTMSSSVTVPSSTWPSQTVTCSVAHPASSTTVDKKLEPS | SEQ ID NO: 80 |
| West Nile Virus Envelope Protein DIII in complex<br>with neutralizing E16 antibody MEFAB (E83) light chain<br>DIVMTQSHILMSTSVGDRVSITCKASQDVSTAVAWYQQRTNGSPRLLISWASTRHTGVP<br><br>DRFTGSGSGTDYTLTISSVQAEDEADYYCQQHYTTPLTFGAGTKLELKRADAAPTVSIFP<br><br>PSSEQLTSGGASVVCFLNNFYPKDINVKWKIDGSERQNGVLNSWTDQDSKDSTYSMSST<br><br>LTLTKDEYERHNSYTCEATHKTSTSPIVKSFNRGEC | SEQ ID NO: 81 |
| West Nile Virus Envelope Protein DIII in complex<br>with neutralizing E16 antibody MEFAB (E83) heavy chain<br>QVQLQQSGGGLMKPGASVQISCKATGYTFSDYWIEWVKQSPGHGLEWIGDILCGTGRT<br><br>RYNEKLKAMATFTADTSSNTAFMQLSSLTSEDSAIYYCARSASYGDYADYWGHGTTLT<br><br>VSSAKTTPPSVYPLAPGCGDTTGSSVTLGCLVKGYFPESVTVTWNSGSLSSSVHTFPALL<br><br>QSGLYTMSSSVTVPSSTWPSQTVTCSVAHPASSTTVDKKLEPS | SEQ ID NO: 82 |
| PVKQLLNFDLLKLAGDVESNPGP | (SEQ ID NO: 83) |
| QCTNYALLKLAGDVESNPGP | (SEQ ID NO: 84) |
| ATNFSLLKQAGDVEENPGP | (SEQ ID NO: 85) |
| EGRGSLLTCGDVESNPGP | (SEQ ID NO: 86) |
| Humanized anti-CD19 meditope enabled heavy chain<br>EVQLVESGGGLVQPGGSLRLSCAASGVSLPDYGVSWVRQSPGKGLEWVAVIWGSETTY<br><br>YADSVKGRFTISADTSKNTYLQMNSLRAEDTAWYCSRHYYYGGSYAMDYWGQGTLV<br><br>TVSSASTKGPSVFPLAPSSKSTSGGTAALGCLVKDYFPEPVTVSWNSGALTSGVHTFPAV<br><br>LQSSGLYSLSSVVTVPSSSLGTQTYICNVNHKPSNTKVDKKVEP | SEQ ID NO: 111 |

| | |
|---|---|
| Humanized anti-CD19 meditope enabled light chain<br>DIQMTQSPILLSASVGDRVTITCRASQDISKYLNWYQQRTNGSPR | SEQ ID NO: 112 |
| LLIYHTSRLHSGVPSRFSGSRSGTDFTLTISSLQPEDIADYYCQQGNTLPYTFGAGTKVEI | |
| KRTVAAPSVFIFPPSDEQLKSGTASVVCLLNNFYPREAKVQWKVDNALQSGNSQESVTE | |
| QDSKDSTYSLSSTLTLSKADYEKHKVYACEVTHQGLSSPVTKSFNRGEC | |
| Humanized anti-CD19 meditope enabled I83E heavy chain<br>EVQLVESGGGLVQPGGSLRLSCAASGVSLPDYGVSWVRQSPGKGLEWVAVIWGSETTY | SEQ ID NO: 113 |
| YADSVKGRFTISADTSKNTYLQMNSLRAEDTAIYYCSRHYYYGGSYAMDYWGQGTLV | |
| TVSSASTKGPSVFPLAPSSKSTSGGTAALGCLVKDYFPEPVTVSWNSGALTSGVHTFPAV | |
| LQSSGLYSLSSVVTVPSSSLGTQTYICNVNHKPSNTKVDKKVEP | |
| Humanized anti-CD19 meditope enabled I83E light chain<br>DIQMTQSPILLSASVGDRVTITCRASQDISKYLNWYQQRTNGSPRLLIYHTSRLHSGVPSR | SEQ ID NO: 114 |
| FSGSRSGTDFTLTISSLQPEDEADYYCQQGNTLPYTFGAGTKVEIKRTVAAPSVFIFPPSD | |
| EQLKSGTASVVCLLNNFYPREAKVQWKVDNALQSGNSQESVTEQDSKDSTYSLSSTLTL | |
| SKADYEKHKVYACEVTHQGLSSPVTKSFNRGEC | |
| Anti-TAG72 (CC49) CC49 memAb I83E<br>enhanced Chothia heavy chain<br>EVQLVESGGGLVQPGGSLRLSCAASGYTFTDHAIHWVRQSPGKGLEWVAYFSPGNDDF | SEQ ID NO: 115 |
| KYADSVKGRFTISADTSKNTAYLQMNSLRAEDTAIYYCSRSLNMAYWGQGTLVTVSSA | |
| STKGPSVFPLAPSSKSTSGGTAALGCLVKDYFPEPVTVSWNSGALTSGVHTFPAVLQSSG | |
| LYSLSSVVTVPSSSLGTQTYICNVNHKPSNTKVDKKVEP | |
| Anti-TAG72 (CC49) CC49 memAb I83E<br>enhanced Chothia light chain<br>DIQMTQSPILLSASVGDRVTITCKSSQSLLYSGNQKNYLAWYQQRTNGSPRLLIYWASA | SEQ ID NO: 116 |
| RESGVPSRFSGSRSGTDFTLTISSLQPEDEADYYCQQYYSYPLTFGAGTKVEIKRTVAAPS | |
| VFIFPPSDEQLKSGTASVVCLLNNFYPREAKVQWKVDNALQSGNSQESVTEQDSKDSTY | |
| SLSSTLTLSKADYEKHKVYACEVTHQGLSSPVTKSFNRGEC | |
| Humanized CA19.9 memAb I83E enhanced Chothia heavy chain<br>EVQLVESGGGLVQPGGSLRLSCAASGFTFEAYAMHWVRQSPGKGLEWVASINWNSGRI | SEQ ID NO: 117 |
| AYADSVKGRFTISADTSKNTAYLQMNSLRAEDTAIYYCSRDIRRFSTGAEFEYWGQGTL | |
| VTVSSASTKGPSVFPLAPSSKSTSGGTAALGCLVKDYFPEPVTVSWNSGALTSGVHTFPA | |
| VLQSSGLYSLSSVVTVPSSSLGTQTYICNVNHKPSNTKVDKKVEP | |
| Humanized CA19.9 memAb I83E enhanced Chothia light chain<br>DIQMTQSPILLSASVGDRVTITCSGSSSNIGSNFVYWYQQRTNGSPRLLIYRNNQRPSGVP | SEQ ID NO: 118 |
| SRFSGSRSGTDFTLTISSLQPEDEADYYCAAWDDSLG????HYVFGAGTKVEIKRTVAAPS | |
| VFIFPPSDEQLKSGTASVVCLLNNFYPREAKVQWKVDNALQSGNSQESVTEQDSKDSTY | |
| SLSSTLTLSKADYEKHKVYACEVTHQGLSSPVTKSFNRGEC | |
| YP218 anti-mesothelin - Humanized YP218<br>memAb I83E enhanced Chothia heavy chain<br>EVQLVESGGGLVQPGGSLRLSCAASGFDLGFYFYACWVRQSPGKGLEWVACIYTAGSG | SEQ ID NO: 119 |
| STYYADSVKGRFTISADTSKNTAYLQMNSLRAEDTAIYYCSRSTANTRSTYLNLWGQGT | |
| LVTVSSASTKGPSVFPLAPSSKSTSGGTAALGCLVKDYFPEPVTVSWNSGALTSGVHTFP | |
| AVLQSSGLYSLSSVVTVPSSSLGTQTYICNVNHKPSNTKVDKKVEP | |
| YP218 anti-mesothelin - Humanized YP218<br>memAb I83E enhanced Chothia light chain<br>DIQMTQSPILLSASVGDRVTITCQASQRISSYLSWYQQRTNGSPRLLIYGASTLASGVPSR | SEQ ID NO: 120 |

```
FSGSRSGTDFTLTISSLQPEDEADYYCQSYFDSNWHAFGAGTKVEIKRTVAAPSVFIFPPS

DEQLKSGTASVVCLLNNFYPREAKVQWKVDNALQSGNSQESVTEQDSKDSTYSLSSTL

TLSKADYEKHKVYACEVTHQGLSSPVTKSFNRGEC
```

EMBODIMENTS

Embodiment 1

An isolated nucleic acid encoding a protein comprising: (i) an antibody region comprising a central cavity formed by a heavy chain variable (VH) region, a light chain variable (VL) region, a heavy chain constant region (CH) and a light chain constant region (CL), wherein said central cavity forms a peptide binding site comprising framework region amino acid residues; and (ii) a transmembrane domain.

Embodiment 2

The isolated nucleic acid of embodiment 1, wherein said antibody region is an antibody fragment.

Embodiment 3

The isolated nucleic acid of embodiment 1 or 2, wherein said antibody region comprises an Fc domain.

Embodiment 4

The isolated nucleic acid of one of embodiments 1 to 3, wherein said antibody region is a humanized antibody region.

Embodiment 5

The isolated nucleic acid of one of embodiment 1 to 4, further comprising an intracellular T-cell signaling sequence encoding an intracellular T-cell signaling domain.

Embodiment 6

The isolated nucleic acid of embodiment 5, wherein said intracellular T-cell signaling domain is a CD3 ζ intracellular T-cell signaling domain.

Embodiment 7

The isolated nucleic acid of one of embodiments 1-6 further comprising an intracellular co-stimulatory signaling sequence encoding an intracellular co-stimulatory signaling domain.

Embodiment 8

The isolated nucleic acid of embodiment 7, wherein said intracellular co-stimulatory signaling domain is a CD28 intracellular co-stimulatory signaling domain, a 4-1BB intracellular co-stimulatory signaling domain, a ICOS intracellular co-stimulatory signaling domain, or an OX-40 intracellular co-stimulatory signaling domain.

Embodiment 9

The isolated nucleic acid of one of embodiments 1-8 further comprising a spacer sequence encoding a spacer region.

Embodiment 10

The isolated nucleic acid of embodiment 9, wherein said spacer region is between said transmembrane domain and said antibody region.

Embodiment 11

The isolated nucleic acid of one of embodiments 1-10 further comprising a linker sequence encoding a linker domain.

Embodiment 12

The isolated nucleic acid of embodiment 11, wherein said linker domain is between said transmembrane domain and said intracellular T-cell signaling domain.

Embodiment 13

The isolated nucleic acid of embodiment 11, wherein said linker domain is between said intracellular T-cell signaling domain and said intracellular co-stimulatory signaling domain.

Embodiment 14

The isolated nucleic acid of embodiment 11, wherein said linker domain comprises the sequence GGCGG or GGG.

Embodiment 15

The isolated nucleic acid of one of embodiments 1 to 14 comprising: (i) a heavy chain sequence encoding a heavy chain domain of said protein, said heavy chain domain comprising a variable heavy chain domain and said transmembrane domain; and (ii) a light chain sequence encoding a light chain domain of said protein, said light chain domain comprising a variable light chain domain, wherein said variable heavy chain domain and said variable light chain domain together form at least a portion of said antibody region.

Embodiment 16

The isolated nucleic acid of embodiment 15 comprising a self-cleaving peptidyl sequence between said heavy chain sequence and said light chain sequence.

Embodiment 17

The isolated nucleic acid of embodiment 16, wherein said self-cleaving peptidyl linker sequence is a T2A sequence or a 2A sequence.

Embodiment 18

The isolated nucleic acid of one of embodiments 15 to 17, wherein said light chain sequence is 3' to said heavy chain sequence.

Embodiment 19

The isolated nucleic acid of one of embodiments 1 to 18, wherein said antibody region is a cetuximab meditope enabled domain, trastuzumab meditope enabled domain, pertuzumab meditope enabled domain, M5A meditope enabled domain or rituximab meditope enabled domain.

Embodiment 20

An isolated nucleic acid encoding a protein comprising a first portion comprising an antibody heavy chain variable domain and a second portion comprising an antibody light chain variable domain and an antibody light chain constant domain, wherein the first portion further comprises a transmembrane domain.

Embodiment 21

The isolated nucleic acid of embodiment 20, wherein said first portion further comprises an intracellular T-cell signaling domain.

Embodiment 22

The isolated nucleic acid of embodiment 20, wherein said intracellular T-cell signaling domain is a CD3 ζ intracellular T-cell signaling domain.

Embodiment 23

The isolated nucleic acid of one of embodiments 20-22, wherein said first portion further comprises an intracellular co-stimulatory signaling domain.

Embodiment 24

The isolated nucleic acid of embodiment 23, wherein said intracellular co-stimulatory signaling domain is a CD28 intracellular co-stimulatory signaling domain, a 4-1BB intracellular co-stimulatory signaling domain, a ICOS intracellular co-stimulatory signaling domain, or an OX-40 intracellular co-stimulatory signaling domain.

Embodiment 25

The isolated nucleic acid of one of embodiments 20-24 wherein said first portion further comprises a linker domain.

Embodiment 26

The isolated nucleic acid of embodiment 25, wherein said linker domain is between said transmembrane domain and said intracellular T-cell signaling domain.

Embodiment 27

The isolated nucleic acid of embodiment 25, wherein said linker domain is between said intracellular T-cell signaling domain and said intracellular co-stimulatory signaling domain.

Embodiment 28

The isolated nucleic acid of embodiment 25, wherein said linker domain comprises the sequence GGCGG or GGG.

Embodiment 29

The isolated nucleic acid of embodiment 20, wherein said first portion further comprises a CD3 ζ intracellular T-cell signaling domain and an intracellular co-stimulatory signaling domain.

Embodiment 30

The isolated nucleic acid molecule of embodiment 23, wherein the first portion comprises from the amino terminus to the carboxy terminus: the heavy chain variable domain, a heavy chain constant domain, the transmembrane domain, the CD3 ζ intracellular T-cell signaling domain and an intracellular co-stimulatory signaling domain.

Embodiment 31

The isolated nucleic acid molecule of one of embodiments 20-30 further comprising a spacer region positioned between the heavy chain variable domain and the transmembrane domain.

Embodiment 32

The isolated nucleic acid of embodiment 31, wherein said spacer region further comprises a hinge region.

Embodiment 33

The isolated nucleic acid of embodiment 20, wherein the antibody heavy chain variable domain and the antibody light chain variable domain are humanized.

Embodiment 34

The isolated nucleic acid of embodiment 20, wherein said first portion comprises a heavy chain constant domain.

Embodiment 35

The isolated nucleic acid of embodiment 20 comprising a self-cleaving peptidyl sequence between said first portion and said second portion.

Embodiment 36

The isolated nucleic acid of embodiment 35, wherein said self-cleaving peptidyl encoding sequence is a T2A encoding sequence or a 2A encoding sequence.

Embodiment 37

The isolated nucleic acid of one of embodiment 20, wherein the nucleic acid sequence encoding the second portion is 3' to the nucleic acid sequence encoding the first portion.

Embodiment 38

The isolated nucleic acid of one of embodiment 1 to 37, wherein said protein is an anti-CD19 protein, anti-CD20 protein, anti-CD22 protein, anti-CD30 protein, anti-CD33 protein, anti-CD44v6/7/8 protein, anti-CD123 protein, anti-CEA protein, anti-EGP-2 protein, anti-EGP-40 protein, anti-erb-B2 protein, anti-erb-B2,3,4 protein, anti-FBP protein, anti-fetal acetylcholine receptor protein, anti-GD2 protein, anti-GD3 protein, anti-Her2/neu protein, anti-IL-13R-a2 protein, anti-KDR protein, anti k-light chain protein, anti-LeY protein, anti-L1 cell adhesion molecule protein, anti-MAGE-A1 protein, anti-mesothelin protein, anti-murine CMV infected cell protein, anti-MUC2 protein, anti-NKGD2 protein, anti, oncofetal antigen protein, anti-PCSA protein, anti-PSMA protein, anti-TAA (targeted by mAb IfE) protein, anti-EGFR protein, anti-TAG-72 protein or anti-VEGF-72 protein.

Embodiment 39

The isolated nucleic acid of one of embodiments 1 to 38, further comprising a suicide gene sequence.

Embodiment 40

An expression vector comprising the nucleic acid of one of embodiments 1 to 39.

Embodiment 41

The expression vector of embodiment 40, wherein said expression vector is a viral vector.

Embodiment 42

The expression vector of embodiment 41, wherein said virus is a lentivirus or onco-retrovirus.

Embodiment 43

A T lymphocyte comprising the expression vector of one of embodiments 40 to 42.

Embodiment 44

A T lymphocyte of embodiment 43, comprising a first polypeptide and a second polypeptide, the first polypeptide comprising a heavy chain variable domain, a heavy chain constant domain, a transmembrane domain, a CD3 ζ signaling domain and a co-stimulatory T-cell signaling domain, the second polypeptide comprising a light chain variable domain and an light chain constant domain.

Embodiment 45

A recombinant protein comprising: (i) an antibody region comprising a central cavity formed by a heavy chain variable (VH) region and a light chain variable (VL) region, wherein said central cavity forms a peptide binding site comprising framework region amino acid residues; and (ii) a transmembrane domain.

Embodiment 46

The recombinant protein of embodiment 45, wherein said antibody region further comprises a heavy chain constant region (CH) and a light chain constant region (CL).

Embodiment 47

The recombinant protein of embodiment 45 or 46, wherein said antibody region comprises an Fc domain.

Embodiment 48

The recombinant protein of one of embodiments 45 to 47, wherein said antibody region is a humanized antibody region.

Embodiment 49

The recombinant protein of one of embodiments 45 to 48, wherein said antibody region does not comprise a scFv antibody region.

Embodiment 50

The recombinant protein of one of embodiments 45 to 49, wherein said protein further comprises an intracellular T-cell signaling domain.

Embodiment 51

The recombinant protein of embodiment 50, wherein said intracellular T-cell signaling domain is a CD3 ζ intracellular T-cell signaling domain.

Embodiment 52

The recombinant protein of one of embodiments 45 to 51, further comprising an intracellular co-stimulatory signaling domain.

Embodiment 53

The recombinant protein of embodiment 52, wherein said intracellular co-stimulatory signaling domain is a CD28 intracellular co-stimulatory signaling domain, a 4-1BB intracellular co-stimulatory signaling domain, a ICOS intracellular co-stimulatory signaling domain, or an OX-40 intracellular co-stimulatory signaling domain.

Embodiment 54

The recombinant protein of one of embodiments 45 to 53, further comprising a spacer region.

Embodiment 55

The recombinant protein of embodiment 54, wherein said spacer region is between said transmembrane domain and said antibody region.

Embodiment 56

The recombinant protein of embodiment one of embodiments 45-55, further comprising a linker domain.

Embodiment 57

The recombinant protein of embodiment 56, wherein said linker domain is between said transmembrane domain and said intracellular T-cell signaling domain.

Embodiment 58

The recombinant protein of embodiment 56, wherein said linker domain is between said intracellular T-cell signaling domain and said intracellular co-stimulatory signaling domain.

Embodiment 59

The recombinant protein of embodiment 57 or 58, wherein said linker domain comprises the sequence GGCGG or GGG.

Embodiment 60

The recombinant protein of one of embodiments 45 to 59, wherein said antibody region is a cetuximab meditope enabled domain, trasuzumab meditope enabled domain, pertuzumab meditope enabled domain, M5A meditope enabled domain or rituximab meditope enabled domain.

Embodiment 61

The recombinant protein of one of embodiments 45 to 60, wherein a compound comprising an peptidyl moiety is bound to said peptide binding site.

Embodiment 62

The recombinant protein of embodiment 61, wherein said compound is a multivalent meditope.

Embodiment 63

A recombinant protein comprising a first portion comprising an antibody heavy chain variable domain and a second portion comprising an antibody light chain variable domain and an antibody light chain constant domain, wherein the first portion further comprises a transmembrane domain, and wherein said antibody heavy chain variable domain, said antibody light chain variable domain and said antibody light chain constant domain together form an antibody region.

Embodiment 64

A T lymphocyte comprising the recombinant protein of one of embodiments 45 to 63, wherein said transmembrane domain is within the cell membrane of said T lymphocyte.

Embodiment 65

A method of treating cancer, said method comprising administering to a subject in need thereof an effective amount of the T-lymphocyte of embodiment 64, wherein said antibody region is an anti-cancer antibody region.

Embodiment 66

The method of embodiment 65, wherein said T-lymphocyte is an autologous T-lymphocyte.

Embodiment 67

The method of embodiment 65, wherein said T-lymphocyte is a heterologous T-lymphocyte.

Embodiment 68

The method of embodiment 65, wherein said cancer is a solid tumor cancer or hematologic malignancy.

Embodiment 69

The method of one of embodiments 65 to 68, wherein said cancer is ovarian cancer, renal cell carcinoma, a B-cell malignancy, leukemia, lymphoma, breast cancer, colorectal cancer, prostate cancer, neuroblastoma, melanoma, medulloblastoma, lung cancer, osteosarcoma, glioblastoma or glioma.

Embodiment 70

A method of reprogramming a T lymphocyte, said method comprising contacting a T lymphocyte with the expression vector of one of embodiments 40 to 42.

Embodiment 71

A method of detecting a cancer, said method comprising: (i) administering to a cancer patient an effective amount of a T lymphocyte comprising the recombinant protein of one of embodiments 45 to 63 and a compound comprising a peptidyl moiety capable of binding to said peptide binding site, wherein said compound further comprises a detectable label, and wherein said antibody region is an anti-cancer antibody region; (ii) allowing said compound to bind to said peptide binding site thereby forming a recombinant protein-compound complex; and (iii) detecting said recombinant protein-compound complex within said cancer patient thereby detecting said cancer.

What is claimed is:

1. An isolated nucleic acid encoding a protein comprising:
   (i) an antibody region comprising a central cavity formed by a heavy chain variable (VH) region, a light chain variable (VL) region, a heavy chain constant region (CH) and a light chain constant region (CL), wherein said central cavity forms a peptide binding site comprising framework region amino acid residues; and
   (ii) a transmembrane domain.

2. The isolated nucleic acid of claim 1, wherein said antibody region is an antibody fragment.

3. The isolated nucleic acid of claim 1, wherein said antibody region comprises an Fc domain.

4. The isolated nucleic acid of claim 1, wherein said antibody region is a humanized antibody region.

5. The isolated nucleic acid of claim 1, further comprising a nucleic acid sequence encoding an intracellular T-cell signaling domain.

6. The isolated nucleic acid of claim 5, wherein said intracellular T-cell signaling domain is a CD3 ζ intracellular T-cell signaling domain.

7. The isolated nucleic acid of claim 6, further comprising a nucleic acid sequence encoding an intracellular co-stimulatory signaling domain.

8. The isolated nucleic acid of claim 7, wherein said intracellular co-stimulatory signaling domain is a CD28 intracellular co-stimulatory signaling domain, a 4-1BB intracellular co-stimulatory signaling domain, a ICOS intracellular co-stimulatory signaling domain, or an OX-40 intracellular co-stimulatory signaling domain.

9. The isolated nucleic acid of claim 8, further comprising a spacer sequence encoding a spacer region.

10. The isolated nucleic acid of claim 9, wherein said spacer region is between said transmembrane domain and said antibody region.

11. The isolated nucleic acid of claim 10, further comprising a linker sequence encoding a linker domain.

12. The isolated nucleic acid of claim 11, wherein said linker domain is between said transmembrane domain and said intracellular T-cell signaling domain.

13. The isolated nucleic acid of claim 11, wherein said linker domain is between said intracellular T-cell signaling domain and said intracellular co-stimulatory signaling domain.

14. The isolated nucleic acid of claim 11, wherein said linker domain comprises the sequence GGCGG or GGG.

15. The isolated nucleic acid of claim 1 comprising:
   (i) a heavy chain sequence encoding a heavy chain domain of said protein, said heavy chain domain comprising a variable heavy chain domain and said transmembrane domain; and
   (ii) a light chain sequence encoding a light chain domain of said protein, said light chain domain comprising a variable light chain domain, wherein said variable heavy chain domain and said variable light chain domain together form at least a portion of said antibody region.

16. The isolated nucleic acid of claim 15 encoding a self-cleaving peptidyl sequence between said heavy chain sequence and said light chain sequence.

17. The isolated nucleic acid of claim 16, wherein said self-cleaving peptidyl linker sequence is a T2A sequence or a 2A sequence.

18. The isolated nucleic acid of 17, wherein said light chain sequence is 3' to said heavy chain sequence.

19. The isolated nucleic acid of 17, wherein said light chain sequence is 5' to said heavy chain sequence.

20. A T lymphocyte comprising the isolated nucleic acid of claim 1.

\* \* \* \* \*